(12) United States Patent
Erickson et al.

(10) Patent No.: US 6,632,979 B2
(45) Date of Patent: Oct. 14, 2003

(54) RODENT HER2 TUMOR MODEL

(75) Inventors: Sharon Erickson, Hillsborough, CA (US); Kathleen King, Pacifica, CA (US); Ralph Schwall, Pacifica, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 09/811,115

(22) Filed: Mar. 16, 2001

(65) Prior Publication Data

US 2002/0035736 A1 Mar. 21, 2002

Related U.S. Application Data

(60) Provisional application No. 60/189,844, filed on Mar. 16, 2000.

(51) Int. Cl.$^7$ .................. A01K 67/027; A01K 67/033; G01N 33/00; C12N 15/00; C12N 15/63

(52) U.S. Cl. ................. 800/18; 800/8; 800/9; 800/10; 800/3; 435/455; 435/463; 435/325; 435/320.1

(58) Field of Search ............................ 800/3, 18, 21, 800/22, 25, 8, 9, 10; 435/455, 463, 320.1, 325

(56) References Cited

U.S. PATENT DOCUMENTS

| | | | |
|---|---|---|---|
| 4,968,603 A | 11/1990 | Slamon et al. | 435/6 |
| 5,677,171 A | 10/1997 | Hudziak et al. | 435/240.27 |
| 5,783,186 A | 7/1998 | Arakawa et al. | 424/143.1 |
| 5,821,337 A | 10/1998 | Carter et al. | 530/387.3 |
| 5,824,311 A | 10/1998 | Green et al. | 424/138.1 |

FOREIGN PATENT DOCUMENTS

| | | |
|---|---|---|
| WO | WO 93/21319 | 10/1993 |
| WO | WO 94/00136 | 1/1994 |
| WO | WO 94/22478 | 10/1994 |
| WO | WO 97/04801 | 2/1997 |

OTHER PUBLICATIONS

DiGiovanna et. al.; Avtive signaling by Neu in transgenic mice, 1998, Oncogene 17: 1877–1844.*
Kappel et. al.; Regulating gene expression in Transgenic animals, 1992, Current Opinion in Biotechnology 3: 548–553.*
Mullins et. al.; Transgenesis in Nonmurine Spesies, 1993, Hypertension 22: 630–633.*
Houdebine; Production of pharmaceutical proteins from transgenic animals, 1994, Journal of Biotechnology 34: 269–287.*
Niemann; Transgenic farm animals get off the ground, 1998, Transgenic Research 7: 73–75.*
Kasprzyk et. al.; Therapy of an Animal Model of Human Gastric Cancer Using . . . Monoclonal Antibodies, 1992, Cancer Research 52: 2771–2776.*
Hancock et. al.; A Monoclonal Antibody against the c–erB–2 Protein Enhances the Cytotoxicity of . . . Tumor Cell Lines, 1991, Cancer Research 51: 4575–4580.*
Hudziak et. al.; Monoclonal Antibody Has Antiproliferative Effects In Vitro and Sensitizes Human Breast Tumor Cells to Tumor Necrosis Factor, 1989, Molecular and Cellular Biology: 1165–1172.*
Arteaga, C.L. et al., "p185$^{c-erbB-2}$ Signaling Enhances Cisplatin–induced Cytoxicity in Human Breast Carcinoma Cells: Association between an Oncogenic Receptor Tyrosine Kinase and Drug–induced DNA Repair," *Cancer Research*, vol. 54, pp. 3758–3765 (1994).
Bacus, S.S. et al., "Tumor–inhibitory Monoclonal Antibodies to the HER–2/Neu Receptor Induce Differentiation of Human Breast Cancer Cells," *Cancer Research*, vol. 52, pp. 2580–2589 (1992).
Fendly, B.M. et al., "Characterization of Murine Monoclonal Antibodies Reactive to Either the Human Epidermal Growth Factor Receptor or Her2/neu Gene Product," *Cancer Research*, vol. 50, pp. 1550–1558 (1990).
Hancock, M.C. et al., "A Monoclonal Antibody against the c–erB–2 Protein Enhances the Cytotoxicity of cis–Diamminedichloroplatinum against Human Breast and Ovarian Tumor Cell Lines," *Cancer Research*, vol. 51, pp. 4575–4580 (1991).
Hudziak, R.M. et al., "Increased expression of the putative growth factor receptor p185$^{HER2}$ causes transformation and tumorigenesis of NIH 3T3 cells," *Proc. Natl. Acad. Sci. USA*, vol. 84, pp. 7159–7163.
Kasprzyk, P.G. et al., "Therapy of an Animal Model of Human Gastric Cancer Using a Combination of Anti-–erbB–2 Monoclonal Antibodies," *Cancer Research*, vol. 52, pp. 2771–2776 (1992).
Kern, J.A. et al., "p185$^{neu}$ Expression in Human Lung Adenocarcinomas Predicts Shortened Survival," *Cancer Reasearch*, vol. 50, pp. 5184–5191 (1990).
King, C.R. et al., "Amplification of a Novel v–erbB–Related Gene in a Human Mammary Carcinoma," *Science*, vol. 229, pp. 974–976 (1985).
Kotts et al., *In Vitro*, vol. 26, No. 3, p. 59A (1990).
Lewis, G.D. et al., "Growth Regulation of Human Breast and Ovarian Tumor Cells by Heregulin: Evidence for the Requirement of ErbB2 as a Critical Component in Mediating Heregulin Responsiveness," *Cancer Research*, vol. 56, pp. 1457–1465 (1996).

(List continued on next page.)

*Primary Examiner*—Deborah Crouch
*Assistant Examiner*—Thalan N. Ton
(74) *Attorney, Agent, or Firm*—Ginger R. Dreger, Esq.; Heller Ehrman White & McAuliffe LLP

(57) ABSTRACT

The invention concerns HER2-transgenic non-human mammals, animal models for screening drug candidates for the treatment of diseases and disorders associated with the overexpression of HER2. In particular, the invention concerns animal models designed to test drug candidates for the treatment of HER2-overexpressing cancers, including breast cancer, that are not responding or poorly responding to current treatments.

37 Claims, 48 Drawing Sheets

OTHER PUBLICATIONS

Maier, L.A. et al., "Requirements for the Internalization of a Murine Monoclonal Antibody Directed against the HER–2/neu Gene Product c–erbB–2," *Cancer Research,* vol. 51, pp. 5361–5369 (1991).

Park, Joo–Bae et al., "Amplification, Overexpression, and Rearrangement of the erbB–2 Protooncogene in Primary Human Stomach Carcinomas," *Cancer Research,* vol. 49, pp. 6605–6609 (1989).

Sarup, J.C. et al., "Characterization of an Anti–p185$^{HER2}$ Monoclonal Antibody that Stimulates Receptor Function and Inhibits Tumor Cell Growth," *Growth Regulation,* vol. 1, pp. 72–82 (1991).

Semba, K. et al., "A v–erbB–related protooncogene, c–erbB–2, is distinct from the c–erbB–1/epidermal growth factor–receptor gene and is amplified in a human salivary gland adenocarcinoma," *Proc. Natl. Acad. Sci. USA,* vol. 82, pp. 6497–6501 (1985).

Shawver, L.K. et al., "Ligand–like Effects Induced by Anti–c–erbB–2 Antibodies Do Not Correlate with and Are Not Required for Growth Inhibition of Human Carcinoma Cells," *Cancer Research,* vol. 54, pp. 1367–1373 (1994).

Skrepnik, N. et al., "Effects of Anti–erbB–2 (HER–2/neu) Recombinant Oncotoxin AR209 on Human Non–Small Cell Lung Carcinoma Grown Orthotopically in Athymic Nude Mice," *Clinical Cancer Research,* vol. 2, pp. 1851–1857 (1996).

Vitetta, E.S. et al., "Monoclonal Antibodies as Agonists: An Expanded Role for Their Use in Cancer Therapy," *Cancer Research,* vol. 54, pp. 5301–5309.

Weiner, D.B. et al., "Expression of the neu Gene–encoded Protein (P185$^{neu}$) in Human Non–Small Cell Carcinomas of the Lung," *Cancer Research,* vol. 50, pp. 421–425 (1990).

Yamamoto, T. et al., "Similarity of protein encoded by the human c–erbB–2 gene to epidermal growth factor receptor," *Nature,* vol. 319, pp. 230–234 (1986).

Yokota, J. et al., "Amplification of c–erbB–2 Oncogene in Human Adenocarcinomas in Vivo," *The Lancet,* vol. 1, pp. 765–767 (1986).

Yonemura, Y. et al., "Evaluation of Immunoreactivity for erbB–2 Protein as a Marker of Poor Short Term Prognosis in Gastric Cancer," *Cancer Research,* vol. 51, pp. 1034–1038 (1991).

Aasland et al., "Expression of oncogenes in thyroid tumours: Coexpression of c–erbB2/neu and c–erbB," *Br. J. Cancer,* vol. 57, pp. 358–363 (1988).

Bacus et al., "Differentiation of Cultured Human Breast Cancer Cells (AU–565 and MCF–7) Associated With Loss of Cell Surface HER–2/neu Antigen," *Molecular Carcinogenesis,* vol. 3, pp. 350–362 (1990).

Borst et al., "Oncogene Alterations in Endometrial Carcinoma," *Gynecol. Oncol.,* vol. 38, pp. 364–366 (1990).

Carter et al., "Humanization of anti–p185$^{HER2}$ antibody for human cancer therapy," *Proc. Natl. Acad. Sci. USA,* vol. 89, pp. 4285–4289 (1992).

Cobleigh et al., "Multinational Study of the Efficacy and Safety of Humanized Anti–HER2 Monoclonal Antibody in Women Who Have HER2–Overexpressing Metastatic Breast Cancer That Has Progressed after Cehmotherapy for Metastatic Disease," *J. Clin. Oncol.,* vol. 17, pp. 2639–2648 (1999).

Cohen et al., "Expression pattern of the neu (NGL) gene–encoded growth factor receptor protein (p185$^{neu}$) in normal and transformed epithelial tissues of the digestive tract," *Oncogene,* vol. 4, pp. 81–88 (1989).

Drebin et al., "Monoclonal antibodies reactive with distinct domains of the neu oncogene–encoded p185 molecule exert synergistic anti–tumor effects in vivo," *Oncogene,* vol. 2, pp. 273–277 (1988).

Drebin et al., "Down–Modulation of an Oncogene Protein Product and Reversion of the Transformed Phenotype by Monoclonal Antibodies," *Cell,* vol. 41, pp. 695–706 (1985).

D'Souza et al., "Overexpression of ERBB2 in human mammary epithelial cells signals inhibition of transcription of the E–cadherin gene," *Proc. Natl. Acad. Sci. USA,* vol. 91, pp. 7202–7206 (1994).

Guérin et al., "Overexpression of Either c–myc or c–erbB–2/neu Proto–Oncogenes in Human Breast Carcinomas: Correlation with Poor Prognosis," *Oncogene Research,* vol. 3, pp. 21–31 (1988).

Gu et al., "Overexpression of her–2/neu in human prostate cancer and benign hyperplasia," *Cancer Letters,* vol. 99, pp. 185–189 (1996).

Harweth et al., "Monoclonal Antibodies against the Extracellulr Domain of the erbB–2 Receptor Function as Partial Ligand Agonists," *The Journal of Biological Chemistry,* vol. 267, No. 21, pp. 15160–15167 (1992).

Hudziak et al., "p185$^{HER2}$ Monoclonal Antibody Has Antiproliferative Effects In Vitro and Sensitizes Human Brest Tumor Cells to Tumor Necrosis Factor," *Molecular and Cellular Biology,* vol. 9, No. 3, pp. 1165–1172 (1989).

Klapper et al., "A subclass of tumor–inhibitory monoclonal antibodies to erbB–2/HER2 blocks crosstalk with growth factor receptors," *Oncogene,* vol. 14, pp. 2099–2109 (1997).

Kraus et al., "Isolation and characterization of ERBB3, a third member of the ERBB/epidermal grwoth factor receptor family: Evidence for overexpression in a subset of human mammary tumors," *Proc. Natl. Acad. Sci. USA,* vol. 86, pp. 9193–9197 (1989).

Kumar et al., "Regulation of Phosphorylation of the c–erbB–2/HER2 Gene Product by a Monoclonal Antibody and Serum Growth Factor(s) in Human Mammary Carcinoma Cells," *Molecular and Cellular Biology,* vol. 11, No. 2, pp. 979–986 (1991).

Lewis et al., "Differential responses of human tumor cell lines to anti–p$\equiv^{HER2}$ monoclonal antibodies," *Cancer Immunol. Immunother.,* vol. 37, pp. 255–263 (1993).

McCann et al., "c–erbB–2 Oncoprotein Expression in Primary Human Tumors," *Cancer,* vol. 65, pp. 88–92 (1990).

McKenzie et al., "Generation and characterization of monoclonal antibodies specific for the human neu oncogene product, p185," *Oncogene,* vol. 4, pp. 543–548 (1989).

Myers et al., "Biological Effects of Monoclonal Antireceptor Antibodies Reactive with neu Oncogene Product, p185$^{neu}$," *Methods in enzymology,* vol. 198, pp. 277–290 (1991).

Pietras et al., "Antibody to HER–2/neu receptor blocks DNA repair after cisplatin in human breast and ovarian cancer cells," *Oncogene,* vol. 9, pp. 1829–1838 (1994).

Ross et al., "Prognostic Significance of HER–2/neu Gene Amplification Status by Fluorescence In Situ Hybridization of Prostate Carcinoma," *Cancer,* vol. 79, pp. 2162–2170 (1997).

Ross et al., "HER–2/neu Gene Amplification Status in Prostate Cancer by Fluorescense In Situ Hybridization," *Human Pathology,* vol. 28, No. 7, pp. 827–833 (1997).

Sadasivan et al., "Overexpression of HER–2/NEU May be an Indicator of Poor Prognosis in Prostate Cancer," *The Journal of Urology,* vol. 150, pp. 126–131 (1993).

Schaefer et al., "γ–Heregulin: a novel heregulin isoform that is an autocrine growth factor for the human breast cancer cell line, MDA–MB–175," *Oncogene,* vol. 15, pp. 1385–1394 (1997).

Scott et al., "p185$^{HER2}$ Signal Transduction in Breast Cancer Cells," *The Journal of Biological Chemistry,* vol. 266, No. 22, pp. 14300–14305 (1991).

Shepard et al., "Monoclonal Antibody Therapy of Human Cancer: Taking the HER2 Protooncogene to the Clinic," *Journal of clinical Immunology,* vol. 11, No. 3 (1991).

Slamon et al., "Human Breast Cancer: Correlation of Relapse and Survival with Amplification of the HER–2/neu Oncogene," *Science,* vol. 235, pp. 177–182 (1987).

Slamon et al., "Studies of the HER–2/neu Proto–oncogene in Human Breast and Ovarian Cancer," *Science,* vol. 244, pp. 707–712 (1989).

Sliwkowski et al., "Coexpression of erbB2 and erbB3 Proteins Reconstitutes a High Affinity Receptor for Heregulin," *The Journal of Biological Chemistry,* vol. 269, No. 20, pp. 14661–14665 (1994).

Stancovski et al., "Mechanistic aspects of the opposing effects of monoclonl antibodies to the ERBB2 receptor on tumor growth," *Proc. Natl. Acad. Sci. USA,* vol. 88, pp. 8691–8695 (1991).

Tagliabue et al., "Selection of Monoclonal Antibodies Which Induce Internalization and Phsophorylation of p185$^{HER2}$ and Growth Inhibition of Cells with HER2/NEU Gene Amplification," *Int. J. Cancer,* vol. 47, pp. 933–937 (1991).

Williams et al., "Expression of c–erb–2 in Human Pancreatic Adenocarcinomas," *Pathobiology,* vol. 59, pp. 46–52 (1991).

Xu et al., "Antibody–Induced Growth Inhibition is Mediated Through Immunochemically and Functionally Distinct Epitopes on the Extracellular Domain of the c–erbB–2 (HER–2/neu) Gene Product," vol. 53, pp. 401–408 (1993).

Zhau et al., "Amplification and Expression of the c–erb B–2/neu Proto–Oncogene in Human Bladder Cancer," *Molecular Carcinogenesis,* vol. 3, pp. 254–257 (1990).

King et al., "Amplification of a Novel v–erbB–Related Gene in a Human Mammary Carcinoma," *Science,* vol. 229, pp. 974–976 (1985).

Fukushige et al., "Localization of a Novel v–erbB–Related Gene, c–erbB–2, on Human Chromosome 17 and Its Amplification in a Gastric Cancer Cell Line," *Molecular and Cellular Biology,* vol. 6, No. 3, pp. 955–958 (1986).

Wall; Transgenic Livestock: Progress and Prospects for the Future, 1996, Theriogenology 45: 57–68.*

Mullins et. al; Perspective Series: Molecular Medicine in Genetically Engineered Animals, 1996, J. Clin. Invesyt., vol. 97:1557–1560.*

Cameron; Recent Advances in Transgenic Technology, 1997, Molecular Biotechnology, vol. 7: 253–265.*

Sigmund; Viewpoint: Are Studies in Genetically Altered Mice Out of Control?, 2000, Arterioscler Thromb Vasc. Biol. 20: 1425–1429.*

* cited by examiner

```
                                                       rmaI
            hgiAI/aspHI           sau3AI     maeI
   sau3AI                         mboI/ndeII
   mboI/ndeII      tru9I          dpnII   nheI        nlaIII   tseI              rmaI
   dpnII  bsp1286                 dpnI  cac8I  tseI          sphI   fnu4HI/bsoFI  maeI
   pvuI/bspCI      mseI           nlaIII  thaI  cac8I               nspHI   bbvI bfaI
   mcrI   bsiHKAI  tsp509I        fnuDII/mvnI   cac8I         nspI         scfI  styI
   bsiEI  bmyI  aseI/asnI/vspI  bstUI  bfaI   aluI  nspI      pstI               bsaJI
   taqI   apaLI/snoI  rcaI    bsh1236I  fnu4HI/bsoFI   cac8I  bsgI               blnI
   aluI   dpnI  alw44I/snoI  bspHI  nruI  aluI bbvI   cac8I                      avrII
                                                     avaI
 1 AAGCTCGATC GGTGCACATT AATTCATGAT CGGAGCTAG CAGCTTGCAT GCCTGCAGCA GAAATGGTTG AACTCCCGAG AGTGTCCTAC ACCTAGGGGA
   TTCGAGCTAG CCACGTGTAA TTAAGTACTA GCCTCGATC GTCGAACGTA CGGACGTCGT CTTTACCAAC TTGAGGGCTC TCACAGGATG TGGATCCCCT
   ^start of linker 1                                                       ^end of linker 1
                                                   ^start of MMTV promoter hgiJII
      styI                                bsp1286
      bsaJI                   hinPI       bmyI
   tseI                       hhaI/cfoI   banII                                              tseI
   fnu4HI/bsoFI               mstI                                                           fnu4HI/bsoFI
   bbvI           styI  bcgI  aviII/fspI  fokI                                               bbvI
                  bsaJI  ahdI/eamll05I    bstF5I
101 GAAGCAGCCA AGGGGTTGTT TCCCACCAAG GACGACCCGT CTGCGCACAA ACGGATGAGC CCATCAGACA AAGACATATT CATTCTCTGC TGCAAACTTG
   CTTCGTCGGT TCCCCAACAA AGGGTGGTTC CTGCTGGGCA GACGCGTGTT TGCCTACTCG GGTAGTCTGT TTCTGTATAA GTAAGAGACG ACGTTTGAAC mwoI
                                       cac8I   hgiJII
                                       hgiAI/aspHI
                                       bsp1286   bsp1286
                              mwoI     bsiHKAI   bmyI             pleI   tru9I  sapI      mamI
                              aciI     bmyI     banII hphI        hinfI  mseI aluI        bsaBI
                                                                         mboII   earI/ksp632I
201 GCATAGCTCT GCTTTGCTGG GGCATTGGGG GAAGTTGCGG TTCGTGCTCG CAGGGCTCTC ACCCTTGACT CTTTTAATAG CTCTTCTGTG CAAGATTACA
   CGTATCGAGA CGAAACGACC CCGTAACCCC CTTCAACGCC AAGCACGAGC GTCCCGAGAG TGGGAACTGA GAAAATTATC GAGAAGACAC GTTCTAATGT
```

FIG. 1A

```
                                                                    claI/bsp106
                                                                       bspDI
                                                                       sfaNI
                              mnlI       sau96I                        aciI taqI                              rsaI
                              ddeI       avaII                         fnu4HI/bsoFI                           csp6I
              mnlI    bsu36I/mstII/sauI         mnlI                                     tru9I    tfiI        scaI
         tsp509I   taqI    mnlI                                                          mseI    hinfI
301 ATCTAAACAA TTCGGAGAAC TCGACCTTCC TCTCCTGAGG CAAGGACCAC AGCCAACTTC CTCTTACAAG CCGCATGAT TTTGTCCTTC AGAAATAGAA
    TAGATTTGTT AAGCCTCTTG AGCTGGAAGG AGAGGACTCC GTTCCTGGTG TCGGTTGAAG GAGAATGTTC GGCGTAGCTA AACAGGAAG TCTTTATCTT
         bsmI    tsp509I
         cac8I
                                                               hgaI                      maeIII
401 ATAAGAATGC TTGCTAAAAA TTATATTTTT ACCAATATAAGA CCAATCCAAT AGGTAGATTA TTAGTTACTA TGTTAAGAAA TGAATCATTA TCTTTTAGTA
    TATTCTTACG AACGATTTTT AATATAAAAA TGGTTATTCT GGTTAGGTTA TCCATCTAAT AATCAATGAT ACAATTCTTT ACTTAGTAAT AGAAAATCAT
              tsp509I                                           hgaI                                             haeIII/p
              apoI                                              esp3I      tsp509I                                stuI
                                                                bsmBI      munI/mfeI                              haeI
                                                                bsmAI     mnlI mboII
501 CTATTTTTAC TCAAATTCAG AAGTTAGAAA TGGGAATAGA AAATAGAAAG AGACGCTCAA CCTCAATTGA AGAACAGGTG CAAGGACTAT TGACCACAGG
    GATAAAAATG AGTTTAAGTC TTCAATCTTT ACCCTTATCT TTTATCTTTC TCTGCGAGTT GGAGTTAACT TCTTGTCCAC GTTCCTGATA ACTGGTGTCC
                                                                              bsmFI
                                                                              scrFI        sau96I
         rmaI                                                                 mvaI         avaII
         maeI                                                                 ecoRII       asuI
         bfaI                                            bsmAI                dsaV         ppuMI
                                                                              bstNI        nlaIV
                                                                              bssKI        ecoO109I/draII
                                                                              bsaJI        bsmFI     scfI
601 CCTAGAAGTA AAAAAGGGAA TTTTGTCAAA ATAGGAGACA GGTGGTGGCA ACCAGGGACT TATAGGGGAC CTTACATCTA CAGACCAACA
    GGATCTTCAT TTTTTCCCTT AAAACAGTTT TATCCTCTGT CCACCACCGT TGGTCCCTGA ATATCCCCTG GAATGTAGAT GTCTGGTTGT
                                                                                                         mnlI
                                                                                                         sau3AI
                                                                                                         mboI/ndeII
                                 tsp509I                                                                 dpnII
                                 tru9I                                                                   dpnI
                                 mseI                        maeIII                                      alwI
         sfaNI   bslI      mboII                                                                         bstYI/xhoII
701 GATGCCCCCT TACCATATAC AGGAAGATAT GACTTAAAAT GGTTACAGTC AATGGCTATA AAGTGTTATA TAGATCCCTC CCTTTTCGTG
    CTACGGGGGA ATGGTATATG TCCTTCTATA CTGAATTTAA CCAATGTCAG TTACCGATAT TTCACAATAT ATCTAGGGAG GGAAAAGCAC
```

```
                                                                                       bsmAI
                                                                                       esp3I
                                                                         fokI bsmBI bsrBI tsp45I
                                                                         bstF5I     aciI  maeIII
                                     mnlI                     CCATCCCGTC TCCGCTCGTC
                                     hphI
201 AAGATATAAA AGAGTGCTGA TTTTTTGAGT AAACTTGCAA CAGTCCTAAC ATTCACCTCT TGTGTGTTTG TGTCTGTTCG CCATCCCGTC TCCGCTCGTC
    TTCTATATTT TCTCACGACT AAAAAACTCA TTTGAACGTT GTCAGGATTG TAAGTGGAGA ACACACAAAC ACAGACAAGC GGTAGGGCAG AGCGAGCAG fnu4HI/bsoFI
                                       sau3AI                                 haeIII/palI
                 sau96I                  alwI                                 mcrI
                  nlaIV                mspI       cac8I        bcgI          eagI/xmaIII/eclXI
                  avaII                hpaII    rmaI    tfiI                 eaeI
                  asuI                 scrFI    maeI    hinfI                         fnu4HI/bsoFI
                  sanDI                nciI  mboI/ndeII thaI claI/bsp106   notI
                  ppuMI                dsaV dpnII aluI fnuDII/mvnI         fnu4HI/bsoFI  scfI
                  nlaIV                     cauII  nheI  bstUI taqI        cac8I cfrI tru9I
                  eco0109I/draII                  bssKI  cac8I  bsh1236I   aluI aciI aciI  pstI
                      mnlI bsmFI aciI  bsaJI dpnI bfaI  nruI bspDI hindIII bsiEI mseI bsgI             mnlI
301 ACTTATCCTT CACTTTCCAG AGGGTCCCCC CGCAGACCCC GGATCGCTAG CTCGCGAATC GATAAGCTTG CGGCCGCTTA ACTGCAGAAG TTGGTCGTGA
    TGAATAGGAA GTGAAAGGTC TCCCAGGGGG GCGTCTGGGG CCTAGCGATC GAGCGCTTAG CTATTCGAAC GCCGGCGAAT TGACGTCTTC AACCAGCACT
                                                         ^start of BS intron insert at ClaI
                                                          ^bp820 in pCI
                                                          ^start of BS insert at HindIII pleI
                                                                                    hinfI                nlaIV
                                                                                    mboI                 hgiCI
                                                                   bsmAI            bpuAI                banI
           tru9I bsmAI                                             taqI             bbsI
    bsrI   mseI bsaI                       bsrI
    tspRI bspMI  maeIII
401 GGCACTGGGC AGTAAGTAT CAAGGTTACA AGACAGGTTT AAGGAGACCA ATAGAAACTG GCTTGTCGA GACAGAGAAG ACTCTTGCGT TTCTGATAGG
    CCGTGACCCG TCATTCATA GTTCCAATGT TCTGTCCAAA TTCCTCTGGT TATCTTTGAC CGAACAGCT CTGTCTCTTC TGAGAACGCA AAGACTATCC
     ^start of chimeric intron at pCI 857
```

```
                                                            haeIII/palI
                                                              eaeI
                                                              cfrI
                                                              scrFI
                                                              mvaI
                                                              ecoRII
                                                              dsaV
                                                              bstNI
                                          nlaIV               bssKI                  rmaI
                                          hgiCI               apyI                   maeI     bsmAI mspAII/nspBII
                                          banI                bsaJI                  bfaI     bsaI  aciI
         bsmFI             alwNI
         sau96I            alw26I/bsmAI
         nlaIV             mwoI
         avaII             bstAPI
         asuI     scfI              mwoI
         ppuMI    pstI    tseI
         bspMI    bsgI    fnu4HI/bsoFI
                  tspRI   bbvI
         mnlI ecoO109I/draII mnlI aciI          alnI           mnlI
001 GTGAGGCAGG TCCCACTGCA GAGGCTGCGG ATTGTGCGAG GCACCCAGCT CTTTGAGGAC AACTATGCCC TGGCCGTGCT AGACAATGGA GACCCGCTGA
    CACTCCGTCC AGGGTGACGT CTCCGACGCC TAACACGCTC CGTGGGTCGA GAAACTCCTG TTGATACGGG ACCGGCACGA TCTGTTACCT CTGGGCGACT
 91  V  R  Q  V  P  L  Q   R  L  R   I  V  R  G   T  Q  L   F  E  D   N  Y  A  L   A  V  L   D  N  G   D  P  L  N tseI
                                           fnu4HI/bsoFI
                               scrFI       bbvI
                               mvaI        scfI     taqI
                               ecoRII      pstI     sfuI                                       mspAII/nspB
                               dsaV        bsgI     bstBI                           sau3AI
                       mnlI    bstNI       cac8I    bsiCI                           mboI/ndeII
               haeIII/palI     bssKI       haeIII/palI tseI                         dpnII
       tsp45I  sau96I  asuI    apyI   stuI           fnu4HI/bsoFI                   dpnI      nlaIV
       maeIII  asuI    nlaIV   bsaJI  mnlI   mwoI    bbvI       asuII   bstYI/xhoI  alwI      aciI
       ecoNI   nlaIV   bsaJI/draII haeI  aciI alnI   alnI       mnlI    bglII  mnlI TGATCCAGCG
       bslI    ecoO109I/draII
101 ACAATACCAC CCCTGTCACA GGGGCCTCCC CAGGAGGCCT GCGGGAGCTG CAGCTTCGAA GCCTCACAGA GATCTTGAAA GGAGGGGTCT TGATCCAGCG
    TGTTATGGTG GGGACAGTGT CCCCGGAGGG GTCCTCCGGA CGCCCTCGAC GTCGAAGCTT CGGAGTGTCT CTAGAACTTT CCTCCCCAGA ACTAGGTCGC
125 N  T  T  P  V  T   G  A  S  P   G  G  G  L   R  E  L   Q  L  R  S   L  T  E   I  L  K   G  G  V  L   I  Q  R scrFI
                   mvaI
                   ecoRII
                   dsaV                                      cac8I                               haeIII/
                   bstNI                                     aluI                                sau96I
                   bssKI                                     pvuII                    bsrBI     asuI
          aluI     apyI                             mboII    mspAII/nspBII tspRI      bslI       avaI
201 GAACCCCCAG CTCTGCTACC AGGACACGAT TTTGTGAAAG GACATCTTCC ACAAGAACAA CCAGCTGGCT CTCACACTGA TAGACACCAA CCGCTCTCGG
    CTTGGGGGTC GAGACGATGG TCCTGTGCTA AAACACTTTC CTGTAGAAGG TGTTCTTGTT GGTCGACCGA GAGTGTGACT ATCTGTGGTT GGCGAGAGCC
158 N  P  Q  L  C  Y  Q   D  T  I   L  W  K  D   I  F  H   K  N  N   Q  L  A   L  T  L  I   D  T  N   R  S  R
```

*FIG. 1G*

```
                                                                    hinPI
                                                                    hhaI/cfoI
                                      mspAII/nspBII                 thaI
                                mwoI tseI                           fnuDII/mvnI
                                nlaIV fnu4HI/bsoFI                  bstUI
                                hgiJII bslI              mnlI    mwoI bsh1236I        mspI
                                bsp1286 bbvI             ddeI    alwNI hgaI           hpaII mwoI
                                bmyI aciI                alw26I/bsmAI tspRI           cfr10I/bsrFI
        cac8I                   banII bslI               GATTGTCAGA GCCTGACGCG CACTGTCTGT GCCGGTGGCT
301 GCCTGCCACC CCTGTTCTCC GATGTGTAAG GGCTCCCGCT GCTGGGGAGA GAGTTCTGAG CTAACAGTCT CGGACTGCGC GTGACAGACA CGGCCACCGA
    CGGACGGTGG GGACAAGAGG CTACACATTC CCGAGGGCGA CGACCCCTCT CTCAAGACTC CTAACAGTCT CGGACTGCGC GTGACAGACA CGGCCACCGA
191 A   C  H   P   C   S   P   M   C   K   G   S   R   C   W   G   E   S   S   E   D   C   Q   S   L   T   R   T   V   C   A   G   G   C sau96I
                                                          nlaIV
                                                          haeIII/palI
                                                          sau96I                              haeIII/palI
                                                          pspOMI/bsp120I                      haeI
                                                tseI      nlaIV                               scrFI
                                                mwoI      hgiJII                              mvaI
                                                mspI      ecoO109I/draII                      ecoRII
                                                hpaII     bsp1286                             dsaV
                                                naeI/ngoMI bmyI                               bstNI
                                                cfr10I/bsrFI asuI                             bssKI
        tseI                                    cac8I     banII                               apyI
        fnu4HI/bsoFI                            tseI      fnu4HI/bsoFI                        mwoI cac8I mnlI
        mspAII/nspBII      tspRI                fnu4HI/bsoFI asuI                             CCTGCCTCCA
        bslI       haeIII/palI                  bbvI      bbvI   apaI         CAAGCACTCT GACTGCCTGG GGACGGAGGT
        aciI       sau96I                       tseI nlaIII tspRI                 CGTGCCCGGG GTTCGTGAGA CTGACGGACC
        bsp1286    asuI
        bmyI bbvI  nlaIV        tspRI
401 GTGCCCGCTG CAAGGGGCCA CTGCCCACTG ACTGCTGCCA TGAGCAGTGT GCTGCCGGCT GCACGGGCCC CAAGCACTCT GACTGCCTGG CCTGCCTCCA
    CACGGGCGAC GTTCCCCGGT GACGGGTGAC TGACGACGGT ACTCGTCACA CGACGGCCGA CGTGCCCGGG GTTCGTGAGA CTGACGGACC GGACGGAGGT
225 A   R   C   K   G   P   L   P   T   D   C   C   H   E   Q   C   A   A   G   C   T   G   P   K   H   S   D   C   L   A   C   L   H
```

FIG. 1H

```
                                                                    bstEII
                                                                    scrFI
                                                                    mvaI                                                                        bst217I
                                                                    ecoRII                                                                      mspI
                                                                    dsaV                                                                        sau96I bst1107I
                                              tseI                  bstNI                                              taiI                     mnlI hpaII
                                              fnu4HI/bsoFI          bssKI hphI                                         maeII pleI               bslI haeIII/palI
                                              bbvI            apyI tsp45I                                         aflIII hinfI nlaIII           bsaJI cfr10I/bsrFI
              tspRI sfaNI                alu1 tspRI bslI bsaJI maeIII                                                                           avaI asuI       accI 2501 CTTCAACCAC AGTGGCATCT GTGAGCTGCA CTGCCCAGCC CTGGTCACCT ACAACACAGA CACGTTGAG TCCATGCCCA ATCCCGAGGG CCGGTATACA
     GAAGTTGGTG TCACCGTAGA CACTCGACGT GACGGGTCGG GACCAGTGGA TGTTGTGTCT GTGCAACTC AGGTACGGGT TAGGGCTCCC GGCCATATGT
258    F  N  H    S  G  I    C  E  L  H    C  P  A  L    V  T  Y    N  T  D    T  F  E  S    M  P  N    P  E  G    R  Y  T cac8I
         hinPI
         hhaI/cfoI
         nlaIV
         narI
         kasI
         hinII/acyI
         hgiCI
         haeII aluI         ahdI/eam1105I                                    sau3AI
         eheI pvuII     tsp45I                                               mboI/ndeII
         banI mspAII/nspBII                                                  dpnII                                                          tsp45I
         ahaII/bsaHI    maeIII              bsmFI                            dpnI                                                           maeIII
                                                                             alwI                                                           hphI
                                                                             nlaIV                                                          mnlI
                                                                             bstYI/xhoII
                                                                     bslI    taiI bamHI
                                                                             maeII alwI            mnlI
2601 TTCGGCGCCA GCTGTGTGAC TGCCTGTCCC TACAACTACC TTTCTACGGA CGTGGGATCC TGCACCCTCG TCTGCCCCCT GCACAACCAA GAGGTGACAG
     AAGCCGCGGT CGACACACTG ACGGACAGGG ATGTTGATGG AAAGATGCCT GCACCCTAGG ACGTGGGAGC AGACGGGGGA CGTGTTGGTT CTCCACTGTC
291    F  G  A    S  C  V    T  A  C  P    Y  N  Y  L    S  T  D    V  G  S    C  T  L  V    C  P  L    H  N  Q    E  V  T  A hgiAI/aspHI
                                                                                                       bsp1286
         fokI         aciI          cac8I                                                              bsiHKAI
         bstF5I       mspAII/nspBII tseI     avaI                                                      bmyI            hphI            bsrI
         mnlI     msII              fnu4HI/bsoFI bsp1286                                               nlaIII          mnlI mnlI        maeIII
                                    bbvI     bmyI
2701 CAGAGGATGG AACACAGCGG TGTGAGAAGT GCAGCCAAGCC CTGTGCCCGA GTGTGCTATG GTCTGGGCAT GGAGCACTTG CGAGAGGTGA GGGCAGTTAC
     GTCTCCTACC TTGTGTCGCC ACACTCTTCA CGTCGGTTCGG GACACGGGCT CACACGATAC CAGACCCGTA CCTCGTGAAC GCTCTCCACT CCCGTCAATG
325    E  D  G    T  Q  R    C  E  K  C    S  K  P    C  A  R    V  C  Y  G    L  G  M    E  H  L    R  E  V  R    A  V  T

FIG. 1I
```

```
                                                                                      sau96I
                                                                                      nlaIV
                                                              sau3AI      scrFI       avaII
                                                              mboI/ndeII  mvaI        asuI
                                                              dpnII       ecoRII      sanDI
                                                              dpnI        dsaV        ppuMI
                                        tseI       bstYI/xhoII            bstNI       nlaIV
                                        fnu4HI/bsoFI                      bssKI       ecoO109I/draII
                                        bbvI       bglII                  apyI        mspI    hpaII alul     bsmFI   mnlI       tspRI
            xcmI         cac8I          mboI       nlaIV
            scrFI    apyI
            mvaI
            ecoRII
            dsaV
            bstNI
            bssKI
      tspRI apyI
801 CAGTGCCAAT ATCCAGGAGT TTGCTGGCTG CAAGAAGATC TTTGGGAGCC TGGCATTTCT GCCGGAGAGC TTTGATGGGG ACCCAGCCTC CAACACTGCC
    GTCACGGTTA TAGGTCCTCA AACGACCGAC GTTCTTCTAG AAACCCTCGG ACCGTAAAGA CGGCCTCTCG AAACTACCCC TGGGTCGGAG GTTGTGACGG
358 S   A   N   I   Q   E   F   A   G   C   K   K   I   F   G   S   L   A   F   L   P   E   S   F   D   G   D   P   A   S   N   T   A mspI
                                                                        hpaII
                                   sau3AI                               haeIII/paII
                                   mboI/ndeII                           eaeI               ddeI    bpuAI
           aluI            pleI    dpnII                                cfrI               mnlI    bbsI
    bpmI/gsuI    tseI      hinfI   mboII dpnI         maeIII            nlaIII   cac8I     drdI    hgaI
    bsrBI        fnu4HI/bsoFI      earI/ksp632I       bstEII      ddeI
    aciI   mwoI   bbvI    bsmAI
901 CCGCTCCAGC CAGAGCAGCT CCAAGTGTTT GAGACTCTGG AAGAGATCAC AGTTACCTA TACATCTCAG CATGGCCGGA CAGCCTCGCC GACCTCAGCG
    GGCGAGGTCG GTCTCGTCGA GGTTCACAAA CTCTGAGACC TTCTCTAGTG TCCAATGGAT ATGTAGAGTC GTACCGGCCT GTCGACGGA CTGGAGTCGC
391 P   L   Q   P   E   Q   L   Q   V   F   E   T   L   E   E   I   T   G   Y   L   Y   I   S   A   W   P   D   S   L   P   D   L   S   V hinPI
                                hhaI/cfoI
                                nlaIV
                                narI
               bsmFI             kasI
               scrFI             hinlI/acyI                                                          hinPI
               nciI              hgiCI                                                               hhaI/cfoI
               mspI              haeII                                         cac8I
               hpaII             eheI                                          pvuII
    alwNI      dsaV              banI                                          mspAII/nspBII        fnu4HI/bsoFI
    alw26I/bsmAI cauII tsp509I   ahaII/bsaHI mwoI bslI                         sfaNI aluI mwoI      bbvI       tspRI
    mboII bspMI bssKI  ecoRI
001 TCTTCCAGAA CCTGCAAGTA ATCGGGGAC GAATTCTGCA CAATGGCGCC TACTGCTGA CCCTGCAAGG GCTGGGCATC AGCTGGCTGG GGCTGGCCTC
    AGAAGGTCTT GGACGTTCAT TAGCCCCCTG CTTAAGACGT GTTACCGCGG ATGACGACT GGGACGTTCC CGACCCGTAG TCGACCGACC CCGACGGAG
425 F   Q   N   L   Q   V   I   R   G   R   I   L   H   N   G   A   Y   S   L   T   L   Q   G   L   G   I   S   W   L   G   L   R   S
```

```
                                                scrFI
                                                mvaI
                                                ecoRII
                                                dsaV
                                                bstNI
                                                bssKI
                                                apyI                                            taiI
                                        sau96I                 tseI                             maeII        esp3I
                                        avaII fokI             fnu4HI/bsoFI                     hinlI/acyI bsmAI
                            msII        asuI bstF5I            bbvI  aciI          cac8I mnlI   ahaII/bsaHI  bsmBI  aciI 3601 AGCCTTGCCC CATCAACTGC ACCCACTCCT GTGTGGACCT GGATGACAAG GGCTGCCCCG CCGAGCAGAG AGCCAGCCCT CTGACGTCCA TCGTCTCTGC
     TCGGAACGGG GTAGTTGACG TGGGTGAGGA CACACCTGGA CCTACTGTTC CCGACGGGGC GGCTCGTCTC TCGGTCGGGA GACTGCAGGT AGCAGAGACG
625    P  A  C   H  Q  L   T  H  S  C   V  D  L   D  D  K   G  C  P  A   E  Q  R    A  S  P    L  T  S  I   V  S  A mspI
                                                                                    mroI
                                                       mnlI                         bspMII
                                                       sau3AI                       bspEI
                                                       mboI/ndeII                   bsaWI
                                                       mamI                         sau3AI
                                                       dpnII                        mboI/ndeII
                                                       dpnI                         dpnII
                                                       bsaBI                        dpnI
                                                       alwI                         alwI
                                                       nlaIV
                                                       bstYI/xhoII        tseI      bstYI/xhoII        mwoI   tseI
                                                       bamHI              fnu4HI/bsoFI  hpaII  rsaI    aciI   fnu4HI/
                                          bsmI         alwI     mwoI      bbvI  mboII accIII  csp6I sfaNI bsmAI bbvI 3701 GGTGGTTGGC ATTCTGCTGG TCGTGGTCTT GGGGGTGGTC TTTGGGATCC TCATCAAGCG ACGGCAGCAG AAGATCCGGA AGTACACGAT GCGGAGACTG
     CCACCAACCG TAAGACGACC AGCACCAGAA CCCCCACCAG AAACCCTAGG AGTAGTTCGC TGCCGTCGTC TTCTAGGCCT TCATGTGCTA CGCCTCTGAC
658    V  V  G   I  L  L   V  V  V  L   G  V  V   F  G  I   L  I  K  R    R  Q  Q    K  I  R    K  Y  T  M   R  R  L
```

```
                                                          sau3AI
                                                          mboI/ndeII
                                             hinPI        dpnII
                                             hhaI/cfoI    nlaIV
                                    scrFI                 bstYI/xhoII
                                    mvaI                  bamHI
                                    ecoRII                aciI
                                    dsaV
                    mspAII/nspBII   bstNI     sfaNI dpnI              esp3I     mnlI
        rmaI        aciI   maeI     bssKI     mamI alwI               bsmBI     ddeI
    mwoI            fnu4HI/bsoFI aciI         apyI   bsaBI alwI       bsmAI     aluI    hphI
 pstI               nlaIV bfaI      sfaNI
 scfI  bsgI   aluI
 801 CTGCAGGAAA CGGAGCTGGT GGAGCCGCTG ACACCAGGCC GAGCGATGCC CAACCAGGCG CAGATGCGGA TCCTGAAAGA GACGGAGCTG AGGAAGGTGA
     GACGTCCTTT GCCTCGACCA CCTCGGCGAC TGTGGTCCGG CTCGCTACGG GTTGGTCCGC GTCTACGCCT AGGACTTCT  CTGCCTCGAC TCCTTCCACT
 691  L  Q  E  T  E  L  V  E  P  L  T  P  S  G  A  M  P  N  Q  A  Q  M  R  I  L  K  E  T  E  L  R  K  V  R bslI
                                          sau3AI
                                          mboI/ndeII
                                          dpnII                                           mscI/balI
                                          dpnI                                            haeI
                     sau3AI mwoI          alwI                                            eaeI
                     mboI/ndeII           nlaIV                              tspRI
                     dpnII hinPI          bstYI/xhoII                        tsp509I cfrI mslI
                     dpnI hhaI/cfoI       bamHI                              apoI bsrI haeIII/palI         mnlI
                     bstYI/xhoII          alwI          sfaNI
                     alwI  haeII  accI                                       AATTCCAGTG GCCATCAAAG TGTTGAGGGA
 901 AGGTGCTTGG ATCTGGCGCT TTTGGCACAG TCTACAAGGG CATCTGGATC CCTGATGGGG AGAATGTGAA AATTCCAGTG GCCATCAAAG TGTTGAGGGA
     TCCACGAACC TAGACCGCGA AAACCGTGTC AGATGTTCCC GTAGACCTAG GGACTACCCC TCTTACACTT TTAAGGTCAC CGTAGTTTC  ACAACTCCCT
 725  V  L  G  S  G  A  F  G  T  V  Y  K  G  I  W  I  P  D  G  E  N  V  K  I  P  V  A  I  K  V  L  R  E nlaIV
                                                              hgiJII                       mwoI
                                        taiI                  bsp1286                      bslI
                                        maeII                 bmyI                         aciI
                              ddeI      bsaAI                 banII  ndeI bsmAI  bglI      sfaNI
 foKI
 bstF5I
 001 AAACACATCC CCCAAAGCCA ACAAAGAAAT CTTAGACGAA GCATACGTGA TGGCTGGTGT GGCTCCCCA TATGTCTCCC GCCTTCTGGG CATCTGCCTG
     TTTGTGTAGG GGGTTTCGGT TGTTTCTTTA GAATCTGCTT CGTATGCACT ACCGACCACA CCGAGGGGT ATACAGAGG CGGAAGACCC GTAGACGGAC
 758  N  T  S  P  K  A  N  K  E  I  L  D  E  A  Y  V  M  A  G  V  G  S  P  Y  V  S  R  L  L  G  I  C  L
```

FIG. 10

```
                                                                               haeIII/palI
                                                                               sau96I
                              mspI                                             asuI
                              hpaII                              tsp45I        nlaIV    bslI
                              naeI/ngoMI                         maeIII        aluI    AAACCTTACG
                              cfr10I/bsrFI
                              cac8I
            pleI              sgrAI
            hinfI             aciI aciI hphI  msII
            bpmI/gsuI                                                                                                                                                  
      4401  CTGGAGTCCA TTCTCCGCCG GCGGTTCACC CACCAGAGTG ATGTGTGGAG TTATGGTGTG ACTGTGTGGG AGCTGATGAC TTTTGGGGCC AAAACCCCGG TTTGGAATGC
            GACCTCAGGT AAGAGGCGGC CGCCAAGTGG GTGGTCTCAC TACACACCTC AATACCACAC TGACACACCC TCGACTACTG AAAACCCCGG AAACCCCTTAC G
      891   L   E    S   I    L   R   R    R   F   T    H   Q   S   D    V   W   S    Y   G   V    T   V   W   E    L   M   T    F   G   A    K   P   Y   D scrFI
                     nciI
                     mspI
                     hpaII
                     dsaV
                     cauII
                     bssKI
                     xmaI/pspAI
              bslI   smaI
              sau3AI scrFI
              mboI/ndeII
              dpnII  nciI                            tseI              sau3AI
              dpnI   dsaV  sau3AI                    mwoI              mboI/ndeII
              alwI   cauII mboI/ndeII                fnu4HI/bsoFI      dpnII
              nlaIV  bssKI dpnII                     bbvI              dpnI
              bstYI/xhoII  dpnI                      fnu4HI/bsoFI      bcII
              bamHI  bsaJI alwI    bspMI             aciI              nlaIII
              alwI   avaI  bstYI/xhoII    bsrBI                        accI msII   nlaIII
      4501  ATGGGATCCC AGCCCGGGAG ATCCCTGACC TGCTGGAAAA GGGGAGCGG CTGCCCCAGC CCCCCATCTG CACCATTGAT GTCTACATGA TCATGGTCAA
            TACCCTAGGG TCGGGCCCTC TAGGGACTGG ACGACCTTTT CCCCCTCGCC GACGGGGTCG GGGGGTAGAC GTGGTAACTA CAGATGTACT AGTACCAGTT
      925   G   I    P    A   R   E    I   P    D    L   L   E   K    G   E    R    L   P   Q    P    P    I   C    T    I    D    V   Y   M    I   M   V   K
```

```
                                                       sau96I
                                                       nlaIV
                                                       avaII
                                                       asuI
                                 rsaI                                                      rsaI
                                 csp6I         mnlI                                        csp6I
                         scfI aciI   tspRI ppuMI   eco0109I/draII                                 ddeI
             tseI styI   mnlI mspAII/nspBII                                                       mnlI bsmAI
     tseI fnu4HI/bsoFI tseI
     fnu4HI/bsoFI bbvI mnlI        nlaIII     CCCTCTACAG CGGTACAGTG AGGACCCCAC AGTACCCCTG  CCCTCTGAGA
     bbvI bsaJI  CAGCCAAGGG GCTGCAAAGC CTCCCCACAC ATGACCCCAG
5001 GGAATGGGGGG                                                                           GGGAGACTCT
     CCTTACCCCC  GTCGGTTCCC  CGACGTTTCG GAGGGGTGTG TACTGGGGTC GGGAGATGTC TCCTGGGGTG TCATGGGGAC
1091 G   M  G  A   A  K  G   L  Q  S  L   P  T  H   D  P  S   P  L  Q  R   Y  S  E   D  P  T   V  P  L  P  S  E  T sau96I
                                                                               haeIII/palI
                                                                               asuI
                                                                               sau96I
                                                                               pspOMI/bsp120I
                                                                               nlaIV
                                                                               hgiJII
                                                                               eco0109I/draII
                                                                               bsp1286
                                                                               bmyI
                                                     sau96I                    banII
                                                     nlaIV                     asuI
                                 tseI                haeIII/palI               apaI
                                 fnu4HI/bsoFI        asuI      mwoI       avaI eco0109I/draII
                                 bbvi                                          bslI mnlI  mnlI
                            tail scfI                CCAGCCCCT TCGCCCCGAG TCGCCCCGAG AGGGCCCTCT
                            maeII pstI  GCCCCCAGCC                                             TCCCGGGAGA
5101 CTGATGGCTA CGTTGCCCCC  CTGACCTGCA                GGTCGGGGA  AGCGGGGCTC
     GACTACCGAT GCAACGGGGG  GACTGGACGT CGGGGGTCGG  ACTTATACAC TTGGTCGGTC TACAAGCCGG
1125 D  G  Y  V  A   P  L   T  C  S   P  Q  P   E   Y  V  N   Q  P  D   V  R  P   Q  P  P   S  P  R  E   G  P  L scrFI
                                                              mvaI
                                                              ecoRII
                                                              dsaV
                                                              bstNI
                                        haeIII/palI           bssKI
                                        sau96I        pleI    bsaJI
            tseI                        asuI   hinfI  apyI                                                  dsaI
            fnu4HI/bsoFI                                      bsaJI mboII                                   bsaJI
            bbvI                nlaIV                                                                       nlaIV
      cac8I mwoI bspMI  banI    hgiCI                                    GAATGGGGTC GTCAAAGACG TTTTTGCCTT TGGGGGTGCC
5201 GCCTGCTGCC CGACTGCTG GTGCCACTCT GGAAAGGGCC AAGACTCTCT CCCCAGGGAA                   tail
                                                                                       maeII                hgiCI
     CGGACGACGG GCTGACGAC CACGGTGAGA CCTTTCCCGG TTCTGAGAGA GGGGTCCCTT CTTACCCCAG CAGTTTCTGC AAAAACGGAA ACCCCCACGG banI
1158 P  A  A  R  R  P  A  G  A  T  L  E   R  A  K  T  L  S   P  G  K  N   G  V  V  K  D  V  F   A  F    G  G  A

```
                                                         mspI
                                                         hpaII
                                                         scrFI
                                                         nciI
                                                         dsaV                       mboII
                                                         cauII                      sau3AI
                                                         bssKI                      mboI/ndeII
                                                         bslI                       dpnII
                                          tseI  bslI                                dpnI
                                          fnu4HI/bsoFI                              bstYI/xhoII
                       mnlI   mboII  bbvI bsaJI bsrI                    bglII                     scfI        taqI
     rmaI
     maeI
     bfaI
 sau96I
  avaII
   asuI       fokI
  ppuMI  mnlI bstF5I
  eco0109I/draII sfaNI
701 AGGACCTAGA GGAAGGCATC CAAACGCTGA TGGGGAGGCT AGCCCCCGGA CTGGGCAGAT CTTCAAGCAG ACCTACAGCA AGTTCGACAC
    TCCTGGATCT CCTTCCGTAG GTTTGCGACT ACCCCTCCGA TCGGGGGCCT GACCCGTCTA GAAGTTCGTC TGGATGTCGT TCAAGCTGTG
                                             ^end of ex 4/ start ex 5

801 AAACTCACAC AACGATGACG CACTACTCAA GAACTACGGG CTGCTCTACT GCTTCAGGAA GGACATGGAC AAGGTCGAGA CATTCCTGCG CATCGTGCAG
    TTTGAGTGTG TTGCTACTGC GTGATGAGTT CTTGATGCCC GACGAGATGA CGAAGTCCTT CCTGTACCTG TTCCAGCTCT GTAAGGACGC GTAGCACGTC
```

FIG. 1V

```
                                                                                                sau96I
                                                                                                haeIII/palI
                                                                                                asuI                                      bsp1286
                                                                                        scrFI   scrFI                                     bmyI
                                                                                        mvaI    mvaI
                                                                                        ecoRII  ecoRII
                                                                                        dsaV    dsaV                                      bsrI
                                                                                        bstNI   bstNI                                     bpmI/gsuI
                                                                                        bssKI   bssKI                                     msII tspRI
                                                               msII          bstF5I tsp45I      bslI   apyI bsaJI
                                                               fokI  mnlI    sfaNI  maeIII  bsrI  mnlI apyI bsaJI
901  TGCCGCTCTG TGGAGGGCAG CTGTGGCTTC TAGCTGCCCG GGTGGCATCC CTGTGACCCC CTCTCCTGGC CCTGGAAGTT GCCACTCCAG
     ACGGCGAGAC ACCTCCCGTC GACACCGAAG ATCGACGGGC CCACCGTAGG GACACTGGGG AGGGGTGACG GGACCTTCAA CGGTGAGGTC
                                                  ^end of spe-sma pBK-CMV/hgh insert to replace intron
                                                                                            ^TG PCR 3' primer
                                                    rmaI
                                                    maeI
                                                    bfaI
                                                    ahdI/eam1105I                       ssPI
001  TGCCCACCAG CCTTGTCCTA ATAAAATTAA GTTGCATCAT TTTGTCTGAC TAGGTGTCCT TCTATAATAT TATGGGGGTGG AGGGGGTGG TATGGAGCAA
     ACGGGTGGTC GGAACAGGAT TATTTTAATT CAACGTAGTA AAACAGACTG ATCCACAGGA AGATATTATA ATACCCCACC TCCCCCCACC ATACCTCGTT
                                                                                            mnlI
                                            tru9I                        sfaNI
                                            mseI
                                            tsp509I
                                   scrFI
                                   nciI
                                   mspI
                                   hpaII
                                   dsaV
                                   xmaI/pspAI
                                   smaI
                                   scrFI
                                   nciI
                                   dsaV
                                   cauII
                                   bssKI
                   aluI        tseI cauII
                   pvuII       fnu4HI/bsoFI
                   tseI        bbvI  bssKI
           mwoI    rmaI        bsaJI
    bsrBI  fnu4HI/bsoFI maeI   mwoI
    bslI   mnlI mspAlI/nspBII alul aval
    aciI   bbvI           bfaI bglI
    fnu4HI/bsoFI
```

FIG. 1W

```
         bslI
         sau96I
         haeIII/palI
         asuI
         sau96I
         pspOMI/bsp120I
         nlaIV
         hgiJII
         bsp1286
         bmyI
         banII
         asuI                              cac8I
         apaI         mboII               haeIII/palI
         nlaIV        bpuAI               sau96I                                           bpmI/gsuI                            mwoI     bslI
     eco0109/draII   bbsI    scfI asuI   eco0109/draII  acil    nlaIV    aluI     tspRI                                        tspRI     aciI                           mnlI
 101 GGGCCCAAG TTGGGAAGAC AACCTGTAGG GCCTGCGGGG TCTATTCGGG AACCAAGCTG GAGTGCAGTG GCACAATCTT GGCTCACTGC AATCTCCGCC
     CCCGGGTTC AACCCTTCTG TTGGACATCC CGGACGCCCC AGATAAGCCC TTGGTTCGAC CTCACGTCAC CGTGTTAGAA CCGAGTGACG TTAGAGGCGG sphI
                                                                                   nspHI
                                                                                   nspI
                                                         scrFI                     scrFI
     scrFI                                               mvaI                      mvaI
     mvaI                                                ecoRII                    ecoRII
     ecoRII                                              dsaV                      dsaV
     dsaV                                                bstNI     nlaIII          nlaIII    cel II/espI
     bstNI                                               bssKI     ppul0I          bstNI
     bssKI        tfiI                                   bssKI     nsiI/avaIII     blpI/bpu1102I                                         esp3I
     bsaJI        hinfI      ddeI          avaI          tfiI      apyI  nlaIII    bssKI     aluI                                        bsmBI
     apyI   bcgI   mnlI      mnlI                        hinfI     cac8I           apyI      ddeI    tsp509I                             bsmAI
 201 TCCTGGGTTC AAGCGATTCT CCTGCCTCAG TGTTGGGATT CCAGGCATGC ATGACCAGGC TCAGCTAATT TTTGTTTTTT TGGTAGAGAC
     AGGACCCAAG TTCGCTAAGA GGACGGAGTC ACAACCCTAA GGTCCGTACG TACTGGTCCG AGTCGATTAA AAACAAAAAA ACCATCTCTG
```

```
                                                                                              scrFI
                                                                                              mvaI
                                                                                              ecoRII
                                                                                              dsaV nlaIV
                                                                                              bstNI
                                                                                              bssKI
                                                                                              bsaJI
                                                                         mspI                 apyI hgiCI
                                                                         hpaII                mwoI banI
          nlaIII    aluI                      bsrBI
                    tsp509I                   aciI         tsp509I
601 CATGGTCATA GCTGTTTCCT GTGTGAAATT GTTATCCGCT CACAATTCCA CACAACATAC GAGCCGGAAG CATAAAGTGT AAAGCCTGGG GTGCCTAATG
    CTACCAGTAT CGACAATAACC CACACTTTAA CAATAGGCCGA GTGTTAAGGT GTGTTGTATG CTCGGCCTTC GTATTTCACA TTTCGGACCC CACGGATTAC aciI
                                                                                                        thaI
                                                                                                        fnuDII/mvnI
                                                                                                        bstUI
                                                                                                        bsh1236I
                                                                                                        hinPI
                                                                                                        hhaI/cfoI
                                                                                   alul  tru9I   eaeI   thaI
                                                                                   pvuII msel    cfrI   fnuDII/mvnI
                                                                                   mspAII/nspBII tfiI haeIII/palI
                 tsp509I  mwoI                                                          cac8I    hinFI bsII  bstUI
                 tru9I    hinPI                                                                  aseI/asnI/vspI bsh1236I
          maeIII msel     hhaI/cfoI cac8I                          bsrI
          mnlI   aseI/asnI/vspI     tspRI aciI
701 AGTGAGGTAA CTCACATTAA TTGCGTTGCG CTCACTGCCC GCTTTCCAGT CGGGAAACCT GTCGTGCCAG CTGATTAAT GAATCGGCCA ACGGCGGGGG
    TCACTCCATT GAGTGTAATT AACGCAACGC GAGTGACGGG CGAAAGGTCA GCCCTTTGGA CAGCACGGTC GACTAATTA CTTAGCCGGT TGCCGCCCCC mwoI
                                                                           fnu4HI/bsoFI
                                                           jinPI           aciI aciI
                 earI/ksp632I                              hhaI/cfoI
                 sapI                                pleI  tseI  mcrI      tseI   bsrBI
                 hinPI     aciI                      hinfI fnu4HI/bsoFI    fnu4HI/bsoFI
          mnlI   hhaI/cfoI                    mnlI   tspRI bbvI  bsiEI     bbvI   cac8I       aluI           aciI
          aciI   mwoI      haeII mboII
801 AGAGGCGGTT TGCGTATTGG GCGCTCTTCC GCTTCCTCGC TCACTGACTC GCTGGCCTCG GTCGTTCGGC TGCGGGAGC GGTATCAGCT CACTCAAAGG
    TCTCCGCCAA ACGCATAACC CGCGAGAAGG CGAAGGAGCG AGTGACTGAG CGACCGGAGC CAGCAAGCCG ACGCCGCTCG CCATAGTCGA GTGAGTTTCC
```

FIG. 1Z

```
                                                    scrFI
                                                    mvaI
                                                    ecoRII                              mwoI
                                                    dsaV                                thaI
                                                    bstNI                               fnuDII/mvnI
                                          bslI      bssKI                               bstUI
                                          cac8I     apyI   bslI                         bsh1236I
                              nlaIII      haeIII/palI HaeIII/palI                       aciI   cac8I
                              nspHI       haeI       haeI   nlaIV                       fnu4HI/bsoFI
                    tfiI      nspI                                                      haeIII/palI
                    hinfI     aflIII
901 CGGTAATACG GTTATCCACA GAATCAGGGG ATAACCAGG AAAGAACATG TGAGCAAAAG GCCAGCAAAA GGCCAGGAAC CGTAAAAAGG CCGCGTTGCT
    GCCATTATGC CAATAGGTGT CTTAGTCCCC TATTGCGTCC TTTCTTGTAC ACTCGTTTTC CGGTCGTTTT CCGGTCCTTG GCATTTTTCC GGGCAACGA scrFI
                                                                                                      mvaI
                                                                                                      ecoRII
                                                                                                      dsaV
                                         hgaI                                                         bstNI
                                         drdI                                                         bssKI
                              sfaNI      taqI   smlI        mnlI                                      apyI
                nlaIV
001 GGGCGTTTTTC CATAGGCTCC GCCCCCCTGA CGAGCATCAC GCTCAAGTCA AAAAATCGAC GCTCAAGTCA GAGGTGGCGA AACCCGACAG ATACCAGGCG
    CCGCAAAAAG GTATCCGAGG CGGGGGGACT GCTCGTAGTG CGAGTTCAGT TTTTTAGCTG CGAGTTCAGT CTCCACCGCT TTGGGCTGTC TATGGTCCGC bciVI
                                                   mspI
                                          bslI     hpaII
                                          aciI     bsaWI                                               hinPI
              bssSI hinPI                 fnu4HI/bsoFI      aciI                                       hhaI/cfoI
    bsaJI     aluI mnlI hhaI/cfoI                                                                      haeII
101 TTTCCCCCTG GAAGCTCCTG CGTGCGCTCT CCTGCCGCTT TACCGGATAC CTGTCCGCCT TTCTCCCTTC GGGAAGCGTG GCGCTTTCTC
    AAAGGGGGAC CTTCGAGGAC GCACGCGAGA GGACGGCGAA ATGGCCTATG GACAGGCGGA AAGAGGGAAG CCCTTCGCAC CGCGAAAGAG hgiAI/aspHI                             tseI
                                                  bsp1286                                 fnu4HI/bsoFI
                                                  bsiHKAI                                 mspAII/nspBII  mspI
                                                  bmyI                                    aciI  hinPI    hpaII
                                        apaLI/snoI                                        mcrI bbvI      bsaWI
              scfI   ddeI               aluI  alw44I/snoI                                 bsiEI hhaI/cfoI
201 AATGCTCACG CTGTAGGTAT CTCAGTTCGG TGTAGGTCGT TCGCTCCAAG CTGGGCTGTG CTGCACGAACC CCCGTTCAG CCCGACCGCT GCGCCTTATC
    TTACGAGTGC GACATCCATA GAGTCAAGCC ACATCCAGCA AGCGAGGTTC GACCCGACAC ACGTGCTTGG GGGCAAGTC GGGCTGGCGA CGGCGAATAG

FIG. 1AA
```

```
                                              alwNI
                                              alw26I/bsmAI
                         mspI                 tseI
                         hpaII                fnu4HI/bsoFI
                         scrFI                bbvI                                                              sau3AI
                         nciI                 tseI        bsrI                                                  mboI/nde
              pleI       dsaV                 bsrI fnu4HI/bsoFI maeIII              mnlI       aciI
              hinfI      cauII                tspRI bbvI                                                hinPI           sau3AI
    maeIII    smlI       bssKi                                                                          thaI            mboI/ndeII
301 CGGTAACTAT CGTCTTGAGT CCAACCCGGT AAGACACGAC TTATCGCCAC TGGCAGCAGC CACTGGTAAC AGGATTAGCA GAGCGAGGTA TGTAGGCGGT
    GCCATTGATA GCAGAACTCA GGTTGGGCCA TTCTGTGCTG AATAGCGGTG ACCGTCGTCG GTGACCATTG TCCTAATCGT CTCGCTCCAT ACATCCGCCA mspI
                 hpaII                                                                                          sau3AI
                 sau3AI                                                          tseI                           mboI/ndeII
                 mboI/ndeII                                                      fnu4HI/bsoFI hhaI/cfoI         dpnII
                 dpnII             mspAlI/nspBII                                 bbvI                           dpnI
                 dpnI              aciI       aciI                cac8I          bstUI                          alwI
         aluI    alwI                                                            bsh1236I    bstYI/xhoII bstYI/xhc
501 TTGGTAGCTC TTGATCCGGC AAACAAACCA CCGCTGGTAG CGGTGGTTTT TTTGTTTTGCA AGCAGCAGAT TACGGCCAGA AAAAAAGGAT CTCAAGAAGA
    AACCATCGAG AACTAGGCCG TTTGTTTGGT GGCGACCATC GCCACCAAAA AAACAAACGT TCGTCGTCTA ATGCCGGTCT TTTTTTCCTA GAGTTCTTCT sau3AI
                                                                                                                        mboI/ndeII
                                                                                                                        dpnII
                                                                                                                mboII   dpnI
                                                                                                                sau3AI  alwI
                                                                                                                mboI/ndeII rmaI
    sau3AI                                          tru9I                                                       dpnII   maeI
    mboI/ndeII                                      mseI             nlaIII                                     dpnI    bstYI/xhoII bstYI/xhoII
    dpnII                           ddeI            taiI             rcaI                                               alwI hphI bfaI
    dpnI              hgaI           tspRI          maeII            bspHI
601 TCCTTTGATC TTTTCTACGG GGTCTGACGC TCAGTGGAAC GAAAACTCAC GTTAAGGGAT TTTGGTCATG AGATTATCAA AAAGGATCTT CACCTAGATC
    AGGAAACTAG AAAAGATGCC CCAGACTGCG AGTCACCTTG CTTTTGAGTG CAATTCCCTA AAACCAGTAC TCTAATAGTT TTTCCTAGAA GTGGATCTAG

```
                                                                                                       sau3AI
                                                                                                       mboI/ndeII
                                                                                                       dpnII
                                                                                                       dpnI
                                                   nlaIV            sau3AI                             nlaIII                                                 sau96I
                                                   mspI             mboI/ndeII                         maeIII  nlaIII                                        avaII
                                                   bsaWI            dpnII                                                                        aciI alu1   asuI
                                                   aluI  hpaII      dpnI       maeIII nlaIII
101 GCTCGTCGTT TGGTATGGCT TCATTCAGCT CCGGTTCCCA ACGATCAAGG CGAGTTACAT GATCCCCCAT GTTGTGCAAA AAAGCGGTTA GCTCCTTCGG
    CGAGCAGCAA ACCATACCGA AGTAAGTCGA GGCCAAGGGT TGCTAGTTCC GCTCAATGTA CTAGGGGTA CAACACGTTT TTTCGCCAAT CGAGGAAGCC sau3AI
    mboI/ndeII
    dpnII
    dpnI                                                                                               fokI
    pvuI/bspCI                              aciI              tspRI                                    bstF5I
    mcrI                                    fnu4HI/bsoFI      tseI                                             sfaNI
    bsiEI                haeIII/palI                         fnu4HI/bsoFI
         mnlI dpnI       eaeI               nlaIII           bbvI           tsp509I           nlaIII
                         cfrI    tspRI      msII
201 TCCTCCGATC GTTGTCAGAA GTAAGTTGGC CGCAGTGGTA TCACTCATGG TTATGGCAGC ACTGCATAAT TCTCTTACTG TCATGCCATC CGTAAGATGC
    AGGAGGCTAG CAACAGTCTT CATTCAACCG GCGTCACCAT AGTGAGTACC AATACCGTCG TGACGTATTA AGAGAATGAC AGTACGGTAG GCATTCTACG hgaI
                                                                                     hinII/acyI                           hinPI
                                                                                     ahaII/bsaHI                          hhaI/cfoI
                                                                                                                          thaI
                                                                                         mspI                             fnuDII/mvnI
                                                                                         hpaII                            bstUI
                                                                                         scrFI                            bsh1236I
                                                       mcrI                              nciI                             aciI
                                                       bsiEI                             dsaV
                                                       bcgI                              cauII                   sau3AI
                                            fnu4HI/bsoFI                                 bssKI                   mboI/ndeII
                                 ddeI       aciI                                                                 dpnII
301 TTTTCTGTGA CTGGTGAGTA CTCAACCAAG TCATTCTGAG AATAGTGTAT GCGGCGACCG AGTTGCTCTT GCCCGGCGTC ATCACGGGAT AATACCGCGC
    AAAAGACACT GACCACTCAT GAGTTGGTTC AGTAAGACTC TTATCACATA CGCCGCTGGC TCAACGAGAA CGGGCCGCAG TAGTGCCCTA TTATGGCGCG sau3AI
                                                                                                       mboI/ndeII
                                       taiI                                                            dpnII
                    hgiAI/aspHI        maeII                                                           dpnI
                    bsp1286            psp1406I                                            mspAII/nspBII bsrI
                    bsiHKAI            aciI                                                bstYI/xhoII  alwI   taqI
         tru9I      bmyI               xmnI                                         smlI  alwI  aciI   bstYI/xhoII  maeIII
         mseI       ahaIII/draI        asp700     mboII
401 CACATAGCAG AACTTTAAAA GTGCTCATCA TTGGAAAACG TTCTTCGGGG CGAAAACTCT CAAGGATCTT ACCGCTGTTG AGATCCAGTT CGATGTAACC
    GTGTATCGTC TTGAAATTTT CACGAGTAGT AACCTTTTGC AAGAAGCCCC GCTTTTGAGA GTTCCTAGAA TGGCGACAAC TCTAGGTCAA GCTACATTGG
```

FIG. 1DD

```
         hgiAI/aspHI
         bsp1286            eco57I
         bsiHKAI            mboII
         bmyI       sau3AI
         apaLI/snoI mboI/ndeII
         alw44IsnoI dpnII
      bssSI         dpnI           sfaNI              hphI                                         aciI
                                                                                                  fnu4HI/bsoFI
                                                                             nlaIII
                                                                             rcaI    bciVI
                                                                             bspHI aciI
                                                                             bsmAI bsrBI
501 CACTCGTGCA CCCAACTGAT CTTCAGCATC TTTTACTTTC ACCAGCGTTT CTGGGTGAGC AAAAACAGGA AGGCAAAATG CCGCAAAAA GGGAATAAGG
    GTGAGCACGT GGGTTGACTA GAAGTCGTAG AAAATGAAAG TGGTCGCAAA GACCCACTCG TTTTTGTCCT TCCGTTTTAC GGCGTTTTT CCCTTATTCC mboII
                          earI/ksp632I    sspI
       msII
601 GCGACACGGA AATGTTGAAT ACTCATACTC TTCCTTTTTC AATATTATTG AAGCATTTAT CAGGGTTATT GTCTCATGAG CGGATACATA TTTGAATGTA
    CGCTGTGCCT TTACAACTTA TGAGTATGAG AAGGAAAAAG TTATAATAAC TTCGTAAATA GTCCCAATAA CAGAGTACTC GCCTATGTAT AAACTTACAT hinPI                                  taiI
                  thaI                                   maeII
                  fnuDII/mvnI                            hinII/acyI                   nlaIII
                  bstUI                                  ahaII/bsaHI                  rcaI      tru9I
                  bsh1236I                               aatII ddeI                   bspHI     mseI
                  aciI
            nnaIV hhaI/cfoI
701 TTTAGAAAA TAAACAAATA GGGGTTCCGC GCACATTTCC CCGAAAAGTG CCACCTGACG TCTAAGAAAC CATTATTATC ATGACATTAA CCTATAAAA
    AAATCTTTT ATTTGTTTAT CCCCAAGGCG CGTGTAAAGG GGCTTTTCAC GGTGGACTGC AGATTCTTTG GTAATAATAG TACTGTAATT GGATATTTT thaI                                          mspI
                                                          fnuDII/mvnI                                   scrFI
                                                          bsh1236I                                      nciI esp3I
                                                          hinPI                                         dsaV bsmBI
               sau96I     mboII                           thaI                                  tseI    cauII
               haeIII/palI                                fnuDII/mvnI                           fnu4HI/bsoFI
               eco0109I/draII                             bstUI                                 nlaIII  bssKI
            mnlI    bpuAI                                 bsh1236I                              nspHI aluI hpaII
         bssSI asuI bbsI                        mnlI hhaI/cfoI hphI       hphI       mnlI       nspI bbvI bsII bsmAI maeIII tsp45I
801 TAGGGTATC ACGAGGCCCT TTCGTCTTCA AGAATACTGC CTCGGCCGTT TCGGTGATGA CGGTGAAAAC CTCTGACACA TGCAGCTCCC GGAGACGGTC
    ATCCCATAG TGCTCCGGGA AAGCAGAAGT TCTTATGACG GAGCCGGCAA AGCCACTACT GCCACTTTTG GAGACTGTGT ACGTCGAGGG CCTCTGCCAG
```

```
                                    scrFI
                                    mvaI
                                    ecoRII
                                    dsaV
                                    bstNI                                            tspRI
                                    bssKI                                            bsrI
                                    bsaJI              tsp45I                        haeIII/palI
          tseI                      apyI               maeIII                        eaeI
          fnu4HI/bsoFI tru9I                           bsrI      maeII               cfrI
          bbvI         mseI   maeIII
201 GTGCTGCAAG GCGATTAAGT TGGGTAACGC CAGGGTTTTC CCAGTCACGA CGTTGTAAAA CGACGGCCAG TGCC
    CACGACGTTC CGCTAATTCA ACCCATTGCG GTCCCAAAAG GGTCAGTGCT GCAACATTTT GCTGCCGGTC ACGG
```

FIG. 1GG

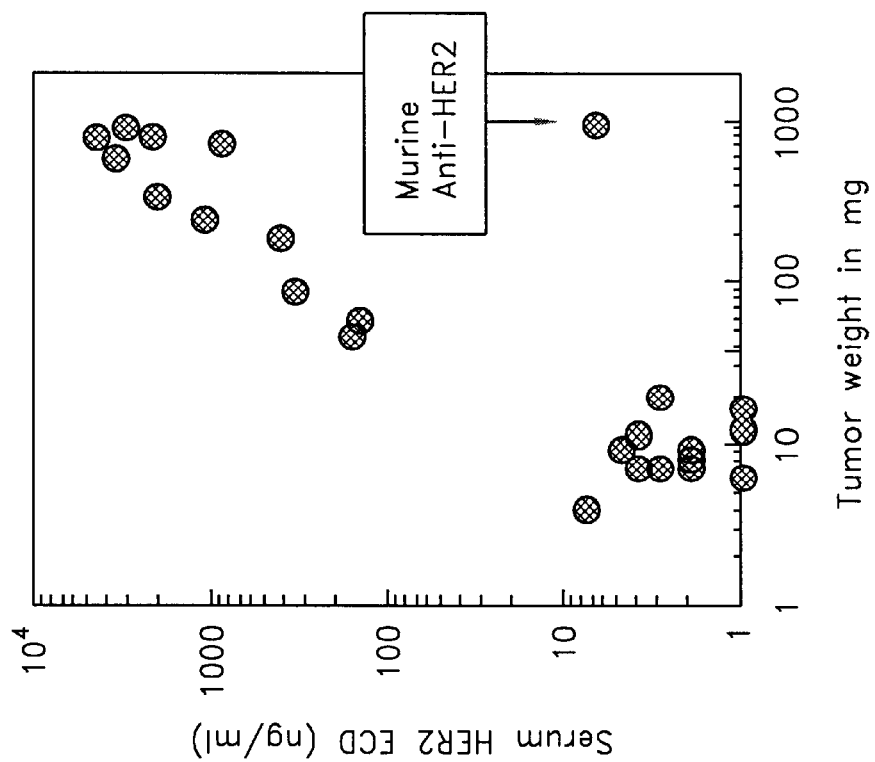
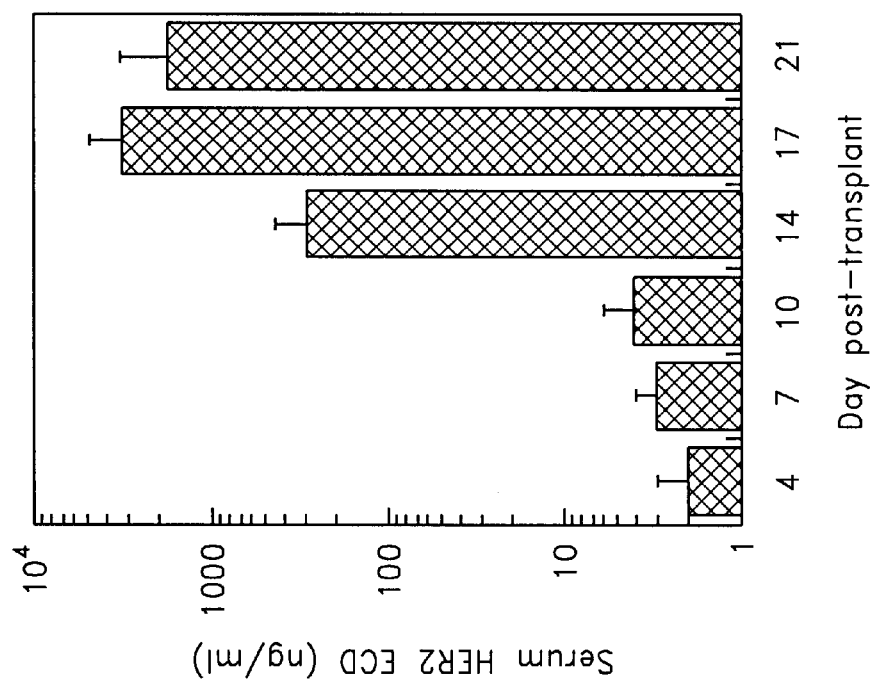
FIG. 2B
FIG. 2A

|  | 0 | heregulin | EGF |
|---|---|---|---|
| HER5 7C2 | + | + | +/− |
| 4D5 | + | + | + |
| 2C4 | + | + | + |
| HER3-4 7C2 | + | + | − |
| 4D5 | + | − | + |
| 2C4 | − | − | − |
| HER3-10 7C2 | + | + | + |
| 4D5 | + | − | + |
| 2C4 | − | + | +/− |
| HER3-19 7C2 | − | + | − |
| 4D5 | − | − | − |
| 2C4 | − | − | − |

FIG. 12

RODENT HER2 TUMOR MODEL

This application claims priority under 35 USC §119(e) to U.S. Provisional Application No. 60/189,844, filed Mar. 16, 2000.

BACKGROUND OF THE INVENTION

FIELD OF THE INVENTION

The present invention concerns novel HER2-transgenic non-human mammals and their use to develop a tumor model to test HER2-directed cancer therapies. The invention further concerns anticancer agents identified in this model, and their use in the treatment of cancer.

DESCRIPTION OF THE RELATED ART

Members of the ErbB family of receptor tyrosine kinases are important mediators of cell growth, differentiation and survival. The receptor family includes four distinct members, including epidermal growth factor receptor (EGFR or ErbB 1), HER2 (ErbB2 or $p185^{neu}$), HER3 (ErbB3) and HER4 (ErbB4 or tyro2).

$p185^{neu}$, was originally identified as the product of the transforming gene from neuroblastomas of chemically treated rats. The activated form of the neu proto-oncogene results from a point mutation (valine to glutamic acid) in the transmembrane region of the encoded protein. Amplification of the human homolog of neu is observed in breast and ovarian cancers and correlates with a poor prognosis (Slamon et al., *Science*, 235:177–182 (1987); Slamon et al., *Science*, 244:707–712 (1989); and U.S. Pat No. 4,968,603). To date, no point mutation analogous to that in the neu proto-oncogene has been reported for human tumors. Overexpression of ErbB2 (frequently but not uniformly due to gene amplification) has also been observed in other carcinomas including carcinomas of the stomach, endometrium, salivary gland, lung, kidney, colon, thyroid, pancreas and bladder. See, among others, King et al., *Science*, 229:974 (1985); Yokota et al., *Lancet*, 1:765–767 (1986); Fukushigi et al., *Mol Cell Biol.*, 6:955–958 (1986); Geurin et al., *Oncogene Res.*, 3:21–31 (1988); Cohen et al., *Oncogene*, 4:81–88 (1989); Yonemura et al., *Cancer Res.*, 51:1034 (1991); Borst et al., *Gynecol. Oncol.*, 38:364 (1990); Weiner et al., *Cancer Res.*, 50:421–425 (1990); Kern et al., *Cancer Res.*, 50:5184 (1990); Park et al., *Cancer Res.*, 49:6605 (1989); Zhau et al., *Mol. Carcinog.*, 3:354–357 (1990); Aasland et al. *Br. J. Cancer* 57:358–363 (1988); Williams et al. *Pathobiology* 59:46–52 (1991); and McCann et al., *Cancer*, 65:88–92 (1990). ErbB2 may be overexpressed in prostate cancer (Gu et al. *Cancer Lett.* 99:185–9 (1996); Ross et al. *Hum. Pathol.* 28:827–33 (1997); Ross et al. *Cancer* 79:2162–70 (1997); and Sadasivan et al. *J. Urol.* 150:126–31 (1993)).

Antibodies directed against the rat $p185^{neu}$ and human ErbB2 protein products have been described. Drebin and colleagues have raised antibodies against the rat neu gene product, $p185^{neu}$. See, for example, Drebin et al., *Cell* 41:695–706 (1985); Myers et al., *Meth. Enzym.* 198:277–290 (1991); and WO94/22478. Drebin et al. *Oncogene* 2:273–277 (1988) report that mixtures of antibodies reactive with two distinct regions of $p185^{neu}$ result in synergistic anti-tumor effects on neu-transformed NIH-3T3 cells implanted into nude mice. See also U.S. Pat. 5,824,311 issued Oct. 20, 1998.

Other anti-ErbB2 antibodies with various properties have been described in Tagliabue et al. Int. *J. Cancer* 47:933–937 (1991); McKenzie et al. *Oncogene* 4:543–548 (1989); Maier et al. *Cancer Res.* 51:5361–5369 (1991); Bacus et al. *Molecular Carcinogenesis* 3:350–362 (1990); Stancovski et al. PNAS (USA) 88:8691–8695 (1991); Bacus et al. *Cancer Research* 52:2580–2589 (1992); Xu et al. *Int. J. Cancer* 53:401–408 (1993); W094/00136; Kasprzyk et al. *Cancer Research* 52:2771–2776 (1992);Hancock et al. *Cancer Res.* 51:4575–4580 (1991); Shawver et al. *Cancer Res.* 54:1367–1373 (1994); Arteaga et al. *Cancer Res.* 54:3758–3765 (1994); Harwerth et al. *J. Biol. Chem.* 267:15160–15167 (1992); U.S. Pat. No. 5,783,186; and Klapper et al. *Oncogene* 14:2099–2109 (1997).

Hudziak et al., *Mol. Cell. Biol.* 9(3): 1165–1172 (1989) describe the generation of a panel of anti-ErbB2 antibodies which were characterized using the human breast tumor cell line SK-BR-3. Relative cell proliferation of the SK-BR-3 cells following exposure to the antibodies was determined by crystal violet staining of the monolayers after 72 hours. Using this assay, maximum inhibition was obtained with the antibody called 4D5 which inhibited cellular proliferation by 56%. Other antibodies in the panel reduced cellular proliferation to a lesser extent in this assay. The antibody 4D5 was further found to sensitize ErbB2-overexpressing breast tumor cell lines to the cytotoxic effects of TNF-α. See also U.S. Pat. No. 5,677,171 issued Oct. 14, 1997. The anti-ErbB2 antibodies discussed in Hudziak et al. are further characterized in Fendly et al. *Cancer Research* 50:1550–1558 (1990); Kotts et al. *In Vitro* 26(3):59A (1990); Sarup et al. *Growth Regulation* 1:72–82 (1991); Shepard et al. *J. Clin. Immunol.* 11(3):117–127 (1991); Kumar et al. *Mol. Cell. Biol.* 11(2):979–986 (1991); Lewis et al. *Cancer Immunol. Immunother.* 37:255–263 (1993); Pietras et al. *Oncogene* 9:1829–1838 (1994); Vitetta et al. *Cancer Research* 54:5301–5309 (1994); Sliwkowski et al. *J. Biol. Chem.* 269(20):14661–14665 (1994); Scott et al. *J. Biol. Chem.* 266:14300–5 (1991); D'souza et al. *Proc. Natl. Acad. Sci.* 91:7202–7206 (1994); Lewis et al. *Cancer Research* 56:1457–1465 (1996); and Schaefer et al. *Oncogene* 15:1385–1394 (1997).

The murine monoclonal anti-HER2 antibody inhibits the growth of breast cancer cell lines that overexpress HER2 at the 2+ and 3+ level, but has no activity on cells that express lower levels of HER2 (Lewis et al., *Cancer Immunol. Immunother.* [1993]). Based on this observation, antibody 4D5 was humanized (Carter et al., *Proc. Natl. Acad. Sci. USA* 89: 4285–4289 [1992]). The humanized version designated HERCEPTIN® (huMAb4D5-8, rhuMAb HER2, U.S. Pat. No. 5,821,337) was tested in breast cancer patients whose tumors overexpress HER2 but who had progressed after conventional chemotherapy (Cobleigh et al., *J. Clin. Oncol.* 17: 2639–2648 [1999]). Most patients in this trial expressed HER2 at the 3+ level, though a fraction was 2+ tumors. Remarkably, HERCEPTIN® induced clinical responses in 15% of patients (complete responses in 4% of patients, and partial responses in 11%) and the median duration of those responses was 9.1 months. HERCEPTIN® received marketing approval from the Food and Drug Administration Sep. 25, 1998 for the treatment of patients with metastatic breast cancer whose tumors overexpress the ErbB2 protein.

Although HERCEPTIN° is a breakthrough in treating patients with ErbB2-overexpressing breast cancers that have received extensive prior anti-cancer therapy, generally approximately 85% of the patients in this population fail to respond or respond only poorly to HERCEPTIN® treatment, and in the clinical trial preceding market approval, the median time to disease progression in all treated patients was only 3.1 months.

Therefore, there is a significant clinical need for developing further HER2-directed cancer therapies for those patients with HER2-overexpressing tumors or other diseases associated with HER2 expression that do not respond or respond poorly to HERCEPTIN® treatment.

SUMMARY OF THE INVENTION

The present invention is based on the development of a novel HER2-transgenic mouse tumor model that expresses HER2 at high levels, comparable to those in HER2-positive human patients, but that responds poorly to HERCEPTIN®.

In one aspect, the invention concerns a transgenic non-human mammal that produces in its mammary gland cells detectable levels of a native human HER2 protein or a fragment thereof, wherein said transgenic mammal has stably integrated into its genome a nucleic acid sequence encoding a native human HER2 protein or a fragment thereof having the biological activity of native human HER2, operably linked to transcriptional regulatory sequences directing its expression to the mammary gland, and develops a mammary tumor not responding or poorly responding to anti-HER2 antibody treatment. The transcriptional regulatory sequences preferably comprise a mammary gland specific promoter, such as the glucocorticoid-inducible promoter present in the mouse mammary tumor virus long terminal repeat (MMTV LTR). The non-human transgenic mammal preferably overexpresses the HER2 protein, more preferably, it expresses native human HER2 protein in at least about 500,000 copies per cell, even more preferably in at least about 2,000,000 copies per cell. Without limitation, the non-human transgenic mammal may, for example, be mouse, rat, rabbit, pig, sheep, goat or cattle. In a particular embodiment, the HER2-transgenic mammal develops a tumor that does not respond or responds poorly to treatment by a humanized version of the murine anti-HER2 antibody 4D5, such as HERCEPTIN®.

In another aspect, the invention concerns a non-human animal model for HER2-expressing tumors comprising a non-human mammal bearing a tumor overexpressing HER2 and not responding or poorly responding to anti-HER2 antibody treatment. The tumor preferably expresses a human HER2 protein in at least about 500,000 copies per cell, more preferably in at least about 2,000,000 copies per cell. In a preferred embodiment, the tumor has been transplanted from a transgenic non-human mammal which has stably integrated into its genome a nucleic acid sequence encoding a native human HER2 protein or a fragment thereof having the biological activity of native human HER2, operably linked to transcriptional regulatory sequences directing its expression to the mammary gland.

In yet another aspect, the invention concerns a transgene construct comprising nucleic acid encoding a native human HER2 protein or a fragment thereof, under the control of transcriptional regulatory sequences directing its expression to the mammary gland. The transgene construct preferably comprises a mammary gland specific promoter, such as an MMTV-LTR promoter.

In a further aspect, the invention concerns a stable cell line established from a HER2-transgenic non-human mammal that produces in its mammary gland cells detectable levels of a native human HER2 protein or a fragment thereof, wherein such transgenic mammal has stably integrated into its genome a nucleic acid sequence encoding a native human HER2 protein or a fragment thereof having the biological activity of native human HER2, operably linked to transcriptional regulatory sequences directing its expression to the mammary gland, and develops a mammary tumor not responding or poorly responding to anti-HER2 antibody treatmement. In one embodiment the stable cell line is a breast cancer cell line.

In one embodiment the stable breast cancer cell line is selected from the group consisting of HER-32, HER-3081-3-4, HER-3081-3-19, HER-3081-3-33, HER-3081-3-12C and HER-3080-5L1. In another embodiment the stable breast cancer cell line is selected from the group consisting of the stable cell lines HER-5, HER-3081-3-1 and HER-3081-3-10 deposited with ATCC on Feb. 28, 2001 under accession numbers PTA-3135, PTA-3133 and PTA-3134, In another aspect, the invention concerns a method of screening drug candidates for the treatment of a disease or disorder characterized by the overexpression of HER2 comprising (a) transplanting cells from a stable breast cancer cell line into a non-human animal, (b) administering a drug candidate to the non-human animal and (c) determining the ability of the candidate to inhibit the formation of tumors from the transplanted cell line.

The invention also concerns a method of screening drug candidates for the treatment of a disease or disorder characterized by the overexpression of HER2 comprising (a) contacting cells from a stable breast cancer cell line with a drug candidate and (b) evaluating the ability of the drug candidate to inhibit the growth of the stable cell line.

In another aspect the invention concerns a method of screening drug candidates for the treatment of a disease or disorder characterized by the overexpression of HER2 comprising (a) contacting cells from a stable breast cancer cell line with a drug candidate and (b) evaluating the ability of the drug candidate to block ligand activation of HER2. In one embodiment the ability of the drug candidate to block heregulin binding is evaluated. In another embodiment the ability of the drug candidate to block ligand-stimulated tyrosine phosphorylation is evaluated.

In yet another aspect, the invention concerns a method of screening drug candidates for the treatment of a disease or disorder characterized by the overexpression of HER2 comprising (a) contacting cells from a stable breast cancer cell line with a drug candidate and (b) evaluating the ability of the drug candidate to induce cell death. In one embodiment the ability of the drug candidate to induce apoptosis is evaluated.

In a still further aspect, the invention concerns a method of screening drug candidates for the treatment of a disease or disorder characterized by the overexpression of HER2 comprising (a) administering a drug candidate to a transgenic non-human mammal that overexpresses in its mammary gland cells a native human HER2 protein or a fragment thereof, wherein such transgenic mammal has stably integrated into its genome a nucleic acid sequence encoding a native human HER2 protein or a fragment thereof having the biological activity of native human HER2, operably linked to transcriptional regulatory sequences directing its expression to the mammary gland, and develops a mammary tumor not responding or poorly responding to anti-HER2 antibody treatment, or to a non-human mammal bearing a tumor transplanted from said transgenic non-human mammal; and (b) evaluating the effect of the drug candidate on the target disease or disorder. Without limitations, the disease or disorder may be a HER2-overexpressing cancer, such as breast, ovarian, stomach, endometrial, salivary gland, lung, kidney, colon, thyroid, pancreatic and bladder cancer. The cancer preferably is breast cancer which expressed HER2 in at least about 500,000 copies per cell, more preferably at least about 2,000,000 copies per cell. Drug candidates may, for example, be evaluated for their ability to induce cell death and/or apoptosis, using assay methods well known in the art and described hereinafter. The drug candidates may, for example, be antibodies or other polypeptides, antibody conjugates, peptides, or organic or inorganic small molecules.

The invention further concerns anti-cancer molecules identifiable in the animal models and other assays of the present invention, and compositions comprising such molecules in admixture with a pharmaceutically acceptable carrier.

BRIEF DESCRIPTION OF THE DRAWINGS

Figure 1C:
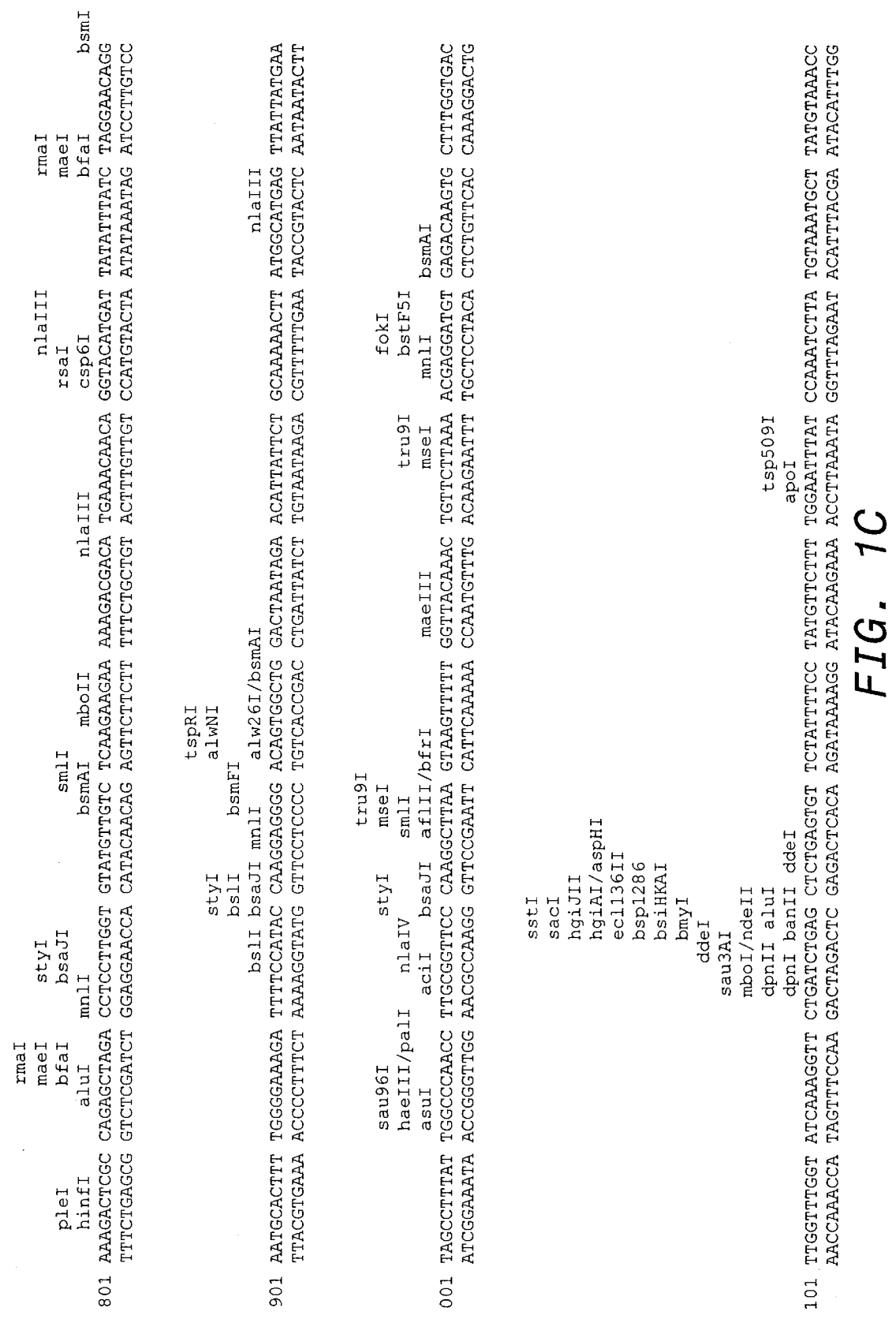
Figure 1F:
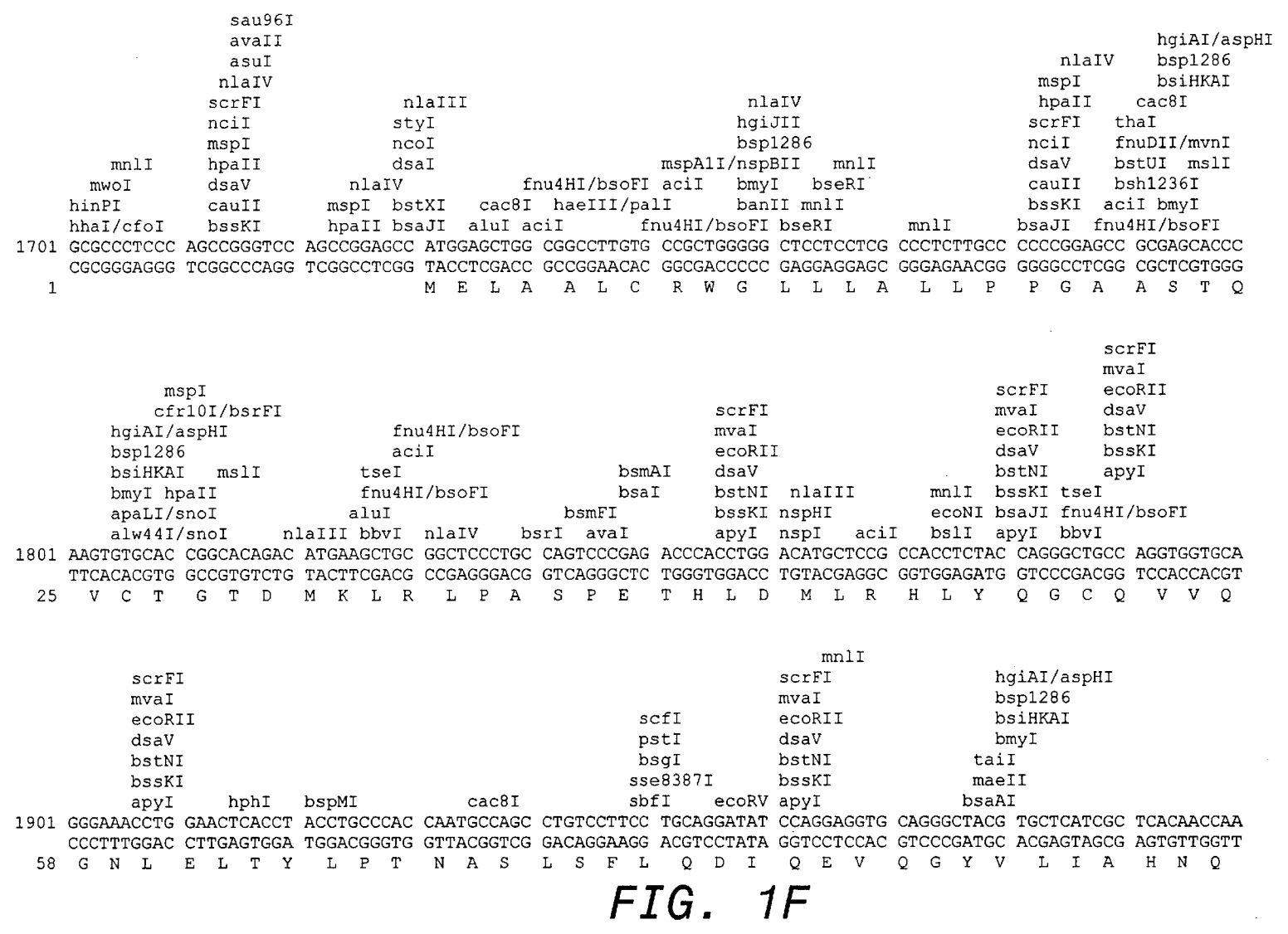
Figure 1K:
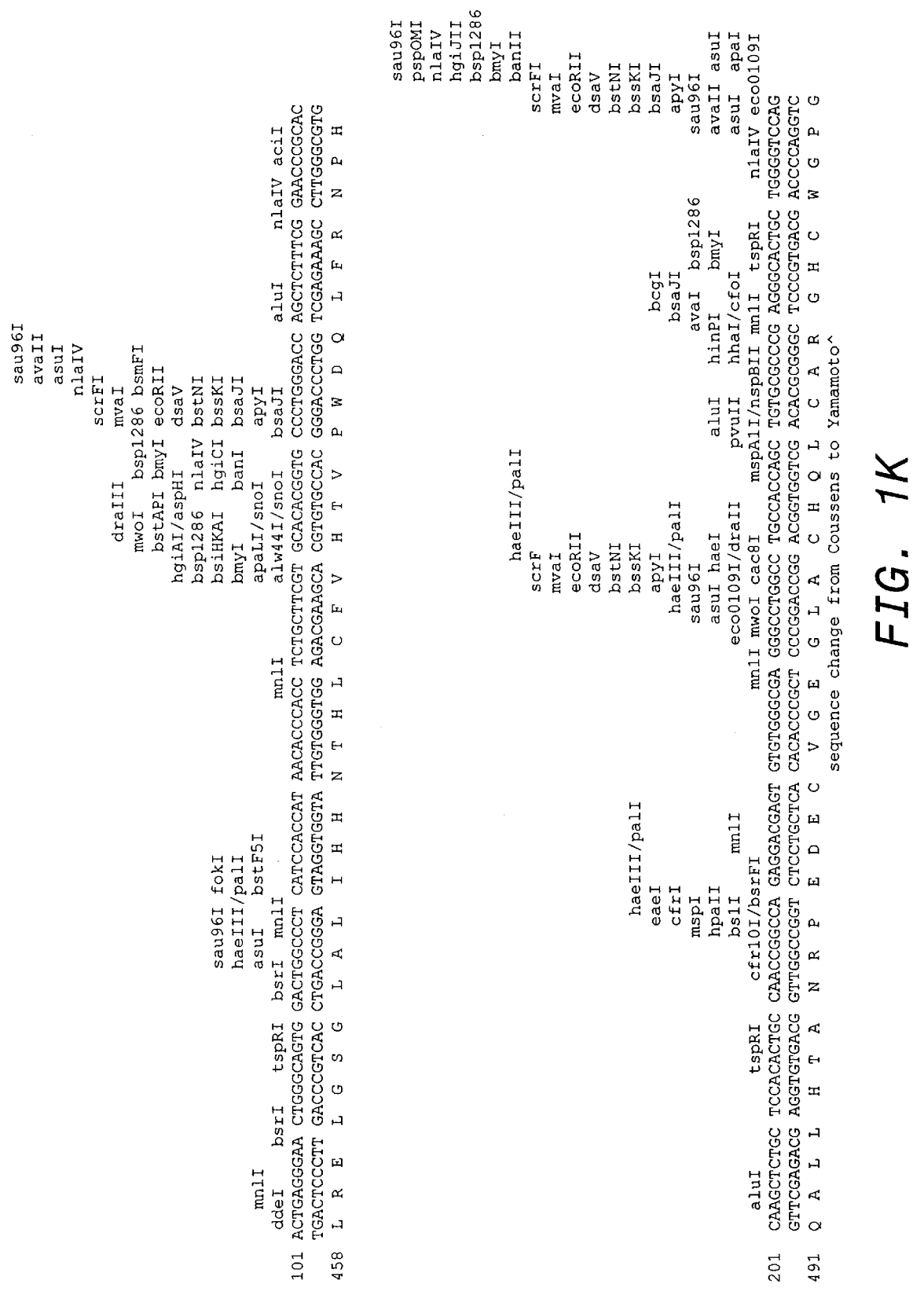
Figure 1L:
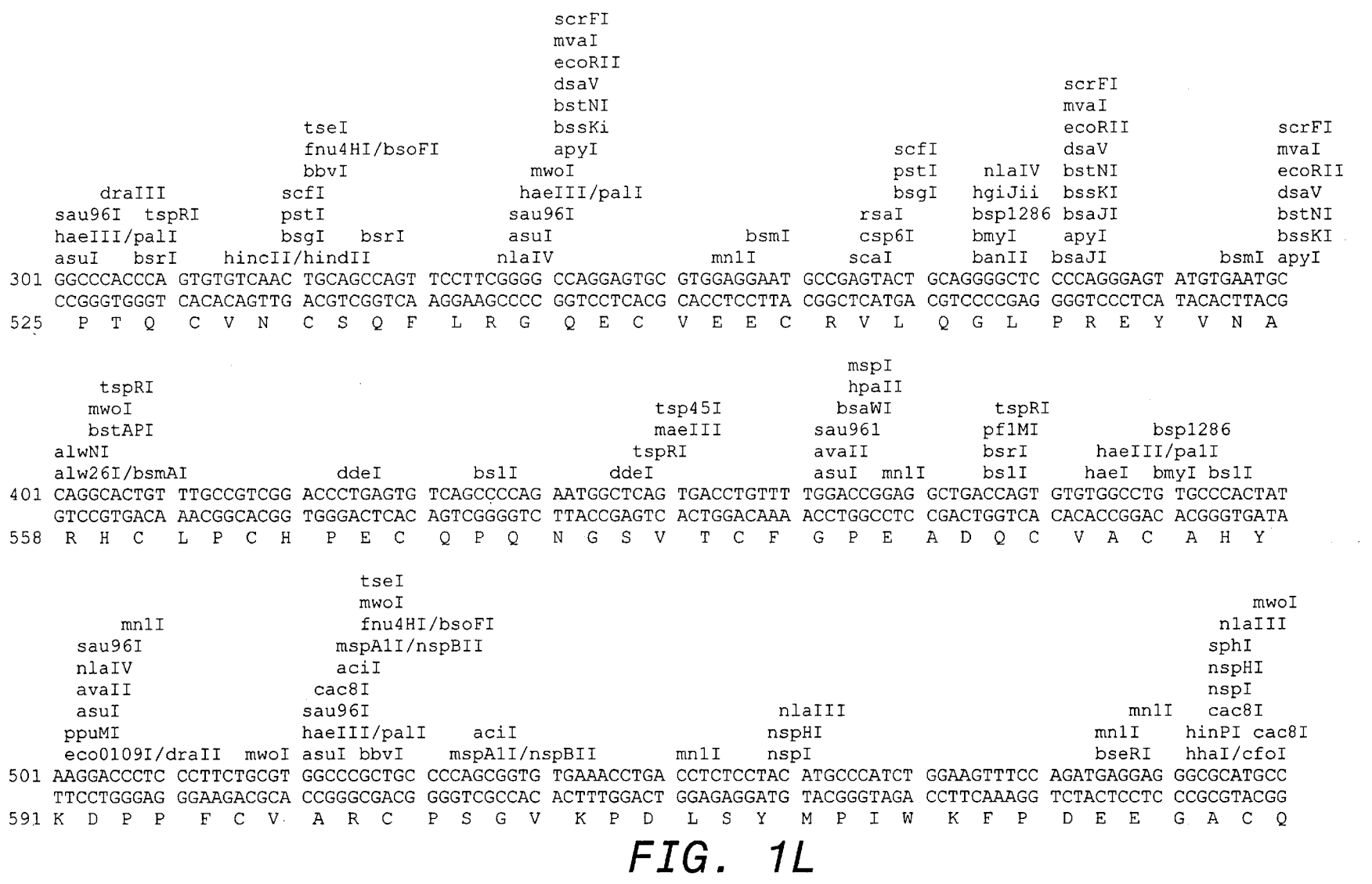
Figure 1Q:
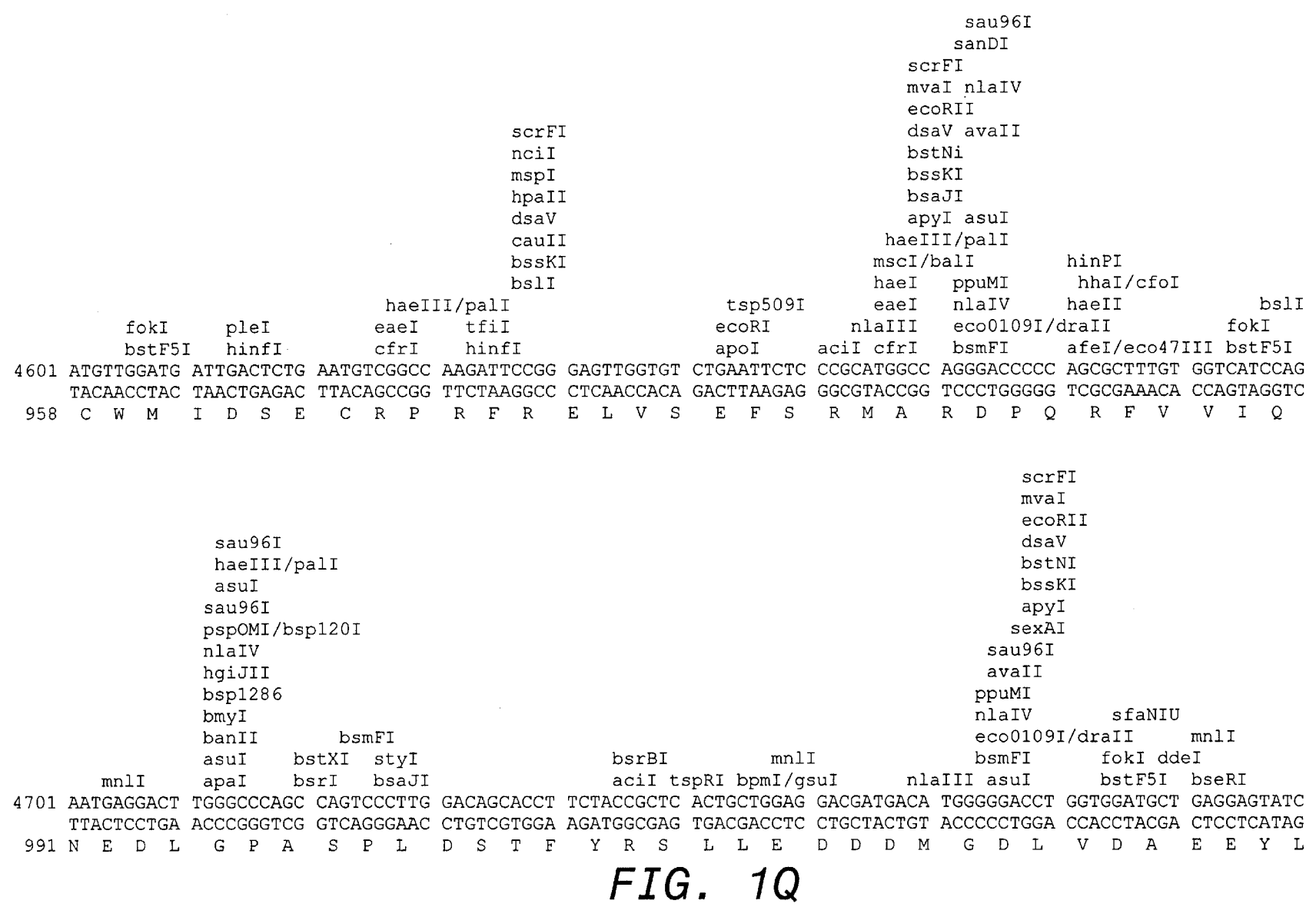
Figure 1R:
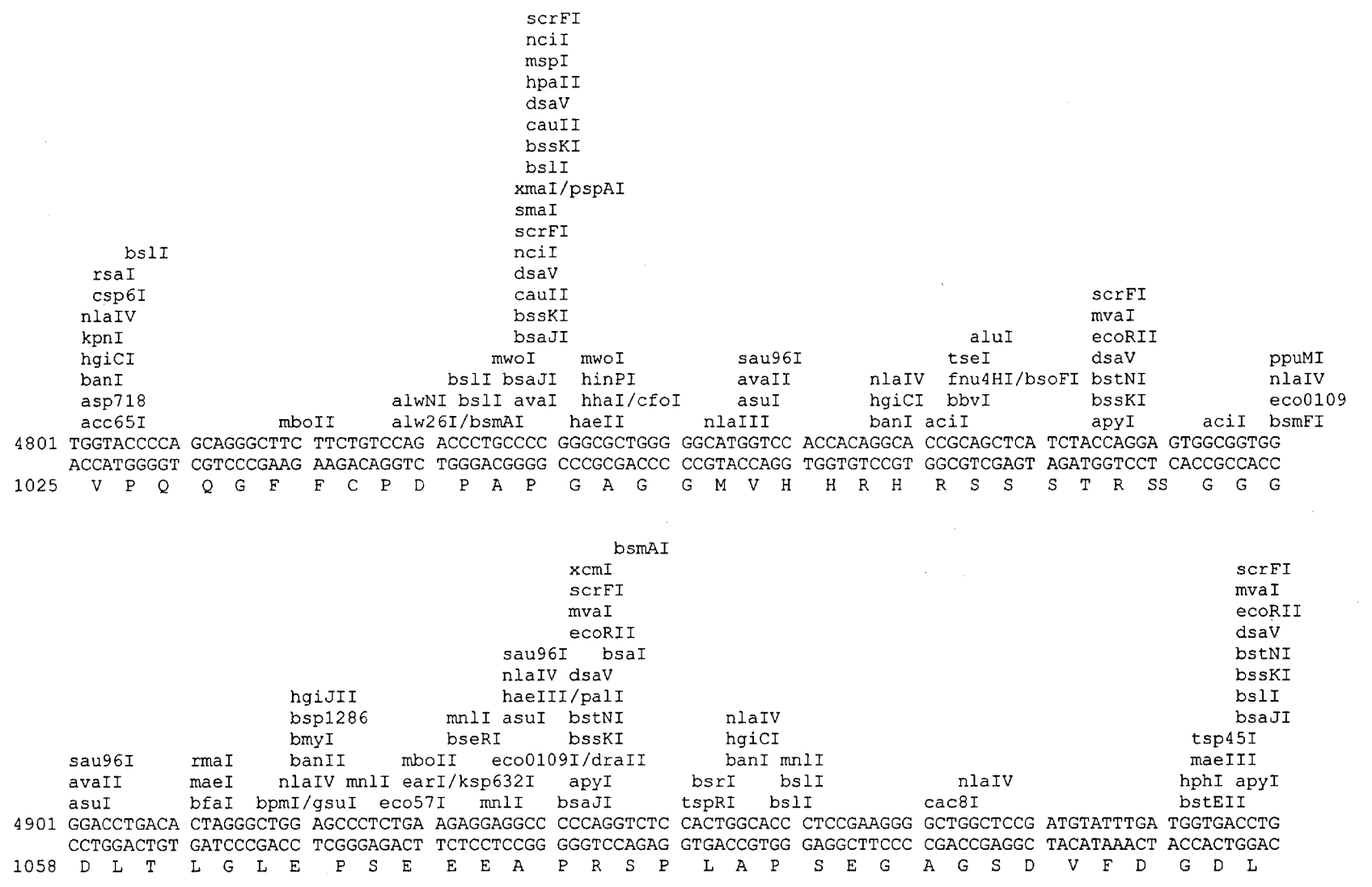
Figure 1T:
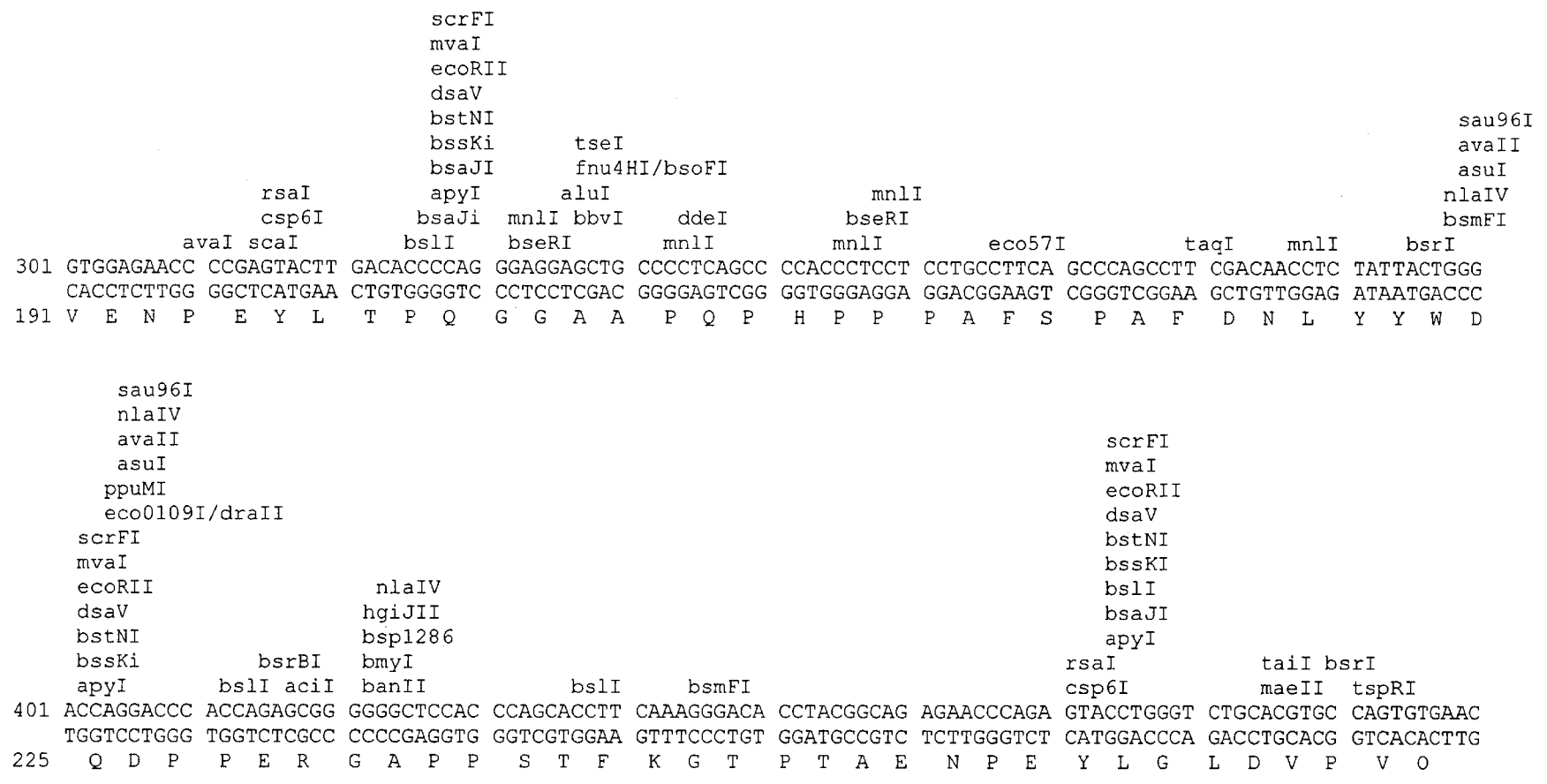

FIGS. 1A–GG shows the nucleotide sequence of a HER2 transgene plasmid construct (SEQ ID NO: 1) directing the expression of native human HER2 in the mammary gland of a transgenic mouse. The reverse strand is also depicted (SEQ ID NO: 4). The figure includes the nucleotide sequence of HER2 cDNA insert (SEQ ID NO: 2) as well as the deduced amino acid sequence of HER2 (SEQ ID NO: 3).

FIGS. 2A–B The amount of HER2 ECD shed into serum increases following transplant (FIG. 2A) and is proportional to tumor weight (FIG. 2B).

FIG. 12 is a summary of the growth response of HER2 transgenic cell lines to anti-HER2 antibodies in the presence or absence of mitogens.

DETAILED DESCRIPTION OF THE PREFERRED EMBODIMENT

I. Definitions

Unless defined otherwise, technical and scientific terms used herein have the same meaning as commonly understood by one of ordinary skill in the art to which this invention belongs. Singleton et al., *Dictionary of Microbiology and Molecular Biology 2nd ed.*, J. Wiley & Sons (New York, N.Y. 1994). One skilled in the art will recognize many methods and materials similar or equivalent to those described herein, which could be used in the practice of the present invention. Indeed, the present invention is in no way limited to the methods and materials described. For purposes of the present invention, the following terms are defined below.

Throughout the disclosure, the terms "ErbB2", "ErbB2 receptor", "c-erb-B2", and "HER2" are used interchangeably, and, unless otherwise indicated, refer to a native sequence ErbB2 human polypeptide, or a functional derivative thereof. "her2", "erbB2" and "c-erb-B2" refer to the corresponding human gene. The terms "native sequence" or "native" in this context refer to a polypeptide having the sequence of a naturally occurring polypeptide, regardless its mode of preparation. Such native sequence polypeptides can be isolated from nature or can be produced by recombinant or synthetic means, or by any combination of these or similar methods.

Figure 3:
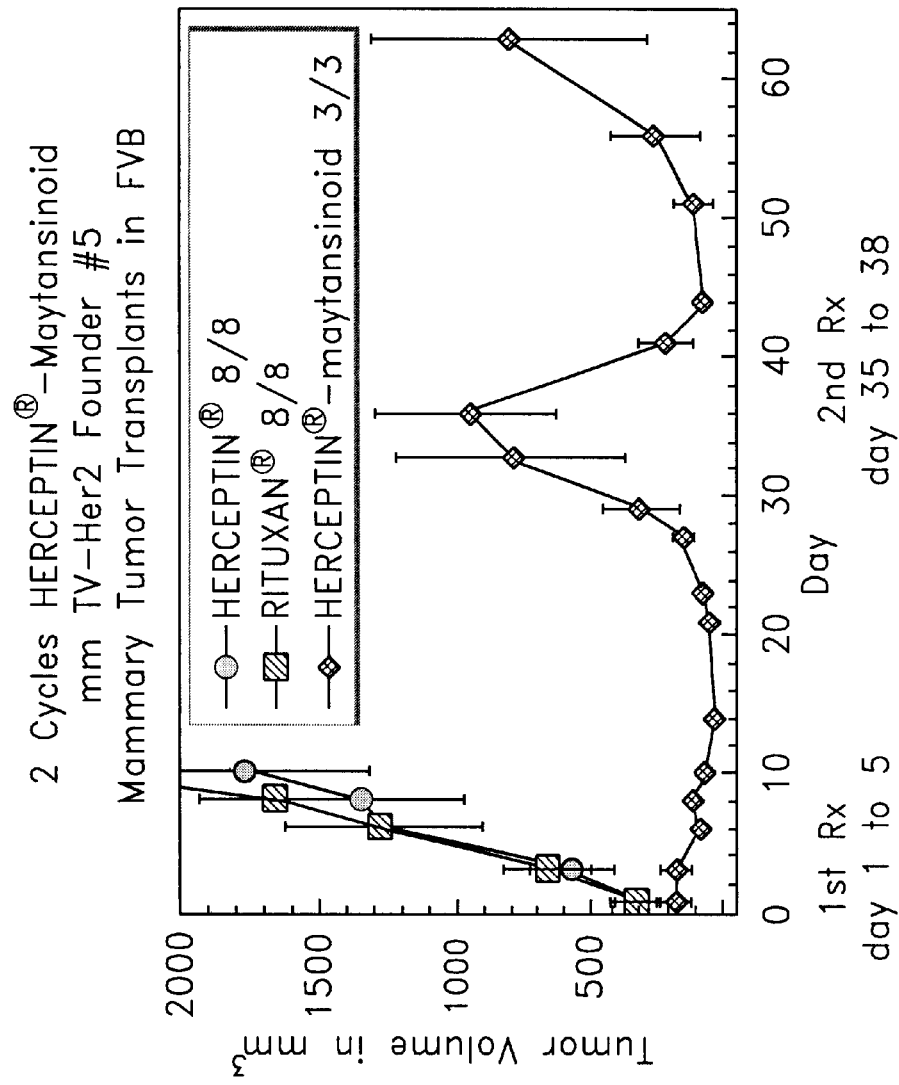
FIG. 3 Effect of HERCEPTIN®-maytansinoid on HER2-transgenic tumors. Two mm3 pieces of MMTV-HER2-transgenic tumors were transplanted into the mammary fat pad of FVB mice. When tumors reached 250 mm$^3$, groups of 8 mice were injected i.v. on 5 consecutive days with a HERCEPTIN®-maytansinoid conjugate. Two other groups of mice were treated IP twice per week with 10 mg/kg of either HERCEPTIN® or RITUXAN®.

Accordingly, "native" or "native sequence" HER2 polypeptides may be isolated from nature, produced by techniques of recombinant DNA technology, chemically synthesized, or produced by any combinations of these or similar methods. The amino acid sequence and encoding nucleotide sequence of a native human HER2 polypeptide is disclosed, for example, in Semba et al., *PNAS* (USA) 82:6497–65)2 (1985) and Yamamoto et al., *Nature* 319:230–234 (1986) (GenBank accession number Xo3363), and is shown in FIGS. 2 and 3. ErbB2 comprises four domains (Domains 1–4). HER2 polypeptides from other non-human animal, e.g. mammalian species are also well known in the art. "Functional derivatives" include amino acid sequence variants, and covalent derivatives of the native polypeptides as long as they retain a qualitative biological activity of the corresponding native polypeptide. Amino acid sequence variants generally differ from a native sequence in the substitution, deletion and/or insertion of one or more amino acids anywhere within a native amino acid sequence. Deletional variants include fragments of the native polypeptides, and variants having N- and/or C-terminal truncations.

"Heregulin" (HRG) when used herein refers to a polypeptide which activates the ErbB2-ErbB3 and ErbB2-ErbB4 protein complexes (i.e. induces phosphorylation of tyrosine residues in the complex upon binding thereto). Various heregulin polypeptides encompassed by this term are disclosed in Holmes et al., *Science* 256:1205–1210 (1992); WO 92/20798; Wen et al., *Mol. Cell. Biol.* 14(3):1909–1919 (1994) and Marchionni et al., *Nature* 362:312–318 (1993), for example. The term includes biologically active fragments and/or variants of a naturally occurring HRG polypeptide, such as an EGF-like domain fragment thereof (e.g. $HRGB\beta_{177-244}$).

In the context of HER2 fragments, the phrase "having the biological activity of a native human HER2" is used to refer to the qualitative ability of such fragments to induce tumor growth when overexpressed in an animal model (transgenic or non-transgenic) of the present invention.

The term "nucleic acid" refers to polynucleotides such as deoxyribonucleic acid (DNA), and, where appropriate, ribonucleic acid (RNA). The term also includes, as equivalents, analogs of either DNA or RNA made from nucleotide analogs, and as applicable, single (sense or antisense) and double-stranded polynucleotides. An "isolated" nucleic acid molecule is a nucleic acid molecule that is identified and separated from at least one contaminant nucleic acid molecule with which it is ordinarily associated in the natural source of the nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

As used herein, the term "vector" refers to a nucleic acid molecule capable of transporting another nucleic acid to which it has been linked. The term "expression vector" includes plasmids, cosmids or phages capable of synthesizing the subject HER2 protein encoded by the respective recombinant gene carried by the vector. Preferred vectors are those capable of autonomous replication and/or expression of nucleic acids to which they are linked. In the present specification, "plasmid" and "vector" are used interchangeably, as the plasmid is the most commonly used form of vector.

As used herein, the terms "transcriptional regulatory elements" and "transcriptional regulatory sequences" are used interchangeably and refer to nucleic acid, e.g. DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, enhancers, splicing signals and polyadenylation signals. These terms are intended to encompass all elements that promote or regulate transcription, including promoters, core elements required for basic interaction of RNA polymerase and transcription factors, upstream elements, enhancers, and response elements (Lewin, "Genes V" (Oxford University Press, Oxford) pages 847–873). Reference herein to the transcriptional regulatory elements of a gene or class of gene includes both all or an intact region of the naturally occurring transcriptional regulatory elements and modified forms of the transcriptional regulatory elements of the gene or group of genes. Such modified forms include rearrangements of the elements, deletions of some elements or extraneous sequences, and insertion of heterologous elements. The modular nature of transcriptional regulatory elements and the absence of position-dependence of the function of some regulatory elements such as enhancers make such modifications possible. Numerous techniques are available for dissecting the regulatory elements of genes to determine their location and function. Such information can be used to direct modification of the elements, if desired. It is preferred, however, that an intact region of the transcriptional regulatory elements of a gene be used.

The term "tissue-specific promoter" means a nucleotide sequence that serves as a promoter, i.e., regulates expression of a selected DNA sequence operably linked to the promoter, and which effects expression of the selected DNA sequence in specific cells of a tissue, such as cells of a mammary gland. In an illustrative embodiment, gene constructs utilizing mammary gland-specific promoters can be used to preferentially direct expression of a HER2 protein or protein fragment in the mammary gland tissue.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "transfection" refers to the introduction of a nucleic acid, e.g., an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of HER2.

As used herein, the term "transgene" refers to a nucleic acid sequence which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can be operably linked to one or more transcriptional regulatory sequences and any other nucleic acid, such as introns, that may be necessary for optimal expression of a selected nucleic acid.

Accordingly, the term "transgene construct" refers to a nucleic acid which includes a transgene, and (optionally) such other nucleic acid sequences as transcriptionally regulatory sequence, polyadenylation sites, replication origins, marker genes, etc., which may be useful in the general manipulation of the transgene for insertion in the genome of a host organism.

The term "transgenic" is used herein as an adjective to describe the property, for example, of an animal or a construct, of harboring a transgene. For instance, as used herein, a "transgenic organism" is any animal, preferably a non-human mammal, in which one or more of the cells of the animal contain heterologous nucleic acid introduced by way of human intervention, such as by trangenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical crossbreeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express or overexpress a recombinant form of the subject HER2 proteins. The terms "founder line" and "founder animal" refer to those animals that are the mature product of the embryos to which the transgene was added, i.e., those animals that grew from the embryos into which DNA was inserted, and that were implanted into one or more surrogate hosts.

The terms "progeny" and "progeny of the transgenic animal" refer to any and all offspring of every generation subsequent to the originally transformed mammals. The term "non-human mammal" refers to all members of the class Mammalia except humans. "Mammal" refers to any animal classified as a mammal, including humans, domestic and farm animals, and zoo, sports, or pet animals, such as mouse, rat, rabbit, pig, sheep, goat, cattle and higher primates.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

The term "antibody" herein is used in the broadest sense and specifically covers intact monoclonal antibodies, polyclonal antibodies, multispecific antibodies (e.g. bispecific antibodies) formed from at least two intact antibodies, and antibody fragments, so long as they exhibit the desired biological activity.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature, 256:495 (1975), or may be made by recombinant DNA methods (see, e.g., U.S. Pat. No. 4,816,567). The "monoclonal antibodies" may also be isolated from phage antibody libraries using the techniques described in Clackson et al., Nature, 352:624–628 (1991) and Marks et al., J. Mol. Biol., 222:581–597 (1991), for example.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA, 81:6851–6855 (1984)). Chimeric antibodies of interest herein include primatized antibodies comprising variable domain antigen-binding sequences derived from a non-human primate (e.g. Old World Monkey, Ape etc) and human constant region sequences.

"Antibody fragments" comprise a portion of an intact antibody, preferably comprising the antigen-binding or variable region thereof. Examples of antibody fragments include Fab, Fab', F(ab')$_2$, and Fv fragments; diabodies; linear antibodies; single-chain antibody molecules; and multispecific antibodies formed from antibody fragment(s).

An "intact" antibody is one which comprises an antigen-binding variable region as well as a light chain constant domain ($C_L$) and heavy chain constant domains, $C_H1$, $C_H2$ and $C_H3$. The constant domains may be native sequence constant domains (e.g. human native sequence constant domains) or amino acid sequence variant thereof. Preferably, the intact antibody has one or more effector functions.

"Humanized" forms of non-human (e.g., rodent) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522–525 (1986); Riechmann et al., Nature 332:323–329 (1988); and Presta, Curr. Op. Struct. Biol. 2:593–596 (1992).

Humanized anti-ErbB2 antibodies include huMAb4D5-1, huMAb4D5-2, huMAb4D5-3, huMAb4D5-4, huMAb4D5-5, huMAb4D5-6, huMAb4D5-7 and huMAb4D5-8 (HERCEPTIN7) as described in Table 3 of U.S. Pat. 5,821,337 expressly incorporated herein by reference; humanized 520C9 (WO93/21319) and humanized 2C4 antibodies as described hereinbelow.

A molecule which "induces cell death" is one which causes a viable cell to become nonviable. The cell is generally one which expresses the ErbB2 receptor, especially where the cell overexpresses the ErbB2 receptor. Preferably, the cell is a cancer cell, e.g. a breast, ovarian, stomach, endometrial, salivary gland, lung, kidney, colon, thyroid, pancreatic, prostate or bladder cancer cell. In vitro, the cell may be a SK-BR-3, BT474, Calu 3, MDA-MB-453, MDA-MB-361 or SKOV3 cell. Cell death in vitro may be determined in the absence of complement and immune effector cells to distinguish cell death induced by antibody-dependent cell-mediated cytotoxicity (ADCC) or complement dependent cytotoxicity (CDC). Thus, the assay for cell death may be performed using heat inactivated serum (i.e. in the absence of complement) and in the absence of immune effector cells. To determine whether the molecule is able to induce cell death, loss of membrane integrity as evaluated by uptake of propidium iodide (PI), trypan blue (see Moore et al. *Cytotechnology* 17:1–11 (1995)) or 7AAD can be assessed relative to untreated cells. Preferred cell death-inducing antibodies are those which induce PI uptake in the PI uptake assay in BT474 cells (see below).

A molecule which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). The cell is usually one which overexpresses the ErbB2 receptor. Preferably the cell is a tumor cell, e.g. a breast, ovarian, stomach, endometrial, salivary gland, lung, kidney, colon, thyroid, pancreatic, prostate or bladder cancer cell. In vitro, the cell may be a SK-BR-3, BT474, Calu 3 cell, MDA-MB-453, MDA-MB-361 or SKOV3 cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. Preferably, the molecule which induces apoptosis is one which results in about 2 to 50 fold, preferably about 5 to 50 fold, and most preferably about 10 to 50 fold, induction of annexin binding relative to untreated cell in an annexin binding assay using BT474 cells. Sometimes the pro-apoptotic molecule will be one which further blocks ErbB ligand activation of an ErbB receptor. In other situations, the molecule is one which does not significantly block ErbB ligand activation of an ErbB receptor. Further, the molecule may induce apoptosis, without inducing a large reduction in the percent of cells in S phase (e.g. one which only induces about 0–10% reduction in the percent of these cells relative to control).

A tumor which "does not respond, or responds poorly, to treatment with a monoclonal anti-ErbB antibody" does not show statistically significant improvement in response to anti-ErbB antibody treatment when compared to no treatment or treatment with placebo in a recognized animal model or a human clinical trial, or which responds to initial treatment with anti-ErbB antibodies but grows as treatment is continued. A particularly suitable animal model for testing the efficacy of anti-ErbB antibodies is the transgenic animal model disclosed herein, and illustrated in Example 3.

The terms "treat" or "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

A "disorder" is any condition that would benefit from treatment with a molecule identified using the transgenic animal model of the present invention. This includes chronic and acute disorders or diseases including those pathological conditions which predispose the mammal to the disorder in question. Non-limiting examples of disorders to be treated herein include benign and malignant tumors; leukemias and lymphoid malignancies, in particular breast, ovarian, stomach, endometrial, salivary gland, lung, kidney, colon, thyroid, pancreatic, prostate or bladder cancer. A preferred disorder to be treated in accordance with the present invention is malignant breast tumor that does not respond or responds poorly to other treatments, such as HERCEPTIN® therapy.

The term "therapeutically effective amount" refers to an amount of a drug effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can, for example, be measured by assessing the time to disease progression (TTP) and/or determining the response rate (RR).

"Tumor", as used herein, refers to all neoplastic cell growth and proliferation, whether malignant or benign, and all pre-cancerous and cancerous cells and tissues.

The terms "cancer" and "cancerous" refer to or describe the physiological condition in mammals that is typically characterized by unregulated cell growth. Examples of cancer include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

An "ErbB-expressing cancer" is one comprising cells which have ErbB protein present at their cell surface. An "ErbB2-expressing cancer" is one which produces sufficient levels of ErbB2 at the surface of cells thereof, such that an anti-ErbB2 antibody can bind thereto and have a therapeutic effect with respect to the cancer.

A cancer "characterized by excessive activation" of an ErbB receptor is one in which the extent of ErbB receptor activation in cancer cells significantly exceeds the level of activation of that receptor in non-cancerous cells of the same tissue type. Such excessive activation may result from overexpression of the ErbB receptor and/or greater than normal levels of an ErbB ligand available for activating the ErbB receptor in the cancer cells. Such excessive activation may cause and/or be caused by the malignant state of a cancer cell.

A cancer which "overexpresses" an ErbB receptor is one which has significantly higher levels of an ErbB receptor, such as HER2, at the cell surface thereof, compared to a noncancerous cell of the same tissue type. Such overexpression may be caused by gene amplification or by increased transcription or translation. ErbB receptor overexpression may be determined in a diagnostic or prognostic assay by evaluating increased levels of the ErbB protein present on the surface of a cell (e.g. via an immunohistochemistry assay; IHC). Alternatively, or additionally, one may measure levels of ErbB-encoding nucleic acid in the cell, e.g. via fluorescent in situ hybridization (FISH; see WO98/45479 published October, 1998), Southern blotting, or polymerase chain reaction (PCR) techniques, such as real time quantitative PCR (RT-PCR). One may also study ErbB receptor overexpression by measuring shed antigen (e.g., ErbB extracellular domain) in a biological fluid such as serum (see, e.g., U.S. Pat. No. 4,933,294 issued Jun. 12, 1990; WO91/05264 published Apr. 18, 1991; U.S. Pat. No. 5,401,638 issued Mar. 28, 1995; and Sias et al. *J. Immunol. Methods* 132: 73–80 (1990)). Aside from the above assays, various in vivo assays are available to the skilled practitioner. For example, one may expose cells within the body of the patient to an antibody which is optionally labeled with a detectable label, e.g. a radioactive isotope, and binding of the antibody to cells in the patient can be evaluated, e.g. by external scanning for radioactivity or by analyzing a biopsy taken from a patient previously exposed to the antibody.

The tumors overexpressing HER2 are rated by immunohistochemical scores corresponding to the number of copies of HER2 molecules expressed per cell, and can been determined biochemically: 0=0–10,000 copies/cell, 1+=at least about 200,000 copies/cell, 2+=at least about 500,000 copies/cell, 3+=at least about 2,000,000 copies/cell. Overexpression of HER2 at the 3+level, which leads to ligand-independent activation of the tyrosine kinase (Hudziak et al., *Proc. Natl. Acad. Sci. USA* 84: 7159–7163 [1987]), occurs in approximately 30% of breast cancers, and in these patients, relapse-free survival and overall survival are diminished (Slamon et al., *Science* 244: 707–712 [1989]; Slamon et al., *Science* 235: 177–182 [1987]).

Conversely, a cancer which is "not characterized by overexpression of the ErbB2 receptor" is one which, in a diagnostic assay, does not express higher than normal levels of ErbB2 receptor compared to a noncancerous cell of the same tissue type.

A tumor which "does not respond, or responds poorly, to treatment with a monoclonal anti-ErbB antibody" does not show statistically significant improvement in response to anti-ErbB antibody treatment when compared to no treatment or treatment with placebo in a recognized animal model or a human clinical trial, or which responds to initial treatment with anti-ErbB antibodies but grows as treatment is continued. A particularly suitable animal model for testing the efficacy of anti-ErbB antibodies is the transgenic animal model disclosed herein.

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins such as small molecule toxins or enzymatically active toxins of bacterial, fungal, plant or animal origin, including fragments and/or variants thereof.

A "chemotherapeutic agent" is a chemical compound useful in the treatment of cancer. Examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK7; razoxane; sizofiran; spirogermnanium; tenuazonic acid; triaziquone; 2,2',2'=-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL7, Bristol-Myers Squibb Oncology, Princeton, N.J.) and doxetaxel (TAXOTERE7, Rhône-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; and pharmaceutically acceptable salts, acids or derivatives of any of the above.

The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wilman, "Prodrugs in Cancer Chemotherapy" *Biochemical Society Transactions*, 14, pp. 375–382, 615th Meeting Belfast (1986) and Stella et al., "Prodrugs: A Chemical Approach to Targeted Drug Delivery," *Directed Drug Delivery*, Borchardt et al., (ed.), pp. 247–267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

A "liposome" is a small vesicle composed of various types of lipids, phospholipids and/or surfactant which is useful for delivery of a drug (such as the anti-ErbB2 antibodies disclosed herein and, optionally, a chemotherapeutic agent) to a mammal. The components of the liposome are commonly arranged in a bilayer formation, similar to the lipid arrangement of biological membranes.

A "small molecule" is defined herein to have a molecular weight below about 500 Daltons.

II. Detailed Description i. General Method of Making Transgenic Non-human Mammals

The transgenic animals of the present invention all include within a plurality of their cells a transgene of the present invention, which transgene alters the phenotype of the "host cell" with respect to regulation of cell growth in mammary glands so as to give rise to tumors. Various aspects of transgenic animal technology are well known in the art, and are described in detail in literature, such as Hogan et al., Manipulating the Mouse Embryo (Cold Spring Harbor Laboratory, Cold Spring Harbor, N.Y., [1986]). Although the making of transgenic animals is illustrated herein with reference to transgenic mice, this is only for illustrative purpose, and is not to be construed as limiting the scope of the invention. This specific disclosure can be readily adapted by those skilled in the art to incorporate HER2 transgene sequences into any non-human mammal utilizing the methods and materials described below. Animals suitable for transgenic experiments can be obtained from standard commercial sources such as Taconic (Germantown, N.Y.).

A. Transgene Construct

Construction of transgenes can be accomplished using any suitable genetic engineering techniques well known in the art, including, without limitation, the standard techniques of restriction endonuclease digestion, ligation, transformation, plasmid purification, DNA sequencing etc as described in Sambrook et al., Molecular Cloning: A Laboratory Manual (Cold Spring Harbor Laboratory, N.Y., (1989)).

The transgenes of the present invention are typically operably linked to transcriptional regulatory sequences, such as promoters and/or enhancers, to regulate expression of the transgene in a particular manner. In certain embodiments, the useful transcriptional regulatory sequences are those that are highly regulated with respect to activity, both temporally and spatially. Thus, the promoters of choice can be those that are active only in particular tissues or cell types. Promoters/enhancers which may be used to control the expression of the transgene in vivo include, but are not limited to, the human cytomegalovirus (CMV) promoter/enhancer (Karasuyama et al.,*J. Exp. Med.* 169: 13 [1989]), the human β-actin promoter (Gunning et al., *Proc. Natl. Acad. Sci. USA* 84: 4831–4835 [1987]), the glucocorticoid-inducible promoter present in the mouse mammary tumor virus long terminal repeat (MMTV LTR) (Kiessig et al., *Mol. Cell Biol.* 4: 1354–1362 [1984]), the long terminal repeat sequences of Moloney murine leukemia virus (MuLV LTR) (Weiss et al. [1985] RNA Tumor Viruses, Cold Spring Harbor Laboratory, Cold Spring Harbor, N.Y.), the SV40 early or late region promoter (Benoist et al. *Nature* 290: 304–310 [1981]; Templeton et al. *Mol. Cell Biol.*, 4: 817 [1984]; and Sprague et al., *J. Virol.*, 45: 773 [1983]), the promoter contained in the 3' long terminal repeat of Rous sarcoma virus (RSV) (Yamamoto et al., *Cell* 22: 787–797 [1980]), the herpes simplex virus (HSV) thymidine kinase promoter/enhancer (Wagner et al. *Proc. Natl. Acad. Sci. USA* 82: 3567–71 [1981]), metallothionein (MT) promoter (Palmiter et al., *Nature* 300: 611–615 [1982]), and the herpes simplex virus LAT promoter (Wolfe et al. *Nature Genetics* 1: 379–384 [1992]).

In addition to the transgene and the transcriptional regulatory sequence, the vectors useful for preparing the transgenes of this invention typically contain one or more other elements useful for optimizing expression of the transgene in the host animal. Thus, the transgene construct may include transcription termination elements, such as to direct polyadenylation of an mRNA transcript, as well as intronic sequences. For example, the transgene can be flanked at its 3' end by SV40 sequences (SV40 intron/pA) which add the transcription termination and polyadenylation signals to the transgene transcript. In yet other embodiments, the transgene can include intron sequences. In many instances, the expression of a transgene is increased by the presence of one or more introns in the coding sequence.

In still other embodiments, the transgene construct may include additional elements which facilitate its manipulation in cells (e.g., in bacterial cells) prior to insertion in the intended recipient cell. For instance, the vector may include origin of replication elements for amplification in prokaryotic cells. Moreover, the transgene construct may contain selectable markers for isolating cells, either from the recipient animal, or cells generated as intermediate in making the transgenic animal (i.e., bacterial cells used for amplifying the construct or ES cells used for introducing the transgene). Selectable marker genes may encode proteins necessary for the survival and/or growth of transfected cells under selective culture conditions. Typical selection marker genes encode proteins that, for example: (i) confer resistance to antibiotics or other toxins, e.g., ampicillin, tetracycline or kanomycin for prokaryotic host cells, and neomycin, hygromycin or methotrexate for mammalian cells; or (ii) complement auxotrophic deficiencies of the cell.

B. Cells Used for Introduction of Transgene

In an exemplary embodiment, the "transgenic non-human mammals" of the invention are produced by introducing HER2 transgene into the germline of the non-human mammal. Embryonal target cells at various developmental stages can be used to introduce HER2 transgene. Different methods are used depending on the stage of development of the embryonal target cell. The specific line(s) of any animal used to practice this invention are selected for general good health, good embryo yields, good pronuclear visibility in the embryo, and good reproductive fitness.

In one embodiment, the transgene construct is introduced into a single stage embryo. Generally, the female animals are superovulated by hormone treatment, mated and fertilized eggs are recovered. For example, in case of mice, females six weeks of age are induced to superovulate with a 5 IU injection (0.1 ml, i.p.) of pregnant mare serum gonadotropin (PMSG; Sigma) followed 48 hours later by a 5 IU injection (0.1 ml, i.p.) of human chorionic gonadotropin (hCG; Sigma). FVB strain of mice are used in this case. Females are then mated immediately with a stud male overnight. Such females are next examined for copulation plugs. Those that have mated are euthenized by $CO_2$ asphyxiation or cervical dislocation and embryos are recovered from excised oviducts and placed in Dulbecco's phosphate buffered saline with 0.5% bovine serum albumin (BSA; Sigma). Surrounding cumulus cells are removed with hyaluronidase (1 mg/ml). Pronuclear embryos are then washed and placed in Earle's balanced salt solution containing 0.5% BSA (EBSS) in a 37.5° C. incubator with a humidified atmosphere at 5% $CO_2$, 95% air until the time of injection.

Normally, fertilized embryos are incubated in suitable media until the pronuclei appear. At about this time, the transgene is introduced into the female or male pronucleus as described below. In some species such as mice, the male pronucleus is preferred. For example, the exogenous genetic material is added to the early male pronucleus, as soon as possible after the formation of the male pronucleus, which is when the male and female pronuclei are well separated and both are located close to the cell membrane. Alternatively, the exogenous genetic material could be added to the nucleus of the sperm after it has been induced to undergo decondensation. Sperm containing the exogenous genetic material can then be added to the ovum or the decondensed sperm could be added to the ovum with the transgene constructs being added as soon as possible thereafter.

In addition to similar biological considerations, physical ones also govern the amount (e.g., volume) of exogenous genetic material, which can be added to the nucleus of the zygote, or to the genetic material which forms a part of the zygote nucleus. Generally, the volume of exogenous genetic material inserted will not exceed about 10 picoliters. The physical effects of addition must not be so great as to physically destroy the viability of the zygote. The biological limit of the number and variety of DNA sequences will vary depending upon the particular zygote and functions of the exogenous genetic material and will be readily apparent to one skilled in the art, because the genetic material, including the exogenous genetic material, of the resulting zygote must be biologically capable of initiating and maintaining the differentiation and development of the zygote into a functional organism.

The number of copies of the transgene constructs which are added to the zygote is dependent upon the total amount of exogenous genetic material added and will be the amount which enables the genetic transformation to occur. Theoretically only one copy is required; however, generally, numerous copies are utilized, for example, 1,000–20,000 copies of the transgene construct, in order to insure that one copy is functional.

C. Methods of Introducing Transgene

Each transgene construct to be inserted into the cell must first be in the linear form since the frequency of recombination is higher with linear molecules of DNA as compared to the circular molecules. Therefore, if the construct has been inserted into a vector, linearization is accomplished by digesting the DNA with a suitable restriction endonuclease selected to cut only within the vector sequence and not within the transgene sequence.

Introduction of the transgene into the embryo may be accomplished by any means known in the art so long as it is not destructive to the cell, nuclear membrane or other existing cellular or genetic structures. Some of the widely used methods include microinjection, electroporation, or lipofection. Following introduction of the transgene, the embryo may be incubated in vitro for varying amounts of time, or reimplanted into the surrogate host, or both. One common method is to incubate the embryos in vitro for about 1–7 days, depending on the species, and then reimplant them into the surrogate host.

The zygote is the best target for introducing the transgene construct by microinjection method. In the mouse, the male pronucleus reaches the size of approximately 20 micrometers in diameter which allows reproducible injection of 1–2 pl of DNA solution. The use of zygotes as a target for gene transfer has a major advantage in that in most cases the injected DNA will be incorporated into the host gene before the first cleavage (Brinster et al. *Proc. Natl. Acad. Sci. USA* 82: 4438–4442 [1985]). As a consequence, all cells of the transgenic animal will carry the incorporated transgene. This will in general also be reflected in the efficient transmission of the transgene to offspring of the founder since 50% of the germ cells will harbor the transgene.

Retroviral infection can also be used to introduce transgene into a non-human mammal. The developing non-human embryo can be cultured in vitro to the blastocyst stage. During this time, the blastomeres can be targets for retroviral infection (Jaenich, R. *Proc. Natl. Acad. Sci. USA* 73: 1260–1264 [1976]). Efficient infection of the blastomeres is obtained by enzymatic treatment to remove the zona pellucida (Manipulating the Mouse Embryo, Hogan eds., Cold Spring Harbor Laboratory Press, Cold Spring Harbor, [1986]). The viral vector system used to introduce the transgene is typically a replication-defective retrovirus carrying the transgene (Jahner et al. *Proc. Natl. Acad. Sci. USA* 82: 6927–6931 [1985]; Van der Putten et al. *Proc. Natl. Acad. Sci. USA* 82: 6148–6152 [1985]). Transfection is easily and efficiently obtained by culturing the blastomeres on a monolayer of virus-producing cells (Van der Putten, supra; Stewart et al. *EMBO J.* 6: 383–388 [1987]). Alternatively, infection can be performed at a later stage. Virus or virus-producing cells can also be injected into the blastocoele (Jahner et al. *Nature* 298: 623–628 [1982]). Most of the founders will be mosaic for the transgene since incorporation occurs only in a subset of the cells which formed the transgenic animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1982) supra).

Insertion of the transgene construct into the ES cells can be accomplished using a variety of methods well known in the art including for example, electroporation, microinjection, and calcium phosphate treatment. A preferred method of insertion is electroporation, in which the ES cells and the transgene construct DNA are exposed to an electric pulse using an electroporation machine and following the manufacturer's guidelines for use. After electroporation, the ES cells are typically allowed to recover under suitable incubation conditions. The cells are then screened for the presence of the transgene.

D. Implantation of Embryos

Pseudopregnant, foster or surrogate mothers are prepared for the purpose of implanting embryos, which have been modified by introducing the transgene. Such foster mothers are typically prepared by mating with vasectomized males of the same species. The stage of the pseudopregnant foster mother is important for successful implantation, and it is species dependent. For mice, this stage is about 2–3 days pseudopregnant. Recipient females are mated at the same time as donor females. Although the following description relates to mice, it can be adepted for any other non-human mammal by those skilled in the art. At the time of embryo transfer, the recipient females are anesthetized with an intraperitoneal injection of 0.015 ml of 2.5% avertin per gram of body weight. The oviducts are exposed by a single midline dorsal incision. An incision is then made through the body wall directly over the oviduct. The ovarian bursa is then torn with watchmaker's forceps. Embryos to be transferred are placed in DPBS (Dulbecco's phosphate buffered saline) and in the tip of a transfer pipet (about 10 to 12 embryos). The pipet tip is inserted into the infundibulum and the embryos transferred. After the transfer, the incision is closed by two sutures. The number of embryos implanted into a particular host will vary by species, but will usually be comparable to the number of off spring the species naturally produces.

Where the ES cell have been used to introduce the transgene, the transformed ES cells are incorporated into the embryo as described earlier, and the embryos may be implanted into the uterus of a pseudopregnant foster mother for gestation.

E. Screening for the Presence or Expression of Transgene

Transgenic offspring of the surrogate host may be screened for the presence and/or expression of the transgene by any suitable method. Offspring that are born to the foster mother may be screened initially for mosaic coat color where the coat color selection strategy (as described above) has been employed. Alternatively, or additionally, screening is often accomplished by Southern blot or PCR of DNA prepared from tail tissue, using a probe that is complementary to at least a portion of the transgene. Western blot analysis or immunohistochemistry using an antibody against the protein encoded by the transgene may be employed as an alternative or additional method for screening for the presence of the transgene product. Alternatively, the tissues or cells believed to express the transgene at the highest levels are tested for the RNA expression of the transgene using Northern analysis or RT-PCR.

Alternative or additional methods for evaluating the presence of the transgene include, without limitation, suitable biochemical assays such as enzyme and/or immunological assays, histological stains for particular marker or enzyme activities, flow cytometric analysis, and the like. Analysis of the blood may also be useful to detect the presence of the transgene product in the blood, as well as to evaluate the effect of the transgene on the levels of various types of blood cells and other blood constituents.

F. Breeding of the Transgenic Animals

Progeny of the transgenic animals may be obtained by mating the transgenic animal with a suitable partner, or by in vitro fertilization of eggs and/or sperm obtained from the transgenic animal. Where mating with a partner is to be performed, the partner may or may not be transgenic; where it is transgenic, it may contain the same or a different transgene, or both. Alternatively, the partner may be a parental line. Where in vitro fertilization is used, the fertilized embryo may be implanted into a surrogate host or incubated in vitro, or both. Using either method, the progeny may be evaluated for the presence of the transgene using methods described above, or other appropriate methods. Typically, crossing and backcrossing is accomplished by mating siblings or a parental strain with an offspring, depending on the goal of each particular step in the breeding process.

G. Non-trangenic Animal Model to Evaluate HER2-directed Therapies

HER2-directed therapies can also be tested in non-transgenic non-human mammals bearing HER2-expressing tumors. Such animals may be obtained by transplanting tumors from the transgenic non-human mammals herein into suitable recipients, such as mice or other non-human mammals. In particular, a HER2-overexpressing tumor developed in a transgenic non-human mammal disclosed herein may be surgically removed, and transplanted into recipient animals, e.g. mice. In order to enhance the incidence of tumors and the speed of tumor development, it might be advantageous to pass tumors into further recipients by similar surgical techniques or other methods well known in the art. Such non-transgenic, tumor-bearing mammals serve as an animal model for testing HER2-directed therapies, such as treatment of HER2-overexpressing tumors that do not respond or respond poorly to traditional treatments (e.g. radiation and/or chemotherapy) as well as to treatment with anti-HER2 antibodies, such as HERCEPTIN®.

H. Cell Lines and Cell Cultures

The animals of this invention can be used as a source of cells, differentiated or precursor, which can be immortalized in cell culture. Cells in which the abnormal function of the overexpressed non-mutated HER2 protein gives rise to breast tumors may be isolated from the animal and established in vitro as cell lines and used for screening of various compounds for potential activity directed against HER2. Thus, the transgenic animals of this invention can be used as a source of cells for cell culture. Tissues of transgenic mice are analyzed for the presence and/or expression of the HER2 transgene as hereinbefore described, and cells or tissues carrying the gene are cultured, using standard tissue culture techniques, e.g., to study the function and development of cancer cells, and to screen for drug candidates potentially useful in the treatment of diseases or conditions associated with the overexpression of HER2.

ii. Screening for Compounds Directed Against HER2

The transgenic non-human mammals, their progeny, the non-transgenic tumor-bearing animals, and cell lines of the present invention provide several important uses that will be readily apparent to one of ordinary skill in the art. The transgenic animals and cell lines are particularly useful in screening compounds that have potential as prophylactic or therapeutic treatments of diseases or disorders involving overexpression of HER2. Screening for a useful drug involves administering the candidate drug over a range of doses to the transgenic animal, and assaying at various time points for the effect(s) of the drug on the disease or disorder being evaluated. Alternatively, or additionally, the drug can be administered prior to or simultaneously with exposure to an inducer of the disease, if applicable.

In one embodiment, candidate compounds are screened by being administered to the transgenic animal over a range of doses, and evaluating the animal's physiological response to the compounds over time. Administration may be oral, or by suitable injection, depending on the chemical nature of the compound being evaluated. In some cases, it may be appropriate to administer the compound in conjunction with co-factors that would enhance the efficacy of the compound. If cell lines derived from the subject transgenic animals are used to screen for compounds useful in treating various disorders associated with HER2-overexpression, the test compounds are added to the cell culture medium at an appropriate time, and the cellular response to the compound is evaluated over time using the appropriate biochemical and/or histological assays. In some cases, it may be appropriate to apply the compound of interest to the culture medium in conjunction with co-factors that would enhance the efficacy of the compound.

Thus, the present invention provides assays for identifying agents which are antagonists of the abnormal cellular function of the overexpressed HER2 protein in the pathogenesis of cellular proliferation and/or differentiation of mammary gland that is causally related to the development of breast tumors.

In addition to screening a drug for use in treating a disease or condition, the transgenic animals of the present invention are also useful in designing a therapeutic regimen aimed at preventing or curing the disease or condition. For example, the animal may be treated with a combination of a particular diet, exercise routine, radiation treatment, chemotherapy and/or one or more compounds identified herein either prior to, simultaneously, or after the onset of the disease or condition. Such an overall therapy or regimen might be more effective at combating the disease or condition than treatment with a compound alone.

Agents to be tested in the animals and cell cultures of the present invention can be produced, for example, by bacteria, yeast or other organisms (e.g. natural products), produced chemically (e.g. small molecules, including peptidomimetics), or by techniques of recombinant DNA technology.

To identify a compound which blocks ligand activation of an ErbB (e.g. ErbB2) receptor, the ability of the compound to block ErbB ligand binding to cells expressing the ErbB (ErbB2) receptor (e.g. in conjugation with another ErbB receptor with which the ErbB receptor of interest forms an ErbB hetero-oligomer) may be determined. For example, cells isolated from the transgenic animal overexpressing HER2 and transfected to express another ErbB receptor (with which HER2 forms hetero-oligomer) may be incubated with the compound and then exposed to labeled ErbB ligand. The ability of the compound to block ligand binding to the ErbB receptor in the ErbB hetero-oligomer may then be evaluated.

For example, inhibition of heregulin (HRG) binding to breast tumor cell lines, overexpressing HER2 and established from the transgenic non-human mammals (e.g. mice) herein, by the candidate compounds may be performed using monolayer cultures on ice in a 24-well-plate format. Anti-ErbB2 monoclonal antibodies may be added to each well and incubated for 30 minutes. $^{125}$I-labeled rHRGβ1$_{177-224}$ (25,000 cpm) may then be added, and the incubation may be continued for 4 to 16 hours. Dose response curves may be prepared and an IC$_{50}$ value may be calculated for the compound of interest.

Alternatively, or additionally, the ability of a drug candidate to block ErbB ligand-stimulated tyrosine phosphorylation of an ErbB receptor present in an ErbB hetero-oligomer may be assessed. For example, cell lines established from the transgenic animals herein may be incubated with a test compound and then assayed for ErbB ligand-dependent tyrosine phosphorylation activity using an anti-phosphotyrosine monoclonal antibody (which is optionally conjugated with a detectable label). The kinase receptor activation assay described in U.S. Pat. No. 5,766,863 is also available for determining ErbB receptor activation and blocking of that activity by the compound.

In one embodiment, one may screen for compounds which inhibit HRG stimulation of p180 tyrosine phosphorylation in MCF7 cells essentially as described below. For example, a cell line established from a HER2-transgenic animal may be plated in 24-well plates and the compound may be added to each well and incubated for 30 minutes at room temperature; then rHRGβ1$_{177-244}$ may be added to each well to a final concentration of 0.2 nM, and the incubation may be continued for 8 minutes. Media may be aspirated from each well, and reactions may be stopped by the addition of 100 μl of SDS sample buffer (5% SDS, 25 mM DTT, and 25 mM Tris-HCl, pH 6.8). Each sample (25 μl) may be electrophoresed on a 4–12% gradient gel (Novex) and then electrophoretically transferred to polyvinylidene difluoride membrane. Antiphosphotyrosine (at 1 μg/ml) immunoblots may be developed, and the intensity of the predominant reactive band at $M_r$–180,000 may be quantified by reflectance densitometry. Some of the well established monoclonal antibodies against HER2 that are known to inhibit HRG stimulation of p180 tyrosine phosphorylation can be used as positive control in this assay. A dose-response curve for inhibition of HRG stimulation of p180 tyrosine phosphorylation as determined by reflectance densitometry may be prepared and an IC$_{50}$ for the compound of interest may be calculated.

One may also assess the growth inhibitory effects of a test compound on cell lines derived from a HER2-transgenic animal, e.g., essentially as described in Schaefer et al. *Oncogene* 15: 1385–1394 (1997). According to this assay, the cells may treated with a test compound at various concentrations for 4 days and stained with crystal violet. Incubation with the compound may show a growth inhibitory effect on this cell line similar to that displayed by monoclonal antibody 2C4 on MDA-MB-175 cells (Schaefer et al., supra). In a further embodiment, exogenous HRG will not significantly reverse this inhibition.

To identify growth inhibitory compounds that specifically target HER2, one may screen for compounds which inhibit the growth of HER2-overexpressing cancer cells derived from the transgenic animals of the present invention. To identify such compounds, the assay described in U.S. Pat. No. 5,677,171 can be performed. According to this assay, HER2 overexpressing cells are grown in a 1:1 mixture of F12 and DMEM. medium supplemented with 10% fetal bovine serum, glutamine and penicillin streptomycin. The cells are plated at 20,000 cells in a 35 mm cell culture dish (2 mls/35mm dish) and the test compound is added at various concentrations. After six days, the number of cells, compared to untreated cells is counted using an electronic COULTER™ cell counter. Those compounds which inhibit cell growth by about 20–100% or about 50–100% may be selected as growth inhibitory compounds.

To select for compounds which induce cell death, loss of membrane integrity as indicated by, e.g., PI, trypan blue or 7AAD uptake may be assessed relative to control. The preferred assay is the PI uptake assay using cells isolated from the breast tumor tissue of the transgenic animal.

According to this assay, the cells are cultured in Dulbecco's Modified Eagle Medium (D-MEM):Ham's F-12 (50:50) supplemented with 10% heat-inactivated FBS (Hyclone) and 2 mM L-glutamine. (Thus, the assay is performed in the absence of complement and immune effector cells). The cells are seeded at a density of 3×106 per dish in 100×20 mm dishes and allowed to attach overnight. The medium is then removed and replaced with fresh medium alone or medium containing various concentrations of the compound. The cells are incubated for a 3-day time period. Following each treatment, monolayers are washed with PBS and detached by trypsinization. Cells are then centrifuged at 1200 rpm for 5 minutes at 4° C., the pellet resuspended in 3 ml ice cold $Ca^{2+}$ binding buffer (10 mM Hepes, pH 7.4, 140 mM NaCl, 2.5 mM $CaCl_2$) and aliquoted into 35 mm strainer-capped 12×75 tubes (1 ml per tube, 3 tubes per treatment group) for removal of cell clumps. Tubes then receive PI (10 µg/ml). Samples may be analyzed using a FACSCAN™ flow cytometer and FACSCONVERT™ CellQuest software (Becton Dickinson). Those compounds which induce statistically significant levels of cell death as determined by PI uptake may be selected as cell death-inducing compounds.

In order to select for compounds which induce apoptosis, an annexin binding assay using cells established from the breast tumor tissue of the transgenic animal is performed. The cells are cultured and seeded in dishes as discussed in the preceding paragraph. The medium is then removed and replaced with fresh medium alone or medium containing 10 µg/ml of the monoclonal antibody. Following a three-day incubation period, monolayers are washed with PBS and detached by trypsinization. Cells are then centrifuged, resuspended in $Ca^{2+}$ binding buffer and aliquoted into tubes as discussed above for the cell death assay. Tubes then receive labeled annexin (e.g. annexin V-FTIC) (1 µg/ml). Samples may be analyzed using a FACSCANT™ flow cytometer and FACSCONVERT™ CellQuest software (Becton Dickinson). Those compounds which induce statistically significant levels of annexin binding relative to control are selected as apoptosis-inducing compounds.

Conjugates of an antibody and one or more small molecule toxins, such as a calicheamicin, a maytansine (U.S. Pat. No. 5,208,020), a trichothene, and CC1065 are also contemplated herein. In one preferred embodiment of the invention, the anti-HER2 antibody is conjugated to one or more maytansine molecules (e.g. about 1 to about 10 maytansine molecules per antibody molecule). Maytansinoids inhibit cell proliferation by inhibiting tubulin polymerization. Maytansine may, for example, be converted to May-SS-Me, which may be reduced to May-SH3 and reacted with modified antibody (Chari et al. *Cancer Research* 52: 127–131 (1992)) to generate a maytansinoid-antibody immunoconjugate. As shown in Example 3, these conjugates have strong anti-tumor activity in the transgenic mouse of the present invention even though the antibody alone (e.g. HERCEPTIN®) does not have significant anti-tumor activity in this model.

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

iii. Follow-up Testing of Molecules Identified in the Transgenic and Non-transgenic Animal Models and Cell-based Assays Herein The drug candidates identified in the animal models and cell-based assays of the present invention can then be further tested in tumor-bearing higher primates and human clinical trials. Human clinical trials can be designed similar to the clinical trials testing the efficacy of the anti-HER2 monoclonal antibody HERCEPTIN® in patients with HER2 overexpressing metastatic breast cancers that had received extensive prior anti-cancer therapy as reported by Baselga et al., *J. Clin. Oncol.* 14:737–744 (1996). The clinical trial may be designed to evaluate the efficacy of a drug candidate in combinations with known therapeutic regimens, such as radiation and/or chemotherapy involing known chemotherapeutic and/or cytotoxic agents.

iv. Pharmaceutical Formulations

Therapeutic formulations of the molecules identifiable or identified by the screening assays of the present invention are prepared for storage by mixing a compound having the desired degree of purity with optional pharmaceutically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol);

low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Preferred lyophilized anti-ErbB2 antibody formulations are described in WO 97/04801, expressly incorporated herein by reference.

The formulations herein may also contain more than one active compound as necessary for the particular indication being treated, preferably those with complementary activities that do not adversely affect each other. For example, it may be desirable to further provide antibodies which bind to EGFR, ErbB2, ErbB3, ErbB4, or vascular endothelial factor (VEGF) in the one formulation. Alternatively, or additionally, the composition may further comprise a chemotherapeutic agent, cytotoxic agent, cytokine, growth inhibitory agent, anti-hormonal agent, and/or cardioprotectant. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The formulations to be used for in vivo administration must be sterile. This is readily accomplished by filtration through sterile filtration membranes.

v. HER2-directed Treatments

It is contemplated that the drug candidates identified in accordance with the present invention, including, without limitation, antibodies, antibody conjugates, polypeptides, peptides, organic and inorganic small molecules, etc. may be used to treat various diseases or disorders characterized by the overexpression of HER2. Exemplary conditions or disorders include benign or malignant tumors; leukemias and lymphoid malignancies; other disorders such as neuronal, glial, astrocytal, hypothalamic, glandular, macrophagal, epithelial, stromal, blastocoelic, inflammatory, angiogenic and immunologic disorders.

Generally, the disease or disorder to be treated is cancer. Examples of cancer to be treated herein include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

The cancer will generally comprise HER2-expressing cells, such that the molecules identified herein are able to bind to the cancer cells. To determine ErbB2 expression in the cancer, various diagnostic/prognostic assays are available. In one embodiment, ErbB2 overexpression may be analyzed by IHC, e.g. using the HERCEPTEST® (Dako). Parrafin embedded tissue sections from a tumor biopsy may be subjected to the IHC assay and accorded a ErbB2 protein staining intensity criteria as follows: Score 0, no staining is observed or membrane staining is observed in less than 10% of tumor cells; Score 1+, a faint/barely perceptible membrane staining is detected in more than 10% of the tumor cells, the cells are only stained in part of their membrane; Score 2+, a weak to moderate complete membrane staining is observed in more than 10% of the tumor cells; Score 3+, a moderate to strong complete membrane staining is observed in more than 10% of the tumor cells.

Those tumors with 0 or 1+ scores for ErbB2 overexpression assessment may be characterized as not overexpressing ErbB2, whereas those tumors with 2+ or 3+ scores may be characterized as overexpressing ErbB2.

Alternatively, or additionally, FISH assays such as the INFORM™ (sold by Ventana, Ariz.) or PATHVISION™ (Vysis, Ill.) may be carried out on formalin-fixed, paraffin-embedded tumor tissue to determine the extent (if any) of ErbB2 overexpression in the tumor.

In one embodiment, the cancer will be one which expresses (and may overexpress) HER2. Examples of cancers which may express/overexpress EGFR include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

The cancer to be treated herein may be one characterized by excessive activation of an ErbB receptor, e.g. HER2. Such excessive activation may be attributable to overexpression or increased production of the ErbB receptor or an ErbB ligand. In one embodiment of the invention, a diagnostic or prognostic assay will be performed to determine whether the patient's cancer is characterized by excessive activation of an ErbB receptor. For example, ErbB gene amplification and/or overexpression of an ErbB receptor in the cancer may be determined. Various assays for determining such amplification/overexpression are available in the art and include the IHC, FISH and shed antigen assays described above. Alternatively, or additionally, levels of an ErbB ligand, such as TGF-α, in or associated with the tumor may be determined according to known procedures. Such assays may detect protein and/or nucleic acid encoding it in the sample to be tested. In one embodiment, ErbB ligand levels in the tumor may be determined using immunohistochemistry (IHC); see, for example, Scher et al. *Clin. Cancer Research* 1:545–550 (1995). Alternatively, or additionally, one may evaluate levels of ErbB ligand-encoding nucleic acid in the sample to be tested; e.g. via FISH, southern blotting, or PCR techniques.

Moreover, ErbB receptor or ErbB ligand overexpression or amplification may be evaluated using an in vivo diagnostic assay, e.g. by administering a molecule (such as an antibody) which binds the molecule to be detected and is tagged with a detectable label (e.g. a radioactive isotope) and externally scanning the patient for localization of the label.

Other therapeutic regimens may be combined with the administration of an anticancer agent identified in accordance with this invention. The combined administration includes coadministration, using separate formulations or a single pharmaceutical formulation, and consecutive administration in either order, wherein preferably there is a time period while both (or all) active agents simultaneously exert their biological activities.

In one embodiment, the treatment of the present invention involves the combined administration of an anticancer agent identified herein, and one or more chemotherapeutic agents or growth inhibitory agents, including coadministration of cocktails of different chemotherapeutic agents, optionally along with treatment with an anti-ErbB2 antibody, such as HERCEPTIN®. Preferred chemotherapeutic agents include taxanes (such as paclitaxel and doxetaxel) and/or anthracycline antibiotics. Preparation and dosing schedules for such chemotherapeutic agents may be used according to manufacturers's instructions or as determined empirically by the skilled practitioner. Preparation and dosing schedules for such chemotherapy are also described in Chemotherapy Service Ed., M.C. Perry, Williams & Wilkins, Baltimore, Md. (1992).

The anticancer agent may be combined with an antihormonal compound; e.g., an anti-estrogen compound such as tamoxifen; an anti-progesterone such as onapristone (see, EP 616 812); or an anti-androgen such as flutamide, in dosages known for such molecules. Where the cancer to be treated is hormone independent cancer, the patient may previously have been subjected to anti-hormonal therapy and, after the cancer becomes hormone independent, the anti-ErbB2 antibody (and optionally other agents as described herein) may be administered to the patient.

Sometimes, it may be beneficial to also coadminister a cardioprotectant (to prevent or reduce myocardial dysfunction associated with the therapy) or one or more cytokines to the patient. In addition to the above therapeutic regimes, the patient may be subjected to surgical removal of cancer cells and/or radiation therapy.

Suitable dosages for any of the above coadministered agents are those presently used and may be lowered due to the combined action (synergy) of the newly identified agent and other chemotherapeutic agents or treatments.

For the prevention or treatment of disease, the appropriate dosage of a molecule identified herein will depend on the type of disease to be treated, as defined above, the severity and course of the disease, whether the molecule is administered for preventive or therapeutic purposes, previous therapy, the patient's clinical history and response to the antibody, and the discretion of the attending physician. The molecule is suitably administered to the patient at one time or over a series of treatments. Depending on the type and severity of the disease, about 1 $\mu$g/kg to 15 mg/kg (e.g. 0.1–20 mg/kg) of molecule is an initial candidate dosage for administration to the patient, whether, for example, by one or more separate administrations, or by continuous infusion. A typical daily dosage might range from about 1 $\mu$g/kg to 100 mg/kg or more, depending on the factors mentioned above. For repeated administrations over several days or longer, depending on the condition, the treatment is sustained until a desired suppression of disease symptoms occurs. A preferred dosing regimen comprises administering an initial loading dose of about 4 mg/kg, followed by a weekly maintenance dose of about 2 mg/kg of the anti-ErbB2 antibody. However, other dosage regimens may be useful. The progress of this therapy is easily monitored by conventional techniques and assays.

Further details of the invention are illustrated in the following non-limiting examples.

EXAMPLE 1

Production and Characterization of Anti-ErbB2 Monoclonal Antibodies

The murine monoclonal antibodies 2C4, 7F3 and 4D5 which specifically bind the extracellular domain of ErbB2 were produced as described in Fendly et al., *Cancer Research* 50:1550–1558 (1990). Briefly, NIH 3T3/HER2-$3_{400}$ cells (expressing approximately $1 \times 10^5$ ErbB2 molecules/cell) produced as described in Hudziak et al *Proc. Natl. Acad. Sci. (USA)* 84:7158–7163 (1987) were harvested with phosphate buffered saline (PBS) containing 25 mM EDTA and used to immunize BALB/c mice. The mice were given injections i.p. of $10^7$ cells in 0.5 ml PBS on weeks 0, 2, 5 and 7. The mice with antisera that immunoprecipitated $^{32}$P-labeled ErbB2 were given i.p. injections of a wheat germ agglutinin-Sepharose (WGA) purified ErbB2 membrane extract on weeks 9 and 13. This was followed by an i.v. injection of 0.1 ml of the ErbB2 preparation and the splenocytes were fused with mouse myeloma line X63-Ag8.653. Hybridoma supernatants were screened for ErbB2-binding by ELISA and radioimmunoprecipitation.

The ErbB2 epitopes bound by monoclonal antibodies 4D5, 7F3 and 2C4 were determined by competitive binding analysis (Fendly et al. *Cancer Research* 50:1550–1558 (1990)). Cross-blocking studies were-done on antibodies by direct fluorescence on intact cells using the PANDEX™ Machine to quantitate fluorescence. Each monoclonal antibody was conjugated with fluorescein isothiocyanate (FITC), using established procedures (Wofsy et al. *Selected Methods in Cellular Immunology*, p. 287, Mishel and Schiigi (eds.) San Francisco: W. J. Freeman Co. (1980)). Confluent monolayers of NIH 3T3/HER2–$3_{400}$ cells were trypsinized, washed once, and resuspended at $1.75 \times 10^6$ cell/ml in cold PBS containing 0.5% bovine serum albumin (BSA) and 0.1% $NaN_3$. A final concentration of 1% latex particles (IDC, Portland, OR) was added to reduce clogging of the PANDEX™ plate membranes. Cells in suspension, 20 $\mu$l, and 20 $\mu$l of purified monoclonal antibodies (100 g/ml to 0.1 $\mu$g/ml) were added to the PANDEX™ plate wells and incubated on ice for 30 minutes. A predetermined dilution of FITC-labeled monoclonal antibodies in 20 $\mu$l was added to each well, incubated for 30 minutes, washed, and the fluorescence was quantitated by the PANDEX™. Monoclonal antibodies were considered to share an epitope if each blocked binding of the other by 50% or greater in comparison to an irrelevant monoclonal antibody control. In this experiment, monoclonal antibodies 4D5, 7F3 and 2C4 were assigned epitopes I, G/F and F, respectively.

The growth inhibitory characteristics of monoclonal antibodies 2C4, 7F3 and 4D5 were evaluated using the breast tumor cell line, SK-BR-3 (see. Hudziak et al. *Molec. Cell. Biol.* 9(3):1165–172 (1989)). Briefly, SK-BR-3 cells were detached by using 0.25% (vol/vol) trypsin and suspended in complete medium at a density of $4 \times 10^5$ cells per ml. Aliquots of 100 $\mu$l ($4 \times 10^4$ cells) were plated into 96-well microdilution plates, the cells were allowed to adhere, and 100 $\mu$l of media alone or media containing monoclonal antibody (final concentration 5 $\mu$g/ml) was then added. After 72 hours, plates were washed twice with PBS (pH 7.5), stained with crystal violet (0.5% in methanol), and analyzed for relative cell proliferation as described in Sugarman et al. *Science* 230:943–945 (1985). Monoclonal antibodies 2C4 and 7F3 inhibited SK-BR-3 relative cell proliferation by about 20% and about 38%, respectively, compared to about 56% inhibition achieved with monoclonal antibody 4D5.

Monoclonal antibodies 2C4, 4D5 and 7F3 were evaluated for their ability to inhibit HRG-stimulated tyrosine phosphorylation of proteins in the Mr 180,000 range from whole-cell lysates of MCF7 cells (Lewis et al. *Cancer Research* 56:1457–1465 (1996)). MCF7 cells are reported to express all known ErbB receptors, but at relatively low levels. Since ErbB2, ErbB3, and ErbB4 have nearly identical molecular sizes, it is not possible to discern which protein is becoming tyrosine phosphorylated when whole-cell lysates are evaluated by Western blot analysis. However, these cells are ideal for HRG tyrosine phosphorylation assays because under the assay conditions used, in the absence of exogenously added HRG, they exhibit low to undetectable levels of tyrosine phosphorylation proteins in the $M_r$ 180,000 range.

MCF7 cells were plated in 24-well plates and monoclonal antibodies to ErbB2 were added to each well and incubated for 30 minutes at room temperature; then rHRGβ1$_{177-244}$was added to each well to a final concentration of 0.2 nM, and the incubation was continued for 8 minutes. Media was carefully aspirated from each well, and reactions were stopped by the addition of 100 μl of SDS sample buffer (5% SDS, 25 mM DTT, and 25 mM Tris-HCl, pH 6.8). Each sample (25 μl) was electrophoresed on a 4–12% gradient gel (Novex) and then electrophoretically transferred to polyvinylidene difluoride membrane. Antiphosphotyrosine (4G10, from UBI, used at 1 μg/ml) immunoblots were developed, and the intensity of the predominant reactive band at $M_r$-180,000 was quantified by reflectance densitometry, as described previously (Holmes et al. *Science* 256:1205–1210 (1992); Sliwkowski et al. *J. Biol. Chem.* 269:14661–14665 (1994))

Monoclonal antibodies 2C4, 7F3, and 4D5, significantly inhibited the generation of a HRG-induced tyrosine phosphorylation signal at $M_r$ 180,000. In the absence of HRG, none of these antibodies were able to stimulate tyrosine phosphorylation of proteins in the $M_r$ 180,000 range. Also, these antibodies do not cross-react with EGFR (Fendly et al. *Cancer Research* 50:1550–1558 (1990)), ErbB3, or ErbB4. Antibodies 2C4 and 7F3 significantly inhibited HRG stimulation of p180 tyrosine phosphorylation to <25% of control. Monoclonal antibody 4D5 was able to block HRG stimulation of tyrosine phosphorylation by –50%.

Inhibition of HRG binding to MCF7 breast tumor cell lines by anti-ErbB2 antibodies was performed with monolayer cultures on ice in a 24-well-plate format (Lewis et al. *Cancer Research* 56:1457–1465 (1996)). Anti-ErbB2 monoclonal antibodies were added to each well and incubated for 30 minutes. $^{125}$I-labeled rHRGPβ1$_{177-224}$ (25,0000 CPM) was added, and the incubation was continued for 4 to 16 hours. After washing the cells to remove unbound labeled protein, cell bound radioactivity was counted. A maximum inhibition of –74% for 2C4 and 7F3 were in agreement with the tyrosine phosphorylation data.

Binding of $^{121}$I-labeled rHRGβ1 could also be significantly inhibited by either 2C4 or 7F3 in various human tumor cell lines, with the exception of the breast cancer cell line MDA-MB-468, which has been reported to express little or no ErbB2. The remaining cell lines are reported to express ErbB2, with the level of ErbB2 expression varying widely among these cell lines.

The growth inhibitory effects of monoclonal antibodies 2C4 and 4D5 on MDA-MB-175 and SK-BR-3 cells in the presence or absence of exogenous rHRGβ1 was assessed (Schaefer et al *Oncogene* 15:1385–1394 (1997)). ErbB2 evels in MDA-MB-175 cells are 4–6 times higher than the level found in normal breast epithelial cells and the ErbB2-ErbB4 receptor is constitutively tyrosine phosphorylated in MDA-MB-175 cells. MDA-MB-175 cells were treated with an anti-ErbB2 monoclonal antibodies 2C4 and 4D5 (10μg/mL) for 4 days. In a crystal violet staining assay, incubation with 2C4 showed a strong growth inhibitory effect on this cell line. Exogenous HRG did not significantly reverse this inhibition. On the other hand 2C4 revealed no inhibitory effect on the ErbB2 overexpressing cell line SK-BR-3. Monoclonal antibody 2C4 was able to inhibit cell proliferation of MDA-MB-175 cells to a greater extent than monoclonal antibody 4D5, both in the presence and absence of exogenous HRG. Inhibition of cell proliferation by 4D5 is dependent on the ErbB2 expression level (Lewis et al. *Cancer Immunol. Immunother.* 37:255–263 (1993)). A maximum inhibition of 66% in SK-BR-3 cells could be detected. However this effect could be overcome by exogenous HRG.

EXAMPLE 2

Transgenic Animals

In order to improve on the clinical activity of HERCEPTIN®, a transgenic HER2 mouse model was developed in which novel HER2-directed therapies could be tested preclinically. Tumors arise readily in transgenic mice that express a mutationally activated form of neu, the rat homolog of HER2, but the HER2 that is overexpressed in breast cancers is not mutated and tumor formation is much less robust in transgenic mice that overexpress nonmutated HER2 (Webster et al., *Semin. Cancer Biol.* 5: 69–76 [1994]). To improve tumor formation with nonmutated HER2, a strategy was used to further enhance overexpression of nonmutated HER2 in a transgenic mouse.

Any promoter that promotes expression of HER2 in epithelial cells in the mouse mammary gland can be used in the disclosed constructs. Many of the milk protein genes are transcribed by promoter/enhancer elements that are specifically active in mammary glands. Milk protein genes include those genes encoding caseins (α-S$_1$ and β), β-lactoglobulin, α-lactalbumin, and whey acidic protein. The ovine β-lactoglobulin promoter is well characterized and widely used in the art (Whitelaw et al., *Biochem J.* 286: 31–39, [1992]). However, similar fragments of promoter DNA from other species are also suitable. A preferred promoter is the promoter derived from the Long Terminal Repeat (LTR) of the Mouse Mammary Tumor Virus (MMTV). A HER2 transgene construct of the present invention was generated using the MMTV LTR promoter (FIG. 1).

To improve tumor formation with nonmutated HER2, we have made transgenic mice using a HER2 cDNA plasmid in which an upstream ATG was deleted in order to prevent initiation of translation at such upstream ATG codons, which would otherwise reduce the frequency of translation initiation from the downstream authentic initiation codon of HER2 (for example, see Child et al., *J. Biol. Chem.* 274: 24335–24341 [1999]). Additionally, a chimeric intron was added to the 5' end, which should also enhance the level of expression as reported earlier (Neuberger and Williams, *Nucleic Acids Res.* 16: 6713 [1988]; Buchman and Berg, *Mol. Cell. Biol.* 8: 4395 [1988]; Brinster et al., *Proc. Natl. Acad. Sci. USA* 85: 836 [1988]). The chimeric intron was derived from a Promega vector, pCI-neo mammalian expression vector (bp 890–1022). The cDNA 3'-end is flanked by human growth hormone exons 4 and 5, and polyadenylation sequences. Moreover, FVB mice were used because this strain is more susceptible to tumor development. The promoter from MMTV-LTR was used to ensure tissue-specific HER2 expression in the mammary gland. Animals were fed the AIN 76A diet in order to increase susceptibility to tumor formation (Rao et al., *Breasr Cancer Res. and Treatment* 45: 149–158 [1997]).

Animals suitable for transgenic experiments can be obtained from standard commercial sources such as Taconic (Germantown, N.Y.). Many strains are suitable, but FVB female mice are preferred because of their higher susceptibility to tumor formation. FVB males were used for mating and vasectomized CD. 1 studs were used to stimulate pseudopregnancy. Vasectomized mice can be obtained from any commercial supplier. Founders were bred with either FVB mice or with 129/BL6×FVB p53 heterozygous mice. The mice with heterozygosity at p53 allele were used to potentially increase tumor formation. However, this has proven unecessary. Therefore, some F1 are of mixed strain. Founder tumors are FVB only. Six founders were obtained with some developing tumors without having litters.

EXAMPLE 3

HER2 Transgenic Mouse as a Tumor Model to Evaluate HER2-directed Therapies

Mammary gland biopsies of one founder transgenic mouse made as described in Example 2, showed 3+ expression of HER2, as determined by immunohistochemical staining, at about 2 months of age. The amount of HER2 extracellular domain (ECD) shed into serum was measured and found to be about 1.2 ng/ml (Huang et al., supra). This mouse subsequently developed a mammary tumor at 5 months of age, after bearing 4 litters. The tumor was surgically resected under aseptic conditions and minced into small pieces, 2 mm$^3$, which were then transplanted into the mammary fat pad of wild-type FVB female mice. As can be seen in FIG. 2A, the amount of HER2 ECD shed into serum increased over time following transplant and was found to be directly proportional to the weight of the tumor that developed (FIG. 2B). Tumors developed in 22 of 31 recipient mice, with a latency of 5 weeks. With subsequent passage, tumors developed with shorter latency and grew more rapidly, and tumor incidence increased to >95% of recipients. HER2 expression, as determined by immunohistochemical staining, was 3+ but heterogeneous in the primary tumor, but became uniformly 3+ after the first passage.

Figure 4:
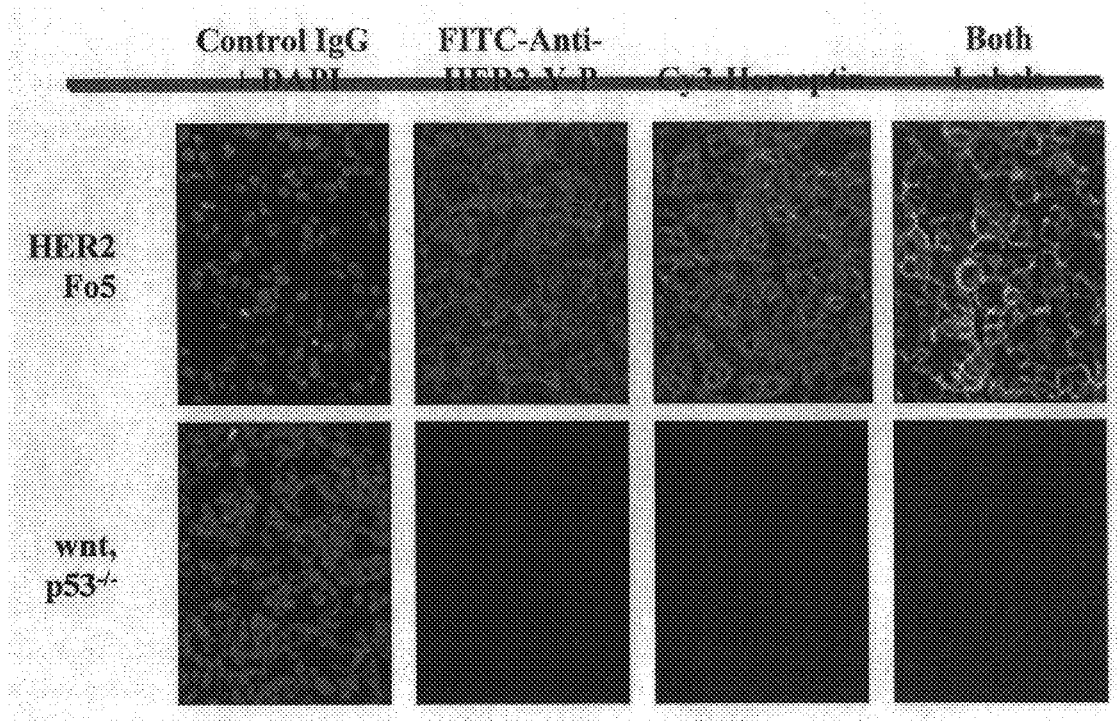
FIG. 4 Tumor cells originating from Founder 5 show binding to cy3-HERCEPTIN® and to anti-tyrosine phosphorylated HER2 antibody. Antibodies were injected intravenously into transgenic mice and the next day tumors were collected and sectioned. Antibody binding was visualized by fluoresence microscopy.

Treatment of tumor-bearing mice with HERCEPTIN® or 4D5, the murine antibody from which humanized HERCEPTIN® was derived, had only a modest effect on the growth of the transplanted tumors (FIG. 3). HER2 expression was 3+ in tumors that grew during HERCEPTIN® or 4D5 therapy, indicating that there was no selection of HER2-negative tumors. Moreover, as can be seen in FIG. 4, cy3-HERCEPTIN® was detected decorating tumor cells after injection into tumor-bearing mice, indicating that the lack of efficacy was not due to failure of the antibody to access the tumor. In addition, HER2 appears to be activated in the tumor cells, as evidenced by the binding of an anti-tyrosine-phosporylated-HER2 antibody (FIG. 4).

Figure 5:
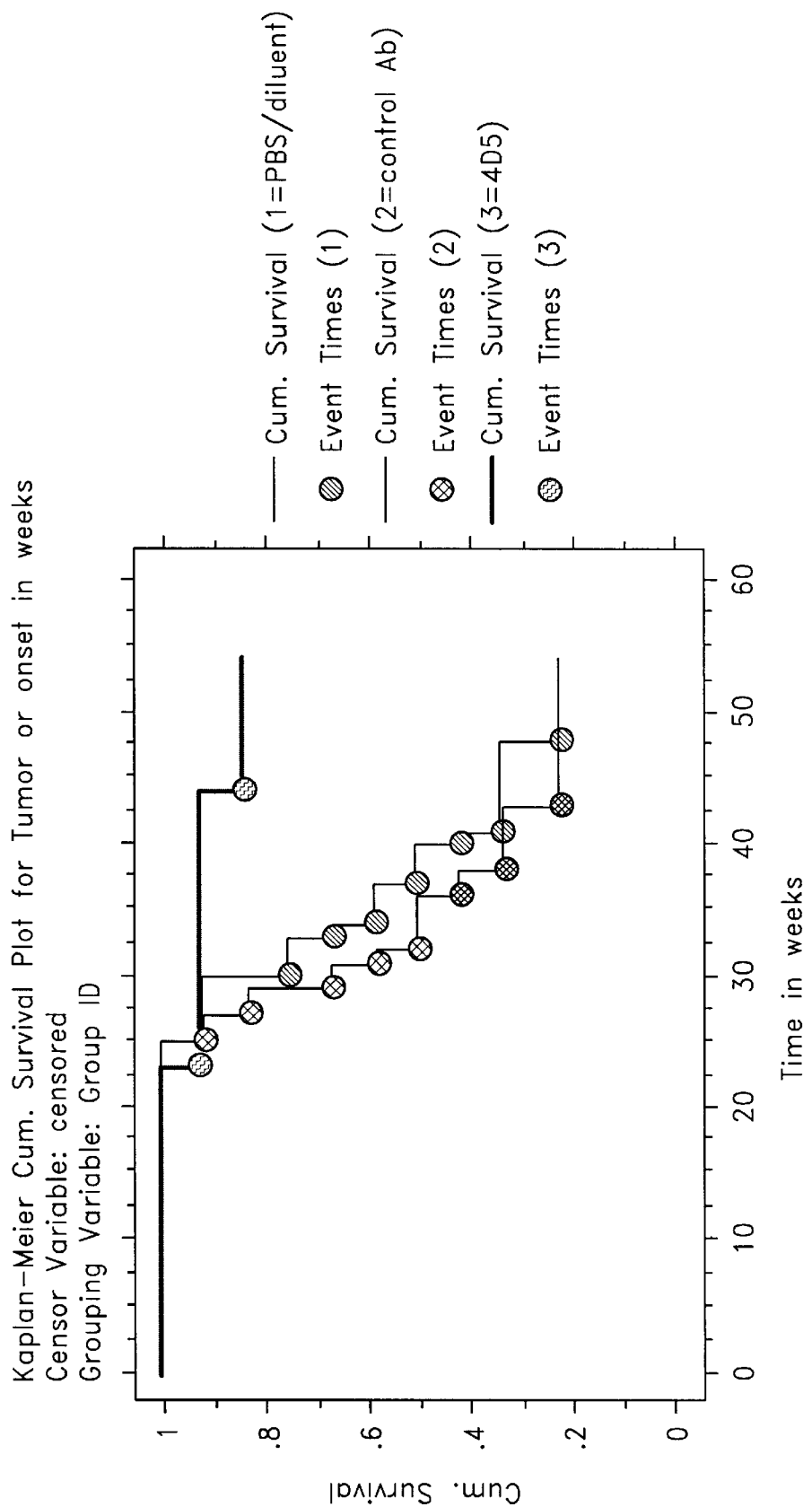
FIG. 5 Weekly administration of 4D5 can significantly reduce the formation of mammary tumors in HER2 transgenic carrier female mice.

In contrast to the lack of response to HERCEPTIN® treatment seen with transplanted tumors, FIG. 5 shows that the incidence of mammary tumor formation in transgenic carrier female mice was significantly reduced by weekly intraperitoneal administration of 100 mg/kg 4D5 anti-HER2 antibody. Injections began prior to tumor formation at 4 months of age (17 weeks), and tumors were checked twice a week by palpation. One control group received PBS or 4D5 diluent and a second control group received the control IgG antibody 1766 anti-gD.

Figure 6:
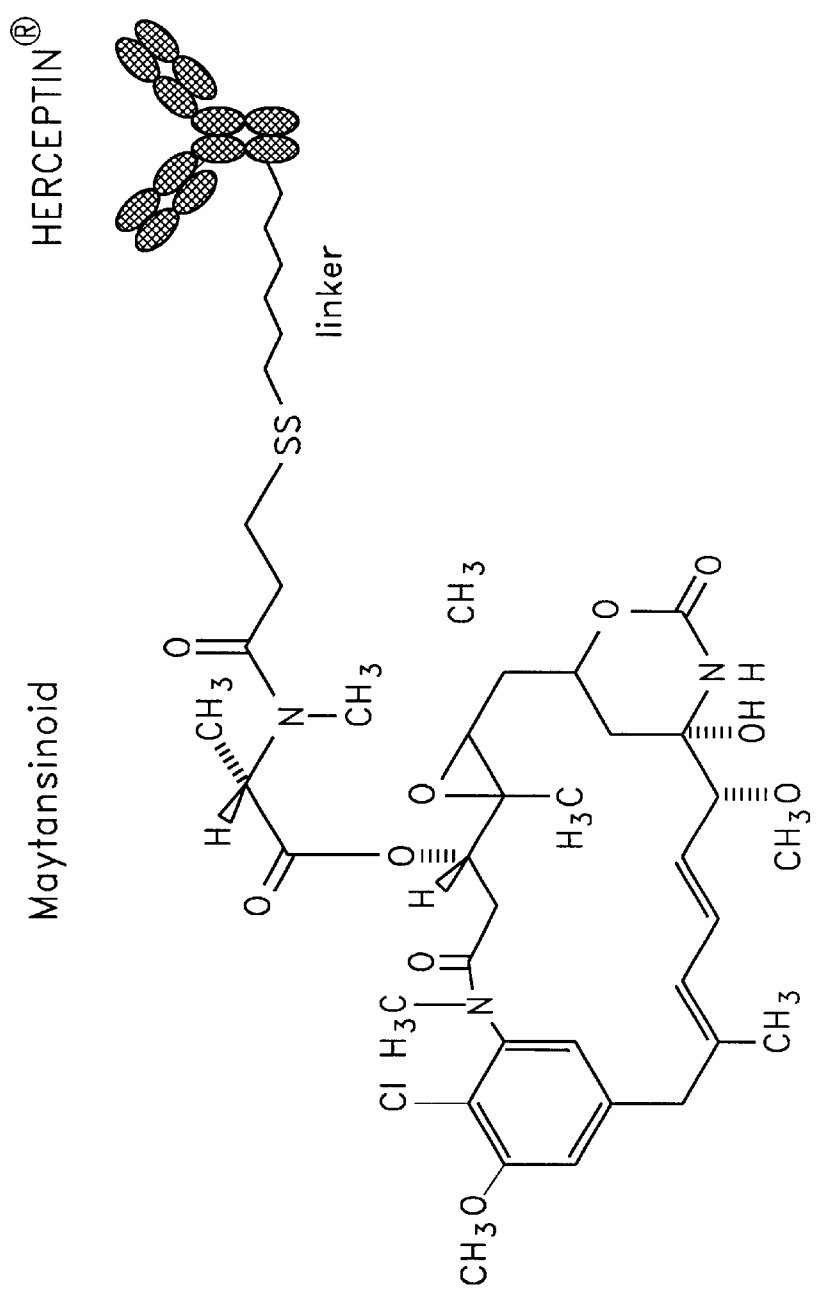
FIG. 6 Structure of a HERCEPTIN®-maytansinoid conjugate.
Figure 7:
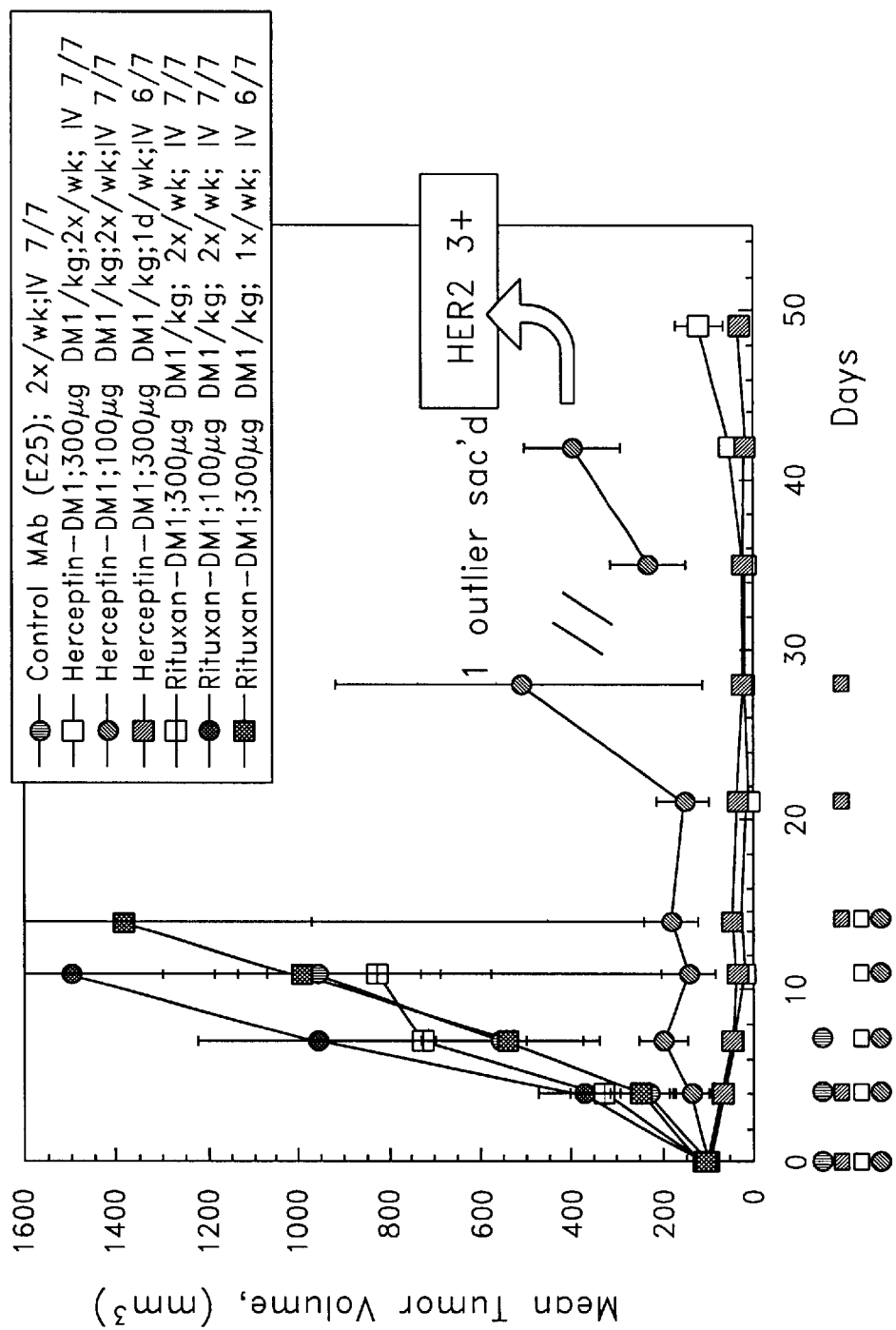
FIG. 7 Effect of different HERCEPTIN®-maytansinoid (Herceptin-DM1) dosing regimens on HER2-transgenic tumors. Mice with 100 mm$^3$ tumors were injected i.v. with HERCEPTIN®-DM1) or RITUXAN®-maytansinoid (RITUXAN®-DM1) at doses of 100 or 300 μg DM1/kg twice a week or 300 μg DM1/kg once a week. All animals received five doses.
Figure 8:
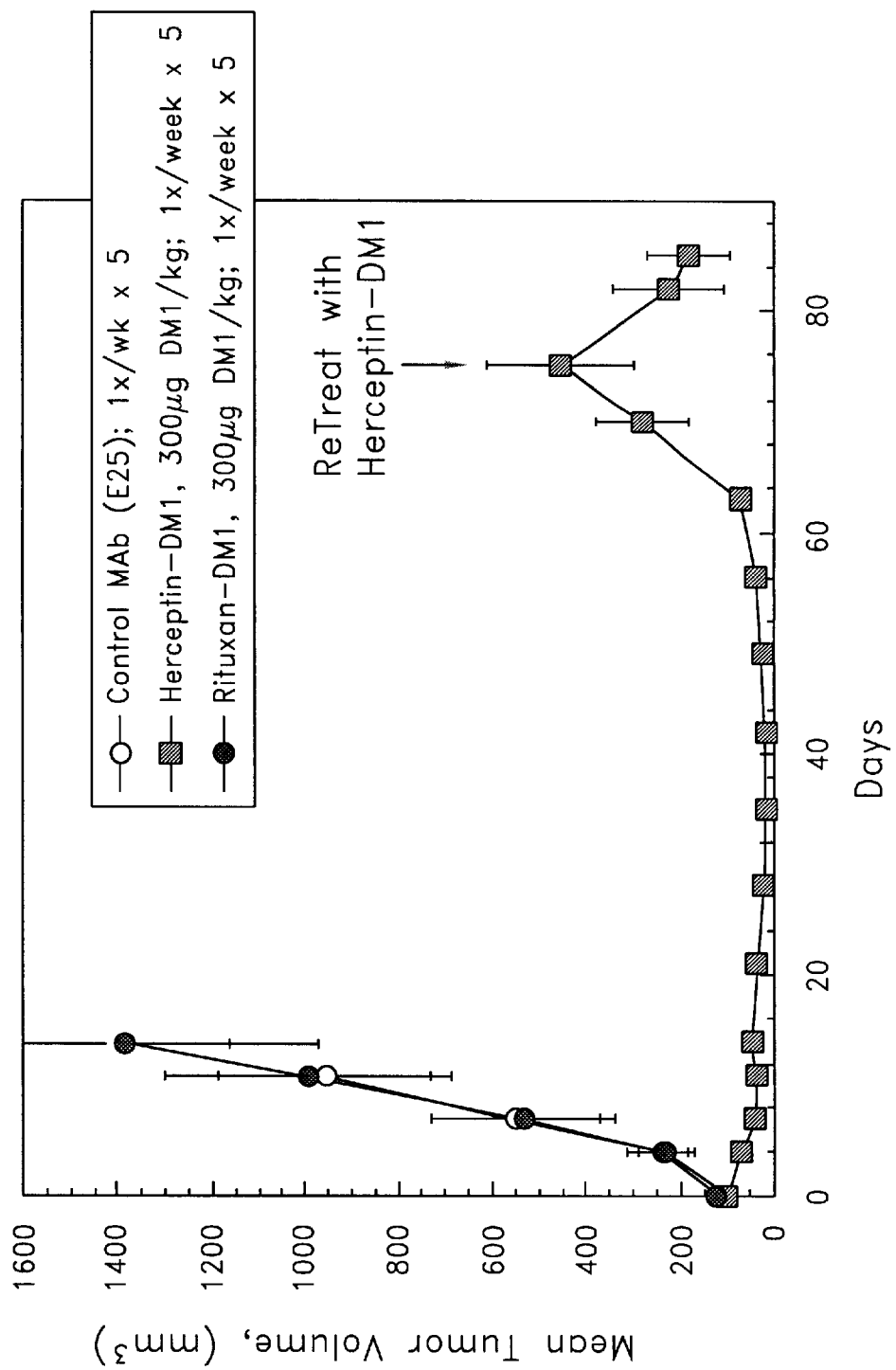
FIG. 8 Comparison of the most effective observed dose of HERCEPTIN®-DM1and RITUXAN®-DM1. Mice with 100 mm$^3$ tumors were treated with 300 μg DM1/kg of either HERCEPTIN®-DM1 or RITUXAN®-DM1 once a week for 5 weeks.

Based on the persistent expression of HER2 and the failure of existing tumors to respond to HERCEPTIN®, we tested a novel approach, using HERCEPTIN® conjugated to maytansinoid, the structure of which is depicted in FIG. 6. The toxin has a potent anti-tumor activity, but systemic safety issues limit its clinical use. However, it has shown dramatic activity when coupled to antibodies that direct the toxin to a specific target [Liu et al., Proc. Natl. Acad. Sci. USA 84: 7159–7163 (1996)], and antibody conjugates of maytansinoid are currently in clinical trials. FIGS. 3, 7 and 8 show that HERCEPTIN®-maytansinoid has dramatic anti-tumor activity in this model. RITUXAN®, an unrelated antibody, and a RITUXAN®-maytansinoid conjugate were used as negative controls.

As shown in FIG. 3, there was little response to HERCEPTIN® compared to the control antibody, RITUXAN®, but there was evident anti-tumor activity of the maytansinoid conjugate of HERCEPTIN®. All of the mice treated with HERCEPTIN®-maytansinoid showed striking shrinkage of their tumors, though none of the tumors disappeared. After approximately 4 weeks, tumors began to regrow. Five animals were sacrificed at this time. Their tumors were found to express HER2 at 3+ levels. Thus, there was no selection for HER2-negative tumors. Based on this observation, the remaining 3 mice were treated with HERCEPTIN®-maytansinoid for 5 consecutive days. The tumors again regressed in response to the treatment.

FIG. 7 shows the effects of three different dosing regimens of HERCEPTIN®-maytansinoid (HERCEPTIN®-DM1) on tumor size. Tumor size was reduced and tumor growth was suppressed for at least about 50 days by treatment with 5 doses of HERCEPTIN®DM1 at a concentration of 300 μg DM1/kg. This was true both when the HERCEPTIN®-DM1 was administered once a week and when it was administered twice a week. By contrast, administration of 5 doses of HERCEPTIN®-DM1 twice a week at a concentration of 100 μg DM1/kg did not shrink tumor size and suppressed tumor growth for somewhat less time. Matched RITUXAN®-maytansinoid (RITUXAN®-DM1) treatment showed little effect on tumor size at any of the tested doses or frequencies, indicating that the observed effect is specific to HERCEPTIN®-DM1. Similarly, unconjugated RITUXAN® (control MAb E25) showed no efficacy.

As can be seen in FIG. 8, a dose of HERCEPTIN®-DM1 (300 μg DM1/kg) once a week for five weeks caused tumors to shrink and prevented regrowth for more than 60 days. Retreatment with HERCEPTIN®-DM1 after tumor regrowth began shrank tumors a second time. Neither unconjugated RITUXAN® (control MAb E25) nor RITUXAN®-DM1 had any obvious effect on tumor growth.

EXAMPLE 4

Identification and Characterization of Cell Lines

A number of cell lines were prepared from tumors that arose spontaneously in several transgenic mice expressing human HER2. Cells were cultured from individual tumors that were identified in Founders 5, 32, 3080 and 3081–3, respectively. Briefly, tumors were excised and finely minced. The minced tumor was treated with collaginase and dispase for 30 minutes at 37° C. and then triturated with a 1 ml pipette tip. After allowing chunks to settle, the fine suspension was collected, diluted in growth media and spun. The growth media comprised DMEM and F12 (1:1), insulin, transferrin, vitamin E, progesterone, ethanolamine, hydrocortisone, T3, estradiol, heregulin, EGF and 2% FCS. After spinning the cells were resuspended in growth media and layered onto a 2-phase percoll gradient. The gradient was spun for 30 minutes at 2700 rpm at 4° C.

Cells were collected from the bottom interface, washed in media, resuspended in growth media and plated in fibronectin coated wells. The eleven cell lines that resulted were identified as HER-5, HER-32, HER-3081-3-1, HER-3081-3-4, HER-3081-3-10, HER-3081-3-19, HER-3081-3-33, HER-3081-3-12C, HER-3080-5L1, Lung met an Lacrimal gland.

Figure 9:
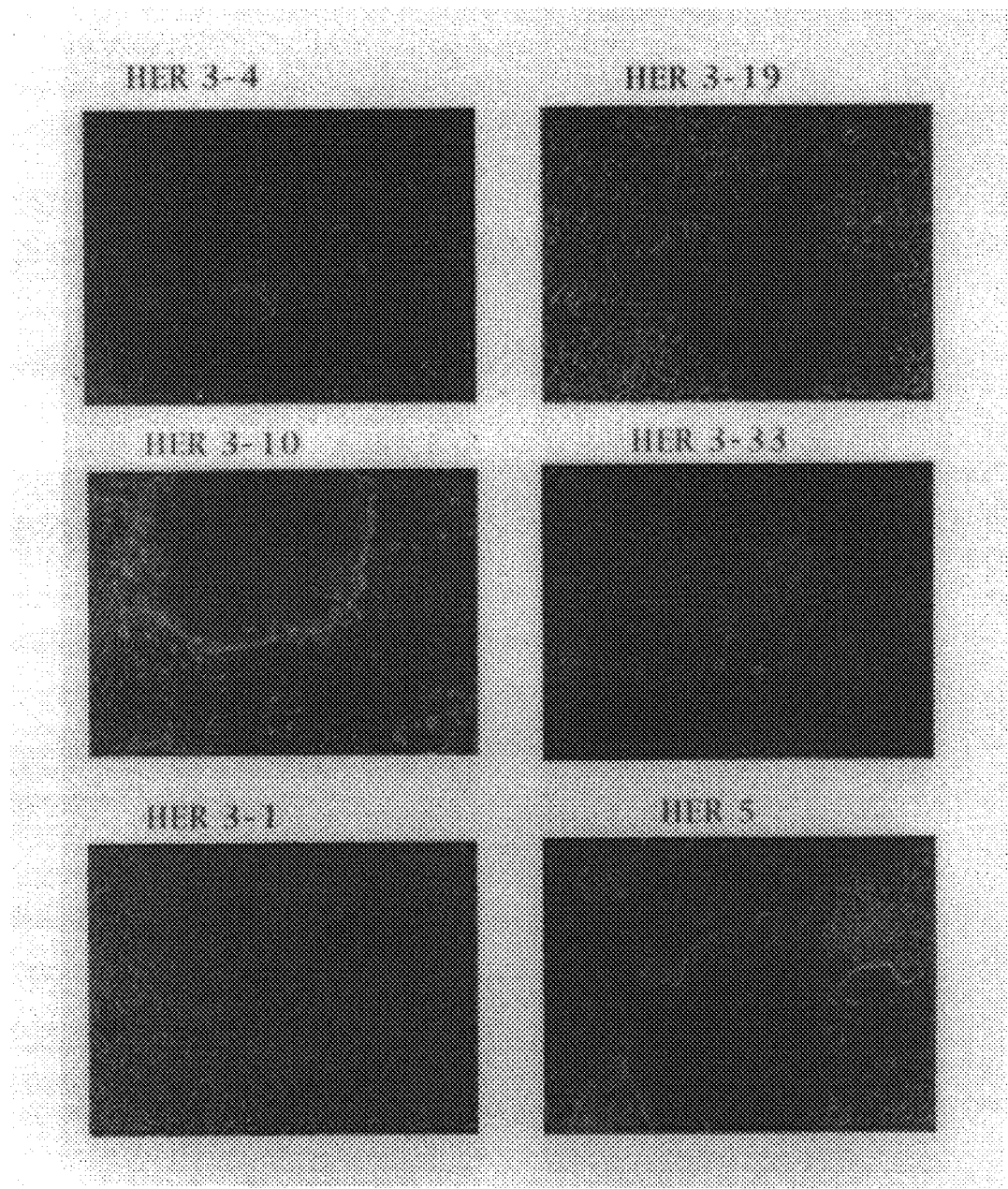
FIG. 9 depicts the morphology of several of the cell lines developed from HER2 transgenic mice.

The morphology of six of the cell lines was determined by microscopic analysis (FIG. 9). Interestingly, as can be seen in FIG. 9, the 5 cell lines that were derived from the same animal all have different morphologies.

Figure 10:
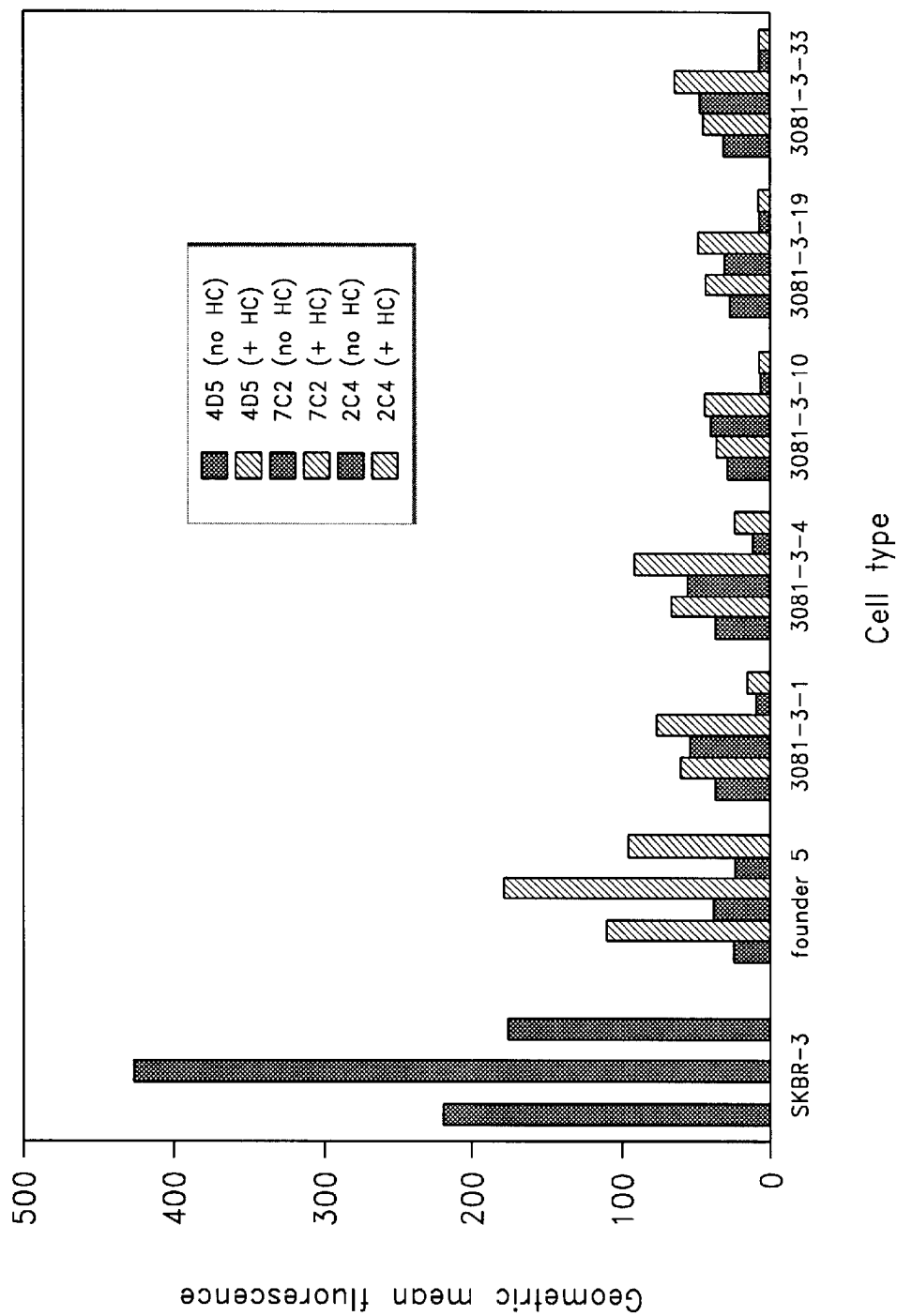
FIG. 10 shows expression of human HER2 on transgenic cell lines as determined by the binding of fluorescently labeled anti-HER2 antibodies 4D5, 2C4 and 7C2.

The expression of human HER2 on the transgenic cell lines was measured and compared to the expression levels seen in the human breast tumor cell line SK-BR3, which is known to express HER2 at high levels (FIG. 10). Expression levels were determined by the amount of binding of the fluorescently labeled anti-HER2 antibodies 4D5, 2C4 and 7C2. Binding was carried out essentially as described in Lewis et al. *Cancer Immunology and Immunotherapy* 37:255–263 (1993). In addition to measuring binding in normal growth media, binding was also assayed in media from which hydrocortisone had been withdrawn.

All of the HER2 transgenic cell lines that were tested demonstrated HER2 expression through their ability to bind at least two different anti-HER2 antibodies. However, all of the transgenic cell lines showed reduced expression in comparison to SK-BR3 cells. Interestingly, none of the cell lines derived from founder 3081-3 were able to bind the anti-HER2 antibody 2C4 to an appreciable extent. In addition, hydrocortisone withdrawal led to a significant deccrease in antibody binding in all of the transgenic cell lines (FIG. 10).

The responsiveness of several of the cell lines to the mitogens heregulin and EGF was measured. Briefly, cells were detached from a T75 flask with Dissociation Solution (Sigma) and plated in fibronectin coated 96 well plates. Approximately 10,000 cells were plated per well in 0.1 ml of fully supplemented media. After 24 hours the media was changed to heregulin and EGF free media, and each mitogen was added back at increasing doses as described below. After 4 days plates were washed twice with PBS (pH 7.5), stained with crystal violet (0.5% in methanol), dried, solubilized and the optical density measured at a wavelength of 540 nM on a plate reader, essentially as described in Sugarman et al. *Science* 230:943–945 (1985).

Figure 11:
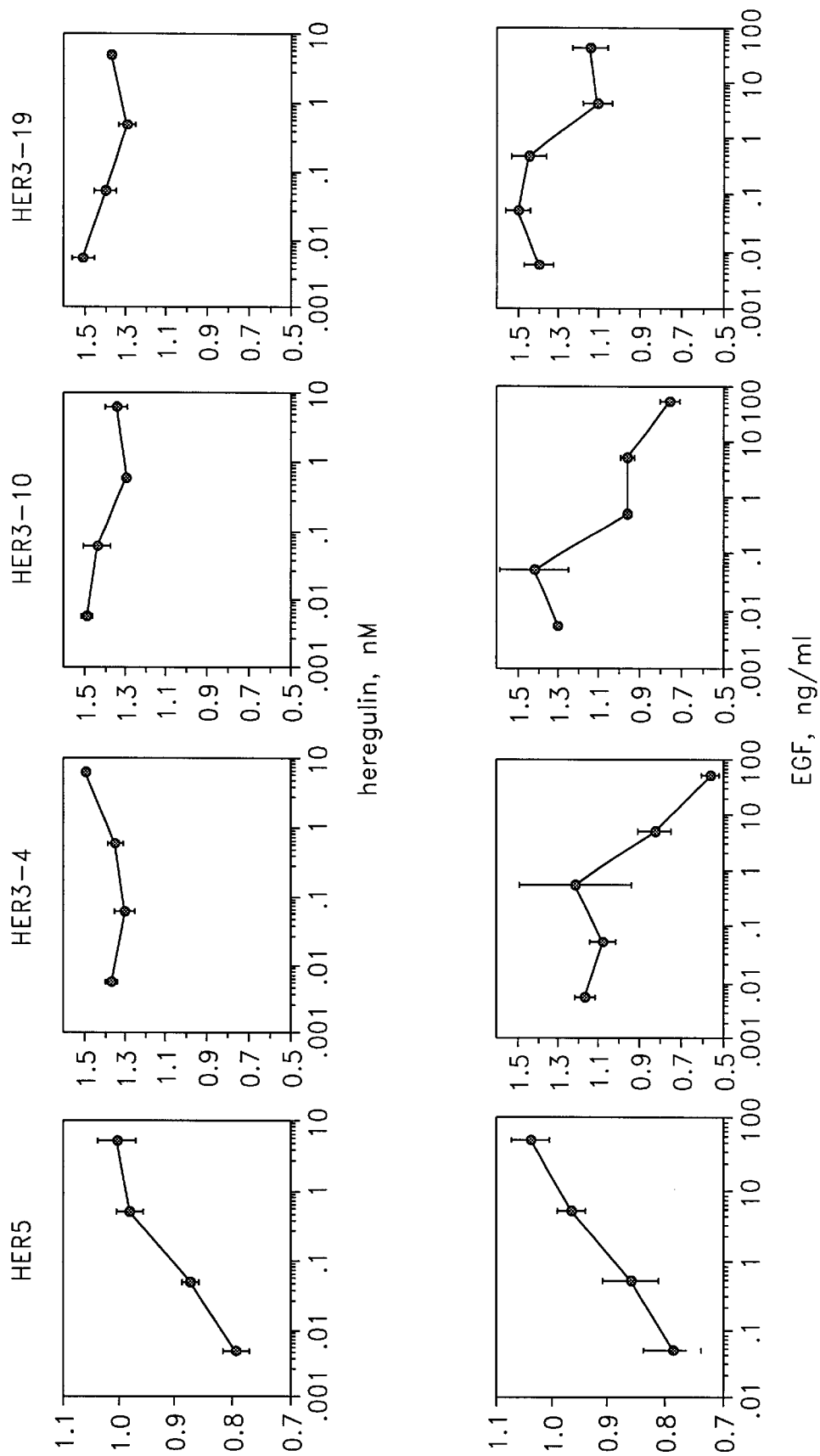
FIG. 11 shows that heregulin and EGF are mitogens only for cell line HER-5 and not for cell lines HER-3081-3-4, HER-3081-3-10 or HER-3081-3-19.

HER-5, HER-3081-3-4, HER-3081-3-10 and HER-3081-3-19 cells were grown in media containing heregulin at a concentration of 0.005, 0.05, 0.5 and 5 nM or EGF at a concentration of 0.05, 0.5, 5 and 50 ng/ml. As can be seen in FIG. 11, of the four cell lines tested, only the HER-5 cell line proliferated in response to treatment with heregulin or EGF.

The growth inhibitory characteristics of monoclonal antibodies 7C2, 4D5 and 2C4 were evaluated in the transgenic cell lines HER-5, HER-3081-3-4, HER-3081-3-10 and HER-3081-3-19. As described above, cells were detached from a T75 flask with Dissociation Solution (Sigma) and plated in fibronectin coated 96 well plates. Approximately 10,000 cells were plated per well in 0.1 ml of fully supplemented media. After 24 hours the media was changed to heregulin and EGF free media, and each mitogen was added back at a concentration of 5 nM and 50 ng/ml, respectively. In addition, the anti-HER2 antibodies 4D5, 2C4 and 7C2 were added at a concentration of 10 μg/ml. After 4 days, growth was assessed by staining with crystal violet (0.5% in methanol), essentially as described in Sugarman et al. *Science* 230:943–945 (1985). The data presented in FIG. 12 is a summary of the results of three experiments performed in triplicate. A "+" indicates some inhibition of growth while a "−" indicates no inhibition of growth.

All three monoclonal antibodies inhibited HER-5 cell growth in the presence or absence of both heregulin and EGF. HER-3081-3-4 cell growth was inhibited by 4D5 in all conditions and by 7C2 in the presence or absence of heregulin but not in the presence of EGF. Consistent with the failure of monoclonal antibody 2C4 to bind to cell lines derived from founder 3081 (see FIG. 10) this antibody failed to inhibit HER-3081-3-4 cell growth under any conditions. Growth of HER-3081-3-10 cells was inhibited by 7C2 under all conditions, by 4D5 in the presence and absence of EGF and by 2C4 in the presence of heregulin or EGF. By contrast, the growth of HER-3081-3-19 cells was only inhibited by 7C2 in the presence of heregulin (FIG. 12).

Figure 13:
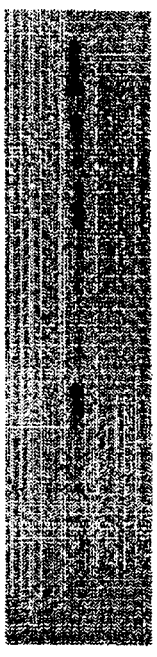
FIG. 13 shows the phosphorylation state of the human HER2 receptor in HER2 transgenic cell lines in both the presence and absence of mitogens.
Figure 13:

The phosphorylation state of the human HER2 receptor in each of the cell lines was determined when the cells were grown in the presence or absence of a mitogen (FIG. 13). Briefly, fully supplemented media was removed from three confluent flasks per cell line and replaced with serum, EGF and heregulin free media. EGF or heregulin were added back at a final concentration of 50 ng/ml and 50 nM respectively. Equivalent volumes of diluent alone were added as a control. After 25 minutes at 37° C. the media was removed and 1 ml lysis buffer containing 25 mM HEPES (pH 7.5), 150 mM NaCl, 1 mM EDTA, 1% Triton X-100, 1% CHAPS, 200 μM $Na_3PO_4$ and protease inhibitors was added. After 20 minutes the cells were scraped from the flask and centrifuged at 13,000 RPM at 4° C. for 10 minutes. The protein concentration of each lysate was determined with Coomassie Plus Protein Assay Reagent (Pierce). Lysates were diluted to I mg protein/ml and 10 μl of Ultralink Immobilized Protein AG beads (Pierce) were added along with 5 μg of immunoprecipitating antibody. After mixing overnight at 4° C. the beads were centrifuged at 13,000 RPM for 5 minutes and the supernatant was removed and washed three times with lysis buffer. 35 μl of Laemmli sample buffer with BME was added to the beads and boiled for 5 minutes. The beads were then centrifuged and 10μl of supernatent added per well in a 4–12% TRIS-glycine SDS-PAGE gel. The separated proteins were electroblotted to nitrocellulose, blocked with milk or BSA and incubated with antibodies. The proteins were visualized by chemoluminescence. Receptor that was phosphorylated was identified with an anti-phosphotyrosine antibody and total antibody was determined with an anti-HER2 antibody. As can be seen in FIG. 13, phosphorylation of the human HER2 receptor varies with each cell line and with the presence and absence of mitogens.

Figure 14:
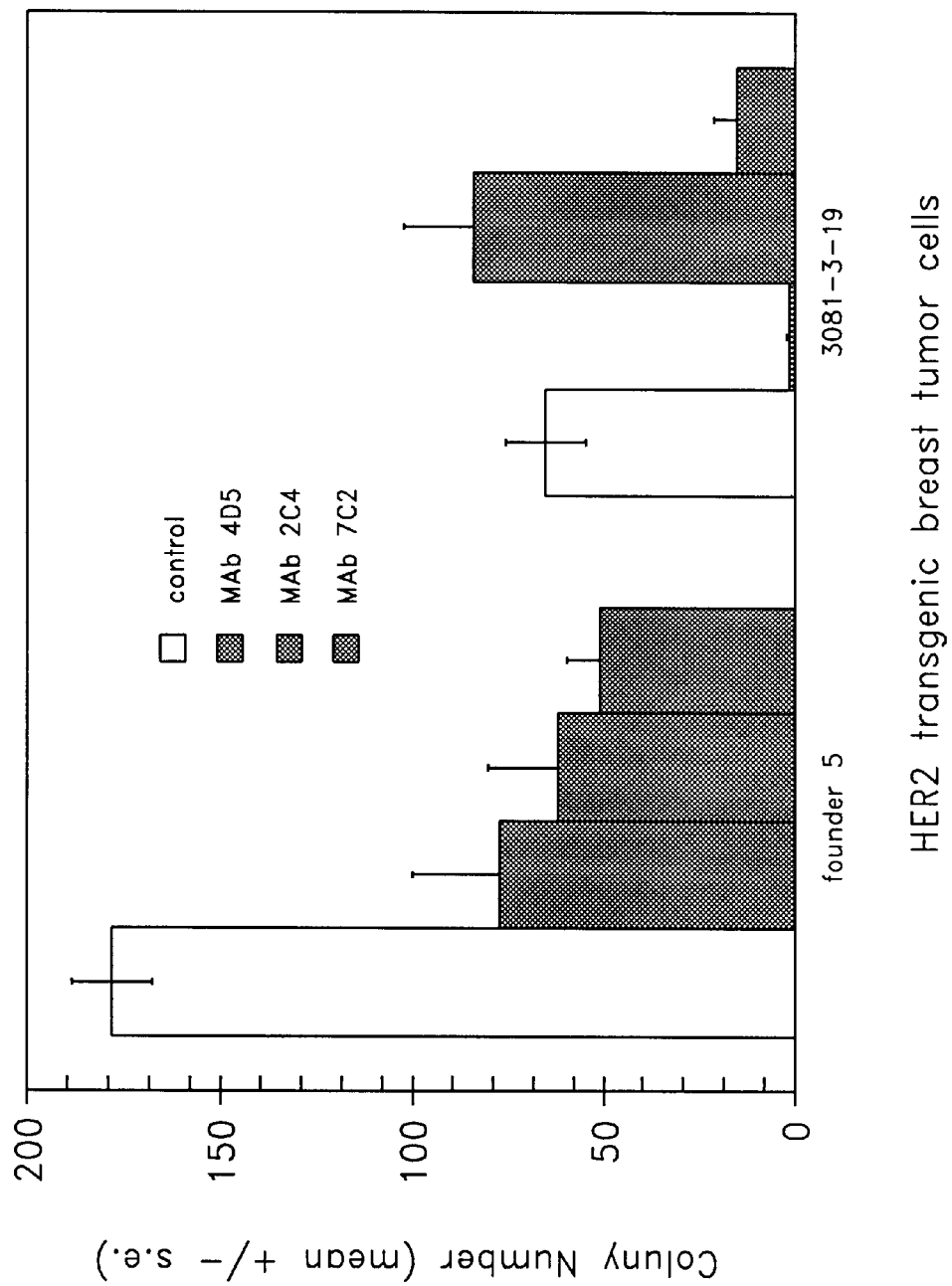
FIG. 14 shows the anchorage independent growth of HER2 transgenic cells after treatment with anti-HER2 antibodies.

The inhibition of anchorage independent growth of several of the transgenic cell lines by anti-HER2 monoclonal antibodies was tested. Cells were grown in soft agar in the presence and absence of the antibodies 4D5, 2C4 and 7C2. Anchorage independent growth was assessed essentially as described in Lewis et al. *Cancer Res.* 56:1457–1465. As can be seen in FIG. 14, the anchorage independent growth of the HER-5 cell line was significantly inhibited by all three monoclonal antibodies. The anchorage independent growth of the HER-3081-3-19 cell was reduced to near zero by the antibody 4D5 and was significantly reduced by the antibody 7C2. However, in contrast to the HER-5 line, HER-3081-3-19 anchorage independent growth was stimulated somewhat by the 2C4 monoclonal antibody (FIG. 14).

Figure 15A:
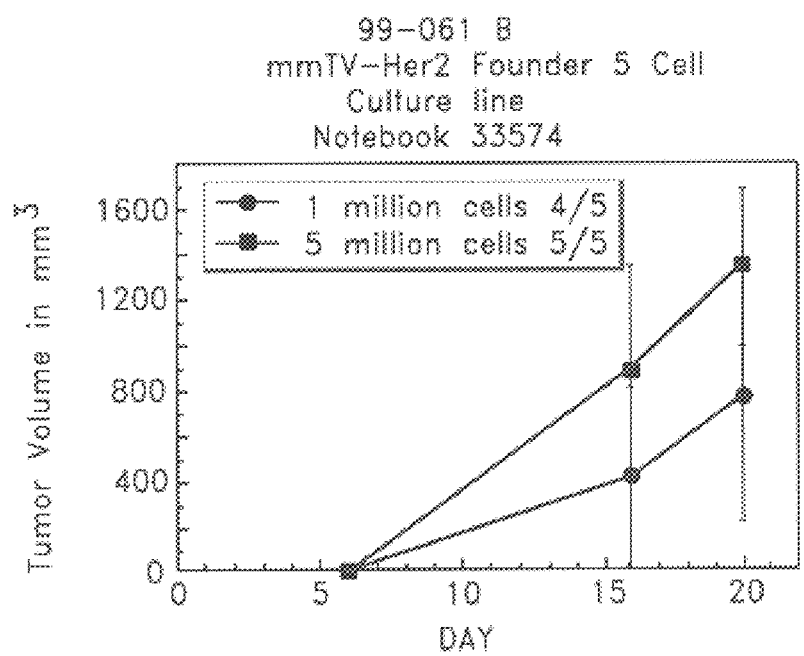
FIGS. 15A–B shows that a number of the transgenic HER2 cell lines, including one from Founder 5 (FIG. 15A) and several from Founder 3081-3 (FIG. 15B), are capable of forming tumors in immunocompetent mice.

The ability of cell lines to form tumors in immunocompetent animals was also assessed. Cells from the HER-5 cell line were implanted into the mammary fat pad of wild-type FVB female mice at day 0. Tumors were measured at regular intervals and the animals were sacrificed when the tumors became large or at the end of the study period. Five mice from each cell line were studied. As can be seen in FIG. 15A, implantation of 1 million or 5 million HER-5 cells produced tumors of significant volume by 15 days that continued to increase through day 20. The tumors formed from a starting population of 5 million cells were proportionately larger than the tumors formed from implantation of 1 million cells.

Figure 15B:
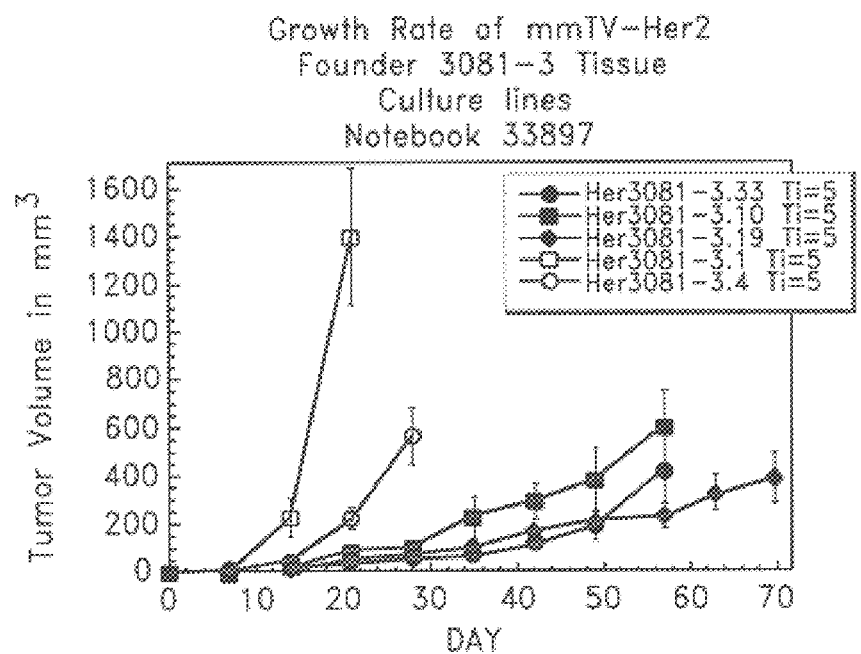

The ability of HER-3081-3 cell lines to form tumors was also investigated (FIG. 15B). In each case, 5 million cells were implanted in the mammary fat pad of wild-type FVB female mice on day 0. The HER-3081-3-1 cell line produced a rapidly growing tumor, which reached a volume of nearly 1400 mm³ by 20 days. The next fastest growing tumor was produced by the HER-3081-3-4 cell line, which produced a tumor of nearly 500 mm³ by 20 days. The other three cell lines all formed tumors at a slower rate.

Figure 16:
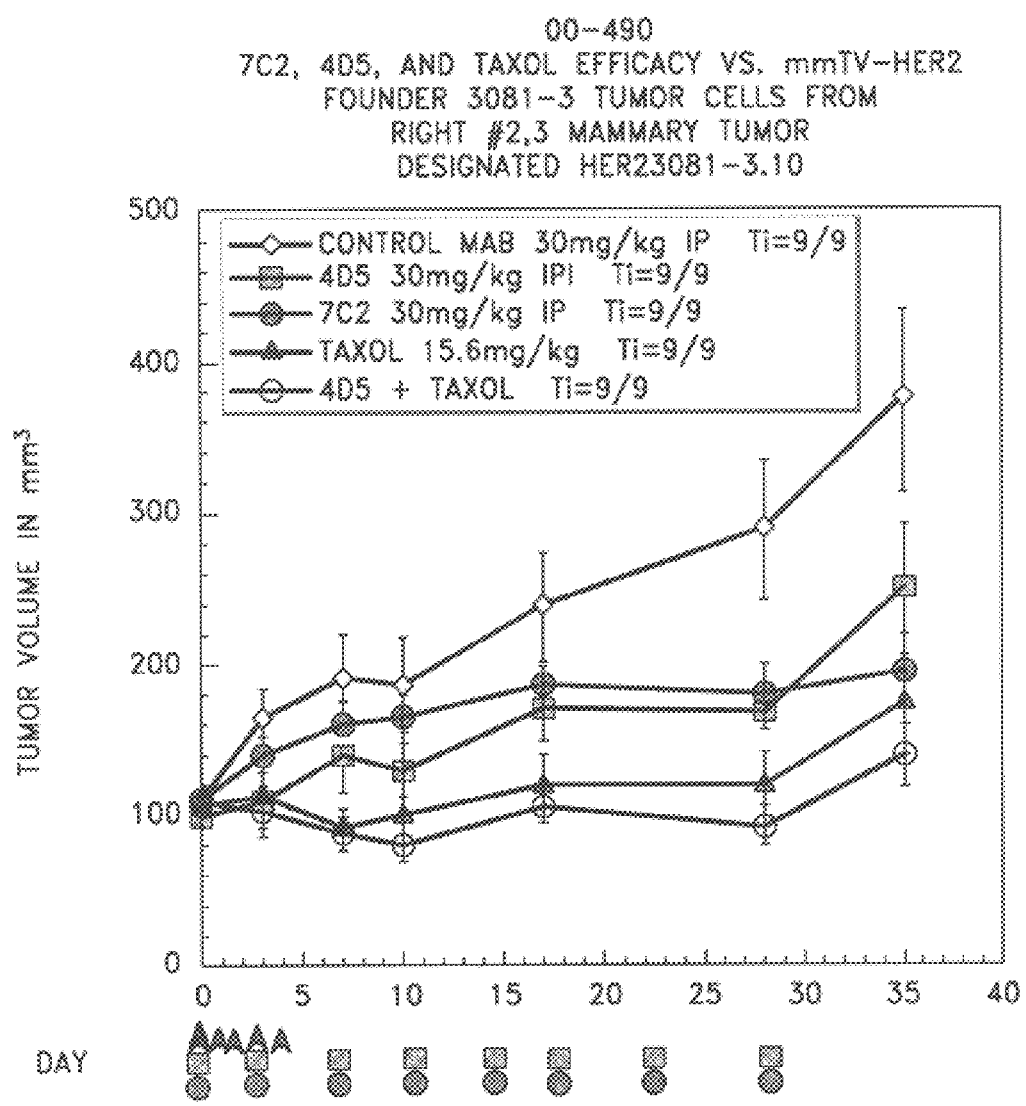
FIG. 16 shows the effect of taxol and anti-HER2 monoclonal antibodies 4D5 and 7C2 on the growth of tumors from the HER2 transgenic cell line HER-3081-3-10.

The efficacy of taxol and anti-HER2 monclonal antibodies 7C2 and 4D5 in preventing tumor growth was assessed (FIG. 16). At day 0, 6–8 week old FVP mice were inoculated under the skin with 2 million tumor cells from cell line HER-3081-3-10. When the tumors reached 100 mm³ the mice were separated into 5 groups with 9 animals per group. Antibodies 4D5 and 7C2 were given intraperitoneally at 30 mg/kg for 4 weeks. Taxol was given subcutaneously daily for 5 days at 15.6 mg/kg. Tumors were measured during the study at regular intervals. While each treatment reduced tumor growth in comparison to a control antibody, taxol was more effective than either of the antibodies alone. However, the combination of taxol and and the 4D5 MAb was the most effective at reducing tumor growth.

Deposit of Biological Material

The following cell lines have been deposited with the American Type Culture Collection, 10801 University Boulevard, Manassas, Va. 20110-2209, USA (ATCC) on Feb. 28, 2001:

| Cell Line Designation | ATCC No. |
|---|---|
| HER-5 | PTA-3135 |
| HER-3081-3-1 | PTA-3133 |
| HER-3081-3-10 | PTA-3134 |

This deposit was made under the provisions of the Budapest Treaty on the International Recognition of the Deposit of Microorganisms for the Purpose of Patent Procedure and the Regulations thereunder (Budapest Treaty). This assures maintenance of viable cultures for 30 years from the date of the deposit. The organisms will be made available by ATCC under the terms of the Budapest Treaty, and subject to an agreement between Genentech, Inc. and ATCC, which assures permanent and unrestricted availability of the progeny of the cultures to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.12 with particular reference to 886 OG 638).

In respect of those designations in which a European patent is sought, a sample of the deposited microorganism will be made available until the publication of the mention of the grant of the European patent or until the date on which the application has been refused or withdrawn or is deemed to be withdrawn, only by the issue of such a sample to an expert nominated by the person requesting the sample. (Rule 28 (4) EPC)

The assignee of the present application has agreed that if the cultures on deposit should die or be lost or destroyed when cultivated under suitable conditions, they will be promptly replaced on notification with a viable specimen of the same culture. Availability of the deposited strain is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the constructs deposited, since the deposited embodiments are intended to illustrate only certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that they represent. Indeed, various modifications of the invention in addition to those shown and described herein will become apparent to those skilled in the art from the foregoing description and fall within the scope of the appended claims.

All references cited throught the specification, and the references cited therein, are hereby expressly incorporated by reference.

What is claimed is:

1. A transgenic mouse that produces in its mammary gland cells detectable levels of a native human HER2 protein, wherein said transgenic mouse has stably integrated into its genome a nucleic acid sequence encoding a native human HER2 protein, operably linked to transcriptional regulatory sequences directing its expression to the mammary gland, and develops a mammary tumor that, when transplanted into a suitable rodent recipient, develops into a tumor that does not respond or responds poorly to anti-HER2 antibody treatment.

2. The transgenic mouse of claim 1 wherein said transcriptional regulatory sequences comprise a mammary gland specific promoter.

3. The transgenic mouse of claim 2 wherein said promoter is the MMTV-LTR promoter.

4. The transgenic mouse of claim 1 which expresses human HER2 protein in at least about 500,000 copies per cell.

5. The transgenic mouse of claim 1 which expresses human HER2 protein in at least about 2,000,000 copies per cell.

6. The transgenic mouse of claim 1 wherein said anti-HER2 antibody is a humanized version of the murine anti-HER2 antibody 4D5.

7. The transgenic mouse of claims 6 wherein said anti-HER2 antibody is huMAb4D5.

8. A rodent model for HER2 expressing tumors comprising a rodent bearing a tumor that developed from a transplanted mouse tumor, wherein said tumor overexpresses HER2 and does not respond or responds poorly to anti-HER2 antibody treatment.

9. The rodent model of clam 8 wherein said tumor expresses a human HER2 protein in at least about 500,000 copies per cell.

10. The rodent model of claim 8 wherein said tumor expresses a human HER2 protein in at least about 2,000,000 copies per cell.

11. The rodent model of claim 8 wherein said tumor has been transplanted from a transgenic mouse which has stably integrated into its genome a nucleic acid sequence encoding a native human HER2 protein, operably linked to transcriptional regulatory sequences directing its expression to the mammary gland.

12. The rodent model of claim 11 wherein said transgenic mouse bears a tumor expressing a human HER2 protein in at least about 500,000 copies per cell.

13. The rodent model of claim 11 wherein said transgenic mouse bears a tumor expressing a human HER2 protein in at least about 2,000,000 copies per cell.

14. A rodent model for HER2 expressing tumors comprising a rodent bearing a tumor overexpressing HER2 wherein said tumor does not respond or responds poorly to treatment with anti-HER2 antibody 4D5 or a conjugate of said antibody.

15. Thee rodent model of claim 14 wherein said tumor expresses a human HER2 protein in at least about 500,000 copies per cell.

16. The rodent model of claim 14 wherein said tumor expresses a human HER2 protein in at least about 2,000,000 copies per cell.

17. A transgene construct comprising a nucleic acid encoding a native human HER2 protein, wherein said nucleic acid is operably linked to transcriptional regulatory sequences directing its expression to the mammary gland.

18. The transgene construct of claim 17 comprising a mammary gland specific promoter.

19. The transgene construct of claim 18 wherein said mammary gland specific promoter is an MMTV-LTR promoter.

20. A stable cell line that expresses HER2 and is established from a HER2 transgenic mouse that has stably integrated into its genome a nucleic acid sequence encoding a native human HER2 protein, wherein said nucleic acid is operably linked to transcriptional regulatory sequences directing its expression to the mammary gland.

21. The stable cell line of claim 20 wherein said stable cell line is a breast cancer cell line.

22. The cell line HER-5, deposited with ATCC on Feb. 28, 2001 (Accession Number PTA-3135).

23. The cell line HER-3081-3-1, deposited with ATCC on Feb. 28, 2001 (Accession Number PTA-3133).

24. The cell line HER-3081-3-10, deposited with ATCC on Feb. 28, 2001 (Accession Number PTA-3134).

25. A method of screening drug candidates for the treatment of a disease or disorder characterized by the overexpression of HER2 comprising (a) administering a drug candidate to a transgenic mouse that overexpresses in its mammary gland cells a native human HER2 protein, wherein said transgenic mouse has stably integrated into its genome a nucleic acid sequence encoding a native human HER2 protein, operably linked to transcriptional regulatory sequences directing its expression to the mammary gland, and develops a mammary tumor, or to a rodent bearing a tumor transplanted from said transgenic mouse, wherein said transplanted tumor does not respond or poorly responds to anti-HER2 antibody treatment; (b) evaluating Me effect of said drug candidate on said tumor.

26. The method of claim wherein said disease or disorder is a HER2-overexpressing cancer.

27. The method of claim 26 wherein said HER2-overexpressing cancer is selected from the group consisting of breast, ovarian, stomach, endometrial, salivary gland, lung, kidney, colon, thyroid, pancreatic and bladder cancer.

28. The method of claim 27 wherein said cancer is breast cancer.

29. The method of claim 28 wherein said breast cancer expresses HER2 in at least about 500,000 copies per cell.

30. The method of claim 28 wherein said breast cancer expresses HER2 in at least about 2,000,000 copies per cell.

31. The method of claim 25 wherein said drug candidate is evaluated for its ability to induce cell death.

32. The method of claim 25 wherein said drug candidate is evaluated for its ability to induce apoptosis.

33. The method of claim 25 wherein said drug candidate is an antibody.

34. The method of claim 25 wherein said drug candidate i an antibody conjugate.

35. The method of claim 25 wherein said drug candidate is a small molecule.

36. The method of claim 25 further comprising the step of identifying a candidate that has the ability to induce death apoptosis of cancer cells.

37. The method of claim 25 further comprising the step of administering said candidate identified to a human patient.

* * * * *

UNITED STATES PATENT AND TRADEMARK OFFICE
CERTIFICATE OF CORRECTION

PATENT NO. : 6,632,979 B2  
DATED : October 14, 2003  
INVENTOR(S) : Erickson et al.

It is certified that error appears in the above-identified patent and that said Letters Patent is hereby corrected as shown below:

Column 63,  
Line 18, should be changed from "Thee rodent model of claim 14 wherein said tumor expresses a human HER2 protein in at least about 500,000 copies per cell." to  
-- The rodent model of claim 14 wherein said tumor expresses a human HER2 protein in at least about 500,000 copies per cell --.  
Line 34, change "lished from a HER2 transgenic mouse that has stably" to  
-- lished from a HER2-transgenic mouse that has stably. --.

Column 64,  
Line 15, change "to anti-HER2 antibody treatment; (b) evaluating Me effect of" to  
-- to anti-HER2 antibody treatment; (b) evaluating the effect of --.  
Line 17, should be changed from "The method of claim wherein said disease or disorder is a HER2-overexpressing cancer." to -- The method of claim 25 wherein said disease or disorder is a HER2-overexpressing cancer. --.  
Line 34, should be changed from "The method of claim 25 wherein said drug candidate i an antibody conjugate." to -- The method of claim 25 wherein said drug candidate is an antibody conjugate. --.  
Line 38, should be changed from "The method of claim 25 further comprising the step of identifying a candidate that has the ability to induce death apoptosis of cancer cells." to -- The method of claim 25 further comprising the step of identifying a candidate that has the ability to induce death or apoptosis of cancer cells. --.  
Line 41, should be changed from "The method of claim 25 further comprising the step of administering said candidate identified to a human patient." to -- The method of claim 36 further comprising the step of administering said candidate identified to a human patient. --.

Signed and Sealed this

Thirteenth Day of April, 2004

JON W. DUDAS  
*Acting Director of the United States Patent and Trademark Office*

SEQUENCE LISTING

```
<160> NUMBER OF SEQ ID NOS: 4

<210> SEQ ID NO 1
<211> LENGTH: 9274
<212> TYPE: DNA
<213> ORGANISM: Artificial Sequence
<220> FEATURE:
<223> OTHER INFORMATION: Vector Sequence

<400> SEQUENCE: 1
aagctcgatc ggtgcacatt aattcatgat cgcgagctag cagcttgcat gcctgcagca      60
gaaatggttg aactcccgag agtgtcctac acctagggga gaagcagcca aggggttgtt     120
tcccaccaag gacgacccgt ctgcgcacaa acggatgagc ccatcagaca aagacatatt     180
```

-continued

| | |
|---|---|
| cattctctgc tgcaaacttg gcatagctct gctttgctgg ggcattgggg gaagttgcgg | 240 |
| ttcgtgctcg cagggctctc acccttgact cttttaatag ctcttctgtg caagattaca | 300 |
| atctaaacaa ttcggagaac tcgaccttcc tctcctgagg caaggaccac agccaacttc | 360 |
| ctcttacaag ccgcatcgat tttgtccttc agaaatagaa ataagaatgc ttgctaaaaa | 420 |
| ttatatttt accaataaga ccaatccaat aggtagatta ttagttacta tgttaagaaa | 480 |
| tgaatcatta tcttttagta ctattttac tcaaattcag aagttagaaa tgggaataga | 540 |
| aaatagaaag agacgctcaa cctcaattga agaacaggtg caaggactat tgaccacagg | 600 |
| cctagaagta aaaagggaa aaagagtgt ttttgtcaaa ataggagaca ggtggtggca | 660 |
| accagggact tatagggac cttacatcta cagaccaaca gatgccccct taccatatac | 720 |
| aggaagatat gacttaaatt gggataggtg ggttacagtc aatggctata aagtgttata | 780 |
| tagatccctc cctttcgtg aaagactcgc cagagctaga cctccttggt gtatgttgtc | 840 |
| tcaagaagaa aaagacgaca tgaaacaaca ggtacatgat tatatttatc taggaacagg | 900 |
| aatgcacttt tggggaaaga ttttccatac caaggagggg acagtggctg gactaataga | 960 |
| acattattct gcaaaaactt atggcatgag ttattatgaa tagcctttat tggcccaacc | 1020 |
| ttgcggttcc caaggcttaa gtaagttttt ggttacaaac tgttcttaaa acgaggatgt | 1080 |
| gagacaagtg gtttcctgac ttggtttggt atcaaaggtt ctgatctgag ctctgagtgt | 1140 |
| tctattttcc tatgttcttt tggaatttat ccaaatctta tgtaaatgct tatgtaaacc | 1200 |
| aagatataaa agagtgctga ttttttgagt aaacttgcaa cagtcctaac attcacctct | 1260 |
| tgtgtgtttg tgtctgttcg ccatcccgtc tccgctcgtc acttatcctt cactttccag | 1320 |
| agggtccccc cgcagacccc ggatcgctag ctcgcgaatc gataagcttg cggccgctta | 1380 |
| actgcagaag ttggtcgtga ggcactgggc aggtaagtat caaggttaca agacaggttt | 1440 |
| aaggagacca atagaaactg ggcttgtcga gacagagaag actcttgcgt ttctgatagg | 1500 |
| cacctattgg tcttactgac atccactttg cctttctctc cacaggtgtc cactcccagg | 1560 |
| ttcaattaca gctcttaagc ggccgcaagc ttgatatcga attcctgcag cccgggggat | 1620 |
| ccactagtgg atccaaagaa ttcaaaaagc ttctcgaggg cgcgcgcccg ccccccaccc | 1680 |
| ctcgcagcac cccgcgcccc cgccctccc agccgggtcc agccggagcc atggagctgg | 1740 |
| cggccttgtg ccgctggggg ctcctcctcg ccctcttgcc cccggagcc gcgagcaccc | 1800 |
| aagtgtgcac cggcacagac atgaagctgc ggctccctgc cagtcccgag acccacctgg | 1860 |
| acatgctccg ccacctctac cagggctgcc aggtggtgca gggaaacctg gaactcacct | 1920 |
| acctgcccac caatgccagc ctgtccttcc tgcaggatat ccaggaggtg caggctacg | 1980 |
| tgctcatcgc tcacaaccaa gtgaggcagg tcccactgca gaggctgcgg attgtgcgag | 2040 |
| gcacccagct ctttgaggac aactatgccc tggccgtgct agacaatgga gacccgctga | 2100 |
| acaataccac ccctgtcaca ggggcctccc caggaggcct gcgggagctg cagcttcgaa | 2160 |
| gcctcacaga gatcttgaaa ggaggggtct tgatccagcg gaaccccag ctctgctacc | 2220 |
| aggacacgat tttgtggaag acatcttcc acaagaacaa ccagctggct ctcacactga | 2280 |
| tagacaccaa ccgctctcgg gcctgccacc cctgttctcc gatgtgtaag ggctcccgct | 2340 |
| gctggggaga gagttctgag gattgtcaga gcctgacgcg cactgtctgt gccggtggct | 2400 |
| gtgcccgctg caagggccca ctgcccactg actgctgcca tgagcagtgt gctgccggct | 2460 |
| gcacgggccc caagcactct gactgcctgg cctgcctcca cttcaaccac agtggcatct | 2520 |
| gtgagctgca ctgcccagcc ctggtcacct acaacacaga cacgtttgag tccatgccca | 2580 |

-continued

```
atcccgaggg ccggtataca ttcggcgcca gctgtgtgac tgcctgtccc tacaactacc    2640
tttctacgga cgtgggatcc tgcaccctcg tctgccccct gcacaaccaa gaggtgacag    2700
cagaggatgg aacacagcgg tgtgagaagt gcagcaagcc ctgtgcccga gtgtgctatg    2760
gtctgggcat ggagcacttg cgagaggtga gggcagttac cagtgccaat atccaggagt    2820 tgctggctg caagaagatc tttgggagcc tggcatttct gccggagagc tttgatgggg     2880
acccagcctc caacactgcc ccgctccagc cagagcagct ccaagtgttt gagactctgg    2940
aagagatcac aggttaccta tacatctcag catggccgga cagcctgcct gacctcagcg    3000
tcttccagaa cctgcaagta atccggggac gaattctgca caatggcgcc tactcgctga    3060
ccctgcaagg gctgggcatc agctggctgg ggctgcgctc actgagggaa ctgggcagtg    3120
gactggccct catccaccat aacacccacc tctgcttcgt gcacacggtg ccctgggacc    3180
agctctttcg gaacccgcac caagctctgc tccacactgc caaccggcca gaggacgagt    3240
gtgtgggcga gggcctggcc tgccaccagc tgtgcgcccg agggcactgc tggggtccag    3300
ggcccaccca gtgtgtcaac tgcagccagt tccttcgggg ccaggagtgc gtggaggaat    3360
gccgagtact gcagggctc cccagggagt atgtgaatgc caggcactgt ttgccgtgcc     3420
accctgagtg tcagccccag aatggctcag tgacctgttt tggaccggag ctgaccagt     3480 gtgtggcctg tgcccactat aaggaccctc ccttctgcgt ggcccgctgc cccagcggtg    3540
tgaaacctga cctctcctac atgcccatct ggaagtttcc agatgaggag ggcgcatgcc    3600
agccttgccc catcaactgc acccactcct gtgtggacct ggatgacaag ggctgccccg    3660
ccgagcagag agccagccct ctgacgtcca tcgtctctgc ggtggttggc attctgctgg    3720
tcgtggtctt gggggtggtc tttgggatcc tcatcaagcg acggcagcag aagatccgga    3780
agtacacgat gcggagactg ctgcaggaaa cggagctggt ggagccgctg acacctagcg    3840
gagcgatgcc caaccaggcg cagatgcgga tcctgaaaga cggagctg aggaaggtga     3900 aggtgcttgg atctgcgct tttggcacag tctacaaggg catctggatc cctgatgggg     3960
agaatgtgaa aattccagtg gccatcaaag tgttgaggga aaacacatcc cccaaagcca    4020
acaaagaaat cttagacgaa gcatacgtga tggctggtgt gggctccca tatgtctccc     4080 gccttctggg catctgcctg acatccacgg tgcagctggt gacacagctt atgcctatg     4140 gctgcctctt agaccatgtc cgggaaaacc gcggacgcct gggctcccag gacctgctga    4200
actggtgtat gcagattgcc aagggatga gctacctgga ggatgtgcgg ctcgtacaca    4260
gggacttggc cgctcggaac gtgctggtca gagtcccaa ccatgtcaaa attacagact     4320
tcgggctggc tcgctgctg gacattgacg agacagagta ccatgcagat ggggcaagg     4380 tgccatcaa gtggatggcg ctggagtcca ttctccgccg gcggttcacc caccagagtg     4440
atgtgtggag ttatggtgtg actgtgtggg agctgatgac ttttgggggcc aaaccttacg    4500 atgggatccc agcccgggag atccctgacc tgctggaaaa gggggagcgg ctgccccagc    4560
cccccatctg caccattgat gtctacatga tcatggtcaa atgttggatg attgactctg    4620
aatgtcggcc aagattccgg gagttggtgt ctgaattctc ccgcatggcc agggacccc     4680 agcgctttgt ggtcatccag aatgaggact gggcccagc cagtcccttg acagcacct     4740 tctaccgctc actgctggag gacgatgaca tggggacct ggtggatgct gaggagtatc     4800
tggtacccca gcagggcttc ttctgtccag accctgcccc gggcgctggg ggcatggtcc    4860
accacaggca ccgcagctca tctaccagga gtggcggtgg ggacctgaca ctagggctgg    4920
```

-continued

```
agccctctga agaggaggcc cccaggtctc cactggcacc ctccgaaggg gctggctccg    4980
atgtatttga tggtgacctg ggaatggggg cagccaaggg gctgcaaagc ctccccacac    5040
atgaccccag ccctctacag cggtacagtg aggaccccac agtaccccctg ccctctgaga   5100
ctgatggcta cgttgcccccc ctgacctgca gcccccagcc tgaatatgtg aaccagccag   5160
atgttcggcc ccagccccct tcgccccgag agggccctct gcctgctgcc cgacctgctg    5220
gtgccactct ggaaagggcc aagactctct ccccagggaa gaatgggggtc gtcaaagacg   5280
tttttgcctt tgggggtgcc gtggagaacc ccgagtactt gacacccccag ggaggagctg   5340
ccccctcagcc ccaccctcct cctgccttca gcccagcctt cgacaacctc tattactggg   5400
accaggaccc accagagcgg ggggctccac ccagcacctt caaagggaca cctacggcag    5460
agaacccaga gtacctgggt ctggacgtgc cagtgtgaac cagaaggcca agtccgcaga    5520
agccctgatg tgtcctcagg gagcagggaa ggcggcctct gagctattcc agaagtagtg    5580
aggaggcttt tttggaggcc taggcttttg caaaaagctt atcgataccg tcgactcgag    5640
agtacttcta gagcggccgc gggcccatcg cctctgacag caacgtctat gacctcctaa    5700
aggacctaga ggaaggcatc caaacgctga tggggaggct ggaagatggc agcccccgga    5760
ctgggcagat cttcaagcag acctacagca agttcgacac aaactcacac aacgatgacg    5820
cactactcaa gaactacggg ctgctctact gcttcaggaa ggacatggac aaggtcgaga    5880
cattcctgcg catcgtgcag tgccgctctg tggaggcag ctgtggcttc tagctgcccg     5940
ggtggcatcc ctgtgacccc tccccagtgc ctctcctggc cctggaagtt gccactccag    6000
tgcccaccag ccttgtccta ataaaattaa gttgcatcat tttgtctgac taggtgtcct    6060
tctataatat tatgggtgg aggggggtgg tatggagcaa ggggcccaag ttgggaagac     6120
aacctgtagg gcctgcgggg tctattcggg aaccaagctg gagtgcagtg gcacaatctt    6180
ggctcactgc aatctccgcc tcctgggttc aagcgattct cctgcctcag cctcccgagt    6240
tgttgggatt ccaggcatgc atgaccaggc tcagctaatt tttgttttt tggtagagac     6300
ggggtttcac catattggcc aggctggtct ccaactccta atctcaggtg atctaccac     6360
cttggcctcc caaattgctg ggattacagg cgtgaaccac tgctcccttc cctgtccttc    6420
tgatttaaa ataactatac cagcaggagg acgtccagac acagcatagg ctacctgcca    6480
tggcccaacc ggtgggacat ttgagttgct tgcttggcac tgtcctctca tgcgttgggt    6540
ccactcagta gatgcctgtt gaattacgat cggtgcacat taattcatga aattcgtaat    6600
catggtcata gctgtttcct gtgtgaaatt gttatccgct cacaattcca cacaacatac    6660
gagccggaag cataaagtgt aaagcctggg gtgcctaatg agtgaggtaa ctcacattaa    6720
ttgcgttgcg ctcactgccc gctttccagt cgggaaacct gtcgtgccag ctggattaat    6780
gaatcggcca acgcgcgggg agaggcggtt tgcgtattgg gcgctcttcc gcttcctcgc    6840
tcactgactc gctgcgctcg tcgttcggc tgcggcgagc ggtatcagct cactcaaagg     6900
cggtaatacg gttatccaca gaatcagggg ataacgcagg aaagaacatg tgagcaaaag    6960
gccagcaaaa ggccaggaac cgtaaaaagg ccgcgttgct ggcgtttttc cataggctcc    7020
gcccccctga cgagcatcac aaaaatcgac gctcaagtca gaggtggcga aacccgacag    7080
gactataaag ataccaggcg tttccccctg gaagctccct cgtgcgctct cctgttccga    7140
ccctgccgct taccggatac ctgtccgcct ttctcccttc gggaagcgtg gcgctttctc    7200
aatgctcacg ctgtaggtat ctcagttcgg tgtaggtcgt tcgctccaag ctgggctgtg    7260
tgcacgaacc cccgttcag cccgaccgct gcgccttatc cggtaactat cgtcttgagt      7320
```

```
ccaacccggt aagacacgac ttatcgccac tggcagcagc cactggtaac aggattagca    7380
gagcgaggta tgtaggcggt gctacagagt tcttgaagtg gtggcctaac tacggctaca    7440
ctagaaggac agtatttggt atctgcgctc tgctgaagcc agttaccttc ggaaaaagag    7500
ttggtagctc ttgatccggc aaacaaacca ccgctggtag cggtggtttt tttgtttgca    7560
agcagcagat tacgcgcaga aaaaaggat ctcaagaaga tcctttgatc ttttctacgg     7620
ggtctgacgc tcagtggaac gaaaactcac gttaagggat tttggtcatg agattatcaa    7680
aaaggatctt cacctagatc cttttaaatt aaaaatgaag ttttaaatca atctaaagta    7740
tatatgagta aacttggtct gacagttacc aatgcttaat cagtgaggca cctatctcag    7800
cgatctgtct atttcgttca tccatagttg cctgactccc cgtcgtgtag ataactacga    7860
tacgggaggg cttaccatct ggccccagtg ctgcaatgat accgcgagac ccacgctcac    7920
cggctccaga tttatcagca ataaaccagc cagccggaag ggccgagcgc agaagtggtc    7980
ctgcaacttt atccgcctcc atccagtcta ttaattgttg ccgggaagct agagtaagta    8040
gttcgccagt taatagtttg cgcaacgttg ttgccattgc tgctggcatc gtggtgtcac    8100
gctcgtcgtt tggtatggct tcattcagct ccggttccca acgatcaagg cgagttacat    8160
gatcccccat gttgtgcaaa aaagcggtta gctccttcgg tcctccgatc gttgtcagaa    8220
gtaagttggc cgcagtgtta tcactcatgg ttatggcagc actgcataat tctcttactg    8280
tcatgccatc cgtaagatgc ttttctgtga ctggtgagta ctcaaccaag tcattctgag    8340
aatagtgtat gcggcgaccg agttgctctt gcccggcgtc atcacgggat aataccgcgc    8400
cacatagcag aactttaaaa gtgctcatca ttggaaaacg ttcttcgggg cgaaaactct    8460
caaggatctt accgctgttg agatccagtt cgatgtaacc cactcgtgca cccaactgat    8520
cttcagcatc ttttactttc accagcgttt ctgggtgagc aaaaacagga aggcaaaatg    8580
ccgcaaaaaa gggaataagg gcgacacgga aatgttgaat actcatactc ttcctttttc    8640
aatattattg aagcatttat cagggttatt gtctcatgag cggatacata tttgaatgta    8700
tttagaaaaa taaacaaata ggggttccgc gcacatttcc ccgaaaagtg ccacctgacg    8760
tctaagaaac cattattatc atgacattaa cctataaaaa taggcgtatc acgaggccct    8820
ttcgtcttca agaatactgc ctcgcgcgtt tcggtgatga cggtgaaaac ctctgacaca    8880
tgcagctccc ggagacggtc acagcttgtc tgtaagcgga tgccgggagc agacaagccc    8940
gtcagggcgc gtcagcgggt gttggcgggt gtcggggcgc agccatgacc cagtcacgta    9000
gcgatagcgg agtggctta actatgcgg atcagagcag attgtactga gagtgcacca      9060
tatgcggtgt gaaataccgc acagatgcgt aaggagaaaa taccgcatca ggcgccattc    9120
gccattcagg ctacgcaact gttgggaagg gcgatcggtg cgggcctctt cgctattacg    9180
ccagctggcg aaggggggat gtgctgcaag gcgattaagt tgggtaacgc cagggttttc    9240
ccagtcacga cgttgtaaaa cgacggccag tgcc                                9274
```

<210> SEQ ID NO 2
<211> LENGTH: 3768
<212> TYPE: DNA
<213> ORGANISM: Homo sapiens

<400> SEQUENCE: 2

```
atggagctgg cggccttgtg ccgctggggg ctcctcctcg ccctcttgcc ccccggagcc     60
gcgagcaccc aagtgtgcac cggcacagac atgaagctgc ggctccctgc cagtcccgag    120
```

-continued

```
acccacctgg acatgctccg ccacctctac cagggctgcc aggtggtgca gggaaacctg      180
gaactcacct acctgcccac caatgccagc ctgtccttcc tgcaggatat ccaggaggtg      240
cagggctacg tgctcatcgc tcacaaccaa gtgaggcagg tcccactgca gaggctgcgg      300
attgtgcgag cacccagct ctttgaggac aactatgccc tggccgtgct agacaatgga       360
gacccgctga caataccac ccctgtcaca ggggcctccc caggaggcct gcgggagctg       420
cagcttcgaa gcctcacaga gatcttgaaa ggagggtct tgatccagcg aaccccag        480 ctctgctacc aggacacgat tttgtggaag acatcttcc acaagaacaa ccagctggct       540
ctcacactga tagacaccaa ccgctctcgg gcctgccacc cctgttctcc gatgtgtaag     600
ggctcccgct gctggggaga gagttctgag gattgtcaga gcctgacgcg cactgtctgt    660
gccggtggct gtgcccgctg caaggggcca ctgcccactg actgctgcca tgagcagtgt    720
gctgccggct gcacgggccc caagcactct gactgcctgg cctgcctcca cttcaaccac   780
agtggcatct gtgagctgca ctgcccagcc ctggtcacct acaacacaga cacgtttgag   840
tccatgccca atcccgaggg ccggtataca ttcggcgcca gctgtgtgac tgcctgtccc    900
tacaactacc tttctacgga cgtgggatcc tgcaccctcg tctgcccct gcacaaccaa      960 gaggtgacag cagaggatgg aacacagcgg tgtgagaagt gcagcaagcc ctgtgcccga    1020
gtgtgctatg gtctgggcat ggagcacttg cgagaggtga gggcagttac cagtgccaat   1080
atccaggagt ttgctggctg caagaagatc tttgggagcc tggcatttct gccggagagc   1140
tttgatgggg acccagcctc caacactgcc ccgctccagc cagagcagct ccaagtgttt    1200
gagactctgg aagagatcac aggttaccta tacatctcag catggccgga cagcctgcct   1260
gacctcagcg tcttccagaa cctgcaagta atccggggac gaattctgca caatggcgcc    1320
tactcgctga ccctgcaagg gctgggcatc agctggctgg ggctgcgctc actgagggaa   1380
ctgggcagtg gactggccct catccaccat aacacccacc tctgcttcgt gcacacggtg   1440
ccctgggacc agctctttcg gaacccgcac caagctctgc tccacactgc caaccggcca   1500
gaggacgagt gtgtgggcga gggcctggcc tgccaccagc tgtgcgcccg agggcactgc    1560
tggggtccag ggcccaccca gtgtgtcaac tgcagccagt tccttcgggg ccaggagtgc    1620
gtggaggaat gccgagtact gcaggggctc cccaggagt atgtgaatgc caggcactgt     1680
ttgccgtgcc accctgagtg tcagcccag aatggctcag tgacctgttt tggaccggag    1740
gctgaccagt gtgtggcctg tgcccactat aaggaccctc ccttctgcgt ggcccgctgc    1800
cccagcggtg tgaaacctga cctctcctac atgcccatct ggaagtttcc agatgaggag   1860
ggcgcatgcc agccttgccc catcaactgc acccactcct gtgtggacct ggatgacaag    1920
ggctgccccg ccgagcagag agccagccct ctgacgtcca tcgtctctgc ggtggttggc    1980
attctgctgg tcgtggtctt ggggtggtc tttgggatcc tcatcaagcg acggcagcag     2040
aagatccgga gtacacgat gcggagactg ctgcaggaaa cggagctggt ggagccgctg    2100
acacctagcg gagcgatgcc caaccaggcg cagatgcgga tcctgaaaga gacggagctg   2160
aggaaggtga aggtgcttgg atctggcgct tttggcacag tctacaaggg catctggatc   2220
cctgatgggg agaatgtgaa aattccagtg gccatcaaag tgttgaggga aaacacatcc   2280
cccaaagcca acaaagaaat cttagacgaa gcatacgtga tggctggtgt gggctcccca   2340
tatgtctccc gccttctggg catctgcctg acatccacgg tgcagctggt gacacagctt   2400 atgcctatg gctgcctctt agaccatgtc cgggaaaacc gcggacgcct gggctcccag    2460
gacctgctga actggtgtat gcagattgcc aagggatga gctacctgga ggatgtgcgg   2520
```

-continued

```
ctcgtacaca gggacttggc cgctcggaac gtgctggtca agagtcccaa ccatgtcaaa      2580
attacagact tcgggctggc tcggctgctg gacattgacg agacagagta ccatgcagat      2640
gggggcaagg tgcccatcaa gtggatggcg ctggagtcca ttctccgccg gcggttcacc      2700
caccagagtg atgtgtggag ttatggtgtg actgtgtggg agctgatgac ttttggggcc      2760
aaaccttacg atgggatccc agcccggagg atccctgacc tgctggaaaa ggggagcgg       2820 ctgccccagc cccccatctg caccattgat gtctacatga tcatggtcaa atgttggatg      2880
attgactctg aatgtcggcc aagattccgg gagttggtgt ctgaattctc ccgcatggcc      2940 agggacccc agcgctttgt ggtcatccag aatgaggact tgggcccagc cagtcccttg       3000
gacagcacct tctaccgctc actgctggag gacgatgaca tgggggacct ggtggatgct      3060
gaggagtatc tggtacccca gcagggcttc ttctgtccag accctgcccc gggcgctggg      3120
ggcatggtcc accacaggca ccgcagctca tctaccagga gtggcggtgg ggacctgaca      3180
ctagggctgg agccctctga agaggaggcc cccaggtctc cactggcacc ctccgaaggg      3240
gctggctccg atgtatttga tggtgacctg ggaatggggg cagccaaggg gctgcaaagc      3300
ctccccacac atgaccccag ccctctacag cggtacagtg aggaccccac agtacccctg      3360
ccctctgaga ctgatggcta cgttgccccc ctgacctgca gccccagcc tgaatatgtg       3420 aaccagccag atgttcggcc ccagccccct tcgccccgag agggccctct gcctgctgcc      3480
cgacctgctg gtgccactct ggaaagggc aagactctct ccccagggaa gaatggggtc       3540
gtcaaagacg ttttgccctt tgggggtgcc gtggagaacc ccgagtactt gacacccag       3600 ggaggagctg ccctcagcc ccaccctcct cctgccttca gcccagcctt cgacaacctc       3660
tattactggg accaggaccc accagagcgg ggggctccac ccagcacctt caaagggaca      3720
cctacggcag agaacccaga gtacctgggt ctggacgtgc cagtgtga                   3768
```

<210> SEQ ID NO 3
<211> LENGTH: 1255
<212> TYPE: PRT
<213> ORGANISM: Homo sapiens

<400> SEQUENCE: 3

```
Met Glu Leu Ala Ala Leu Cys Arg Trp Gly Leu Leu Ala Leu Leu Leu
  1               5                  10                  15

Pro Pro Gly Ala Ala Ser Thr Gln Val Cys Thr Gly Thr Asp Met Lys
             20                  25                  30

Leu Arg Leu Pro Ala Ser Pro Glu Thr His Leu Asp Met Leu Arg His
         35                  40                  45

Leu Tyr Gln Gly Cys Gln Val Val Gln Gly Asn Leu Glu Leu Thr Tyr
     50                  55                  60

Leu Pro Thr Asn Ala Ser Leu Ser Phe Leu Gln Asp Ile Gln Glu Val
 65                  70                  75                  80

Gln Gly Tyr Val Leu Ile Ala His Asn Gln Val Arg Gln Val Pro Leu
                 85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
```

```
145                 150                 155                 160
Leu Cys Tyr Gln Asp Thr Ile Leu Trp Lys Asp Ile Phe His Lys Asn
                165                 170                 175
Asn Gln Leu Ala Leu Thr Leu Ile Asp Thr Asn Arg Ser Arg Ala Cys
                180                 185                 190
His Pro Cys Ser Pro Met Cys Lys Gly Ser Arg Cys Trp Gly Glu Ser
                195                 200                 205
Ser Glu Asp Cys Gln Ser Leu Thr Arg Thr Val Cys Ala Gly Gly Cys
        210                 215                 220
Ala Arg Cys Lys Gly Pro Leu Pro Thr Asp Cys Cys His Glu Gln Cys
225                 230                 235                 240
Ala Ala Gly Cys Thr Gly Pro Lys His Ser Asp Cys Leu Ala Cys Leu
                245                 250                 255
His Phe Asn His Ser Gly Ile Cys Glu Leu His Cys Pro Ala Leu Val
                260                 265                 270
Thr Tyr Asn Thr Asp Thr Phe Glu Ser Met Pro Asn Pro Glu Gly Arg
                275                 280                 285
Tyr Thr Phe Gly Ala Ser Cys Val Thr Ala Cys Pro Tyr Asn Tyr Leu
                290                 295                 300
Ser Thr Asp Val Gly Ser Cys Thr Leu Val Cys Pro Leu His Asn Gln
305                 310                 315                 320
Glu Val Thr Ala Glu Asp Gly Thr Gln Arg Cys Glu Lys Cys Ser Lys
                325                 330                 335
Pro Cys Ala Arg Val Cys Tyr Gly Leu Gly Met Glu His Leu Arg Glu
                340                 345                 350
Val Arg Ala Val Thr Ser Ala Asn Ile Gln Glu Phe Ala Gly Cys Lys
                355                 360                 365
Lys Ile Phe Gly Ser Leu Ala Phe Leu Pro Glu Ser Phe Asp Gly Asp
                370                 375                 380
Pro Ala Ser Asn Thr Ala Pro Leu Gln Pro Glu Gln Leu Gln Val Phe
385                 390                 395                 400
Glu Thr Leu Glu Glu Ile Thr Gly Tyr Leu Tyr Ile Ser Ala Trp Pro
                405                 410                 415
Asp Ser Leu Pro Asp Leu Ser Val Phe Gln Asn Leu Gln Val Ile Arg
                420                 425                 430
Gly Arg Ile Leu His Asn Gly Ala Tyr Ser Leu Thr Leu Gln Gly Leu
                435                 440                 445
Gly Ile Ser Trp Leu Gly Leu Arg Ser Leu Arg Glu Leu Gly Ser Gly
                450                 455                 460
Leu Ala Leu Ile His His Asn Thr His Leu Cys Phe Val His Thr Val
465                 470                 475                 480
Pro Trp Asp Gln Leu Phe Arg Asn Pro His Gln Ala Leu Leu His Thr
                485                 490                 495
Ala Asn Arg Pro Glu Asp Glu Cys Val Gly Glu Gly Leu Ala Cys His
                500                 505                 510
Gln Leu Cys Ala Arg Gly His Cys Trp Gly Pro Gly Pro Thr Gln Cys
                515                 520                 525
Val Asn Cys Ser Gln Phe Leu Arg Gly Gln Glu Cys Val Glu Glu Cys
                530                 535                 540
Arg Val Leu Gln Gly Leu Pro Arg Glu Tyr Val Asn Ala Arg His Cys
545                 550                 555                 560
Leu Pro Cys His Pro Glu Cys Gln Pro Gln Asn Gly Ser Val Thr Cys
                565                 570                 575
```

-continued

```
Phe Gly Pro Glu Ala Asp Gln Cys Val Ala Cys Ala His Tyr Lys Asp
                580                 585                 590

Pro Pro Phe Cys Val Ala Arg Cys Pro Ser Gly Val Lys Pro Asp Leu
            595                 600                 605

Ser Tyr Met Pro Ile Trp Lys Phe Pro Asp Glu Gly Ala Cys Gln
        610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Val Ser
                645                 650                 655

Ala Val Val Gly Ile Leu Leu Val Val Val Leu Gly Val Val Phe Gly
            660                 665                 670

Ile Leu Ile Lys Arg Arg Gln Gln Lys Ile Arg Lys Tyr Thr Met Arg
        675                 680                 685

Arg Leu Leu Gln Glu Thr Glu Leu Val Glu Pro Leu Thr Pro Ser Gly
        690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
        755                 760                 765

Asp Glu Ala Tyr Val Met Ala Gly Val Gly Ser Pro Tyr Val Ser Arg
770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
        835                 840                 845

Arg Asn Val Leu Val Lys Ser Pro Asn His Val Lys Ile Thr Asp Phe
850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
        915                 920                 925

Arg Glu Ile Pro Asp Leu Leu Lys Gly Arg Leu Pro Gln Pro
930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
            980                 985                 990
```

-continued

```
Asp Leu Gly Pro Ala Ser Pro Leu Asp Ser Thr Phe Tyr Arg Ser Leu
            995                 1000                1005

Leu Glu Asp Asp Met Gly Asp Leu Val Asp Ala Glu Glu Tyr Leu
       1010                1015                1020

Val Pro Gln Gln Gly Phe Phe Cys Pro Asp Pro Ala Pro Gly Ala Gly
1025                1030                1035                1040

Gly Met Val His His Arg His Arg Ser Ser Ser Thr Arg Ser Gly Gly
            1045                1050                1055

Gly Asp Leu Thr Leu Gly Leu Glu Pro Ser Glu Glu Glu Ala Pro Arg
            1060                1065                1070

Ser Pro Leu Ala Pro Ser Glu Gly Ala Gly Ser Asp Val Phe Asp Gly
            1075                1080                1085

Asp Leu Gly Met Gly Ala Ala Lys Gly Leu Gln Ser Leu Pro Thr His
            1090                1095                1100

Asp Pro Ser Pro Leu Gln Arg Tyr Ser Glu Asp Pro Thr Val Pro Leu
1105                1110                1115                1120

Pro Ser Glu Thr Asp Gly Tyr Val Ala Pro Leu Thr Cys Ser Pro Gln
            1125                1130                1135

Pro Glu Tyr Val Asn Gln Pro Asp Val Arg Pro Gln Pro Pro Ser Pro
            1140                1145                1150

Arg Glu Gly Pro Leu Pro Ala Ala Arg Pro Ala Gly Ala Thr Leu Glu
            1155                1160                1165

Arg Ala Lys Thr Leu Ser Pro Gly Lys Asn Gly Val Val Lys Asp Val
            1170                1175                1180

Phe Ala Phe Gly Gly Ala Val Glu Asn Pro Glu Tyr Leu Thr Pro Gln
1185                1190                1195                1200

Gly Gly Ala Ala Pro Gln Pro His Pro Pro Ala Phe Ser Pro Ala
            1205                1210                1215

Phe Asp Asn Leu Tyr Tyr Trp Asp Gln Asp Pro Pro Glu Arg Gly Ala
            1220                1225                1230

Pro Pro Ser Thr Phe Lys Gly Thr Pro Thr Ala Glu Asn Pro Glu Tyr
            1235                1240                1245

Leu Gly Leu Asp Val Pro Val
1250                1255

<210> SEQ ID NO 4
<211> LENGTH: 9274
<212> TYPE: DNA
<213> ORGANISM: Artificial Sequence
<220> FEATURE:
<223> OTHER INFORMATION: Vector Sequence

<400> SEQUENCE: 4
ttcgagctag ccacgtgtaa ttaagtacta gcgctcgatc gtcgaacgta cggacgtcgt      60
ctttaccaac ttgagggctc tcacaggatg tggatcccct cttcgtcggt tccccaacaa    120
agggtggttc ctgctgggca gacgcgtgtt tgcctactcg ggtagtctgt ttctgtataa    180
gtaagagacg acgtttgaac cgtatcgaga cgaaacgacc ccgtaacccc cttcaacgcc    240
aagcacgagc gtcccgagag tgggaactga gaaaattatc gagaagacac gttctaatgt    300
tagatttgtt aagcctcttg agctggaagg agaggactcc gttcctggtg tcggttgaag    360
gagaatgttc ggcgtagcta aacaggaag  tctttatctt tattcttacg aacgattttt    420
aatataaaaa tggttattct ggttaggtta tccatctaat aatcaatgat acaattcttt    480
acttagtaat agaaaatcat gataaaaatg agtttaagtc ttcaatcttt acccttatct    540
```

-continued

| | |
|---|---|
| tttatctttc tctgcgagtt ggagttaact tcttgtccac gttcctgata actggtgtcc | 600 |
| ggatcttcat tttttccctt ttttctcaca aaaacagttt tatcctctgt ccaccaccgt | 660 |
| tggtccctga atatccctg gaatgtagat gtctggttgt ctacggggga atggtatatg | 720 |
| tccttctata ctgaatttaa ccctatccac ccaatgtcag ttaccgatat ttcacaatat | 780 |
| atctagggag ggaaaagcac tttctgagcg gtctcgatct ggaggaacca catacaacag | 840 |
| agttcttctt tttctgctgt actttgttgt ccatgtacta atataaatag atccttgtcc | 900 |
| ttacgtgaaa acccctttct aaaggtatg gttcctcccc tgtcaccgac ctgattatct | 960 |
| tgtaataaga cgttttttgaa taccgtactc aataatactt atcggaaata accgggttgg | 1020 |
| aacgccaagg gttccgaatt cattcaaaaa ccaatgtttg acaagaattt tgctcctaca | 1080 |
| ctctgttcac caaaggactg aaccaaacca tagtttccaa gactagactc gagactcaca | 1140 |
| agataaaagg atacaagaaa accttaaata ggtttagaat acatttacga atacatttgg | 1200 |
| ttctatattt tctcacgact aaaaaactca tttgaacgtt gtcaggattg taagtggaga | 1260 |
| acacacaaac acagacaagc ggtagggcag aggcgagcag tgaataggaa gtgaaaggtc | 1320 |
| tcccaggggg gcgtctgggg cctagcgatc gagcgcttag ctattcgaac gccggcgaat | 1380 |
| tgacgtcttc aaccagcact ccgtgacccg tccattcata gttccaatgt tctgtccaaa | 1440 |
| ttcctctggt tatctttgac ccgaacagct ctgtctcttc tgagaacgca aagactatcc | 1500 |
| gtggataacc agaatgactg taggtgaaac ggaaagagag gtgtccacag gtgagggtcc | 1560 |
| aagttaatgt cgagaattcg ccggcgttcg aactatagct taaggacgtc gggcccccta | 1620 |
| ggtgatcacc taggtttctt aagttttcg aagagctccc gcgcgcgggc cggggtggg | 1680 |
| gagcgtcgtg gggcgcgggg cgcgggaggg tcggcccagg tcggcctcgg tacctcgacc | 1740 |
| gccggaacac ggcgaccccc gaggaggagc gggagaacgg ggggcctcgg cgctcgtggg | 1800 |
| ttcacacgtg gccgtgtctg tacttcgacg ccgagggacg gtcagggctc tgggtggacc | 1860 |
| tgtacgaggc ggtggagatg gtcccgacgg tccaccacgt ccctttggac cttgagtgga | 1920 |
| tggacgggtg gttacggtcg gacaggaagg acgtcctata ggtcctccac gtcccgatgc | 1980 |
| acgagtagcg agtgttggtt cactccgtcc agggtgacgt ctccgacgcc taacacgctc | 2040 |
| cgtgggtcga gaaactcctg ttgatacggg accggcacga tctgttacct ctgggcgact | 2100 |
| tgttatggtg gggacagtgt ccccggaggg gtcctccgga cgccctcgac gtcgaagctt | 2160 |
| cggagtgtct ctagaacttt cctccccaga actaggtcgc cttgggggtc gagacgatgg | 2220 |
| tcctgtgcta aaacaccttc ctgtagaagg tgttcttgtt ggtcgaccga gagtgtgact | 2280 |
| atctgtggtt ggcgagagcc cggacggtgg ggacaagagg ctacacattc ccgagggcga | 2340 |
| cgacccctct ctcaagactc ctaacagtct cggactgcgc gtgacagaca cggccaccga | 2400 |
| cacgggcgac gttccccggt gacgggtgac tgacgacggt actcgtcaca cgacggccga | 2460 |
| cgtgcccggg gttcgtgaga ctgacggacc ggacggaggt gaagttggtg tcaccgtaga | 2520 |
| cactcgacgt gacgggtcgg gaccagtgga tgttgtgtct gtgcaaactc aggtacgggt | 2580 |
| tagggctccc ggccatatgt aagccgcggt cgacacactg acggacaggg atgttgatgg | 2640 |
| aaagatgcct gcaccctagg acgtgggagc agacggggga cgtgttggtt ctccactgtc | 2700 |
| gtctcctacc ttgtgtcgcc acactcttca cgtcgttcgg gacacgggct cacacgatac | 2760 |
| cagacccgta cctcgtgaac gctctccact cccgtcaatg gtcacggtta taggtcctca | 2820 |
| aacgaccgac gttcttctag aaaccctcgg accgtaaaga cggcctctcg aaactacccc | 2880 |
| tgggtcggag gttgtgacgg ggcgaggtcg gtctcgtcga ggttcacaaa ctctgagacc | 2940 |

```
ttctctagtg tccaatggat atgtagagtc gtaccggcct gtcggacgga ctggagtcgc      3000
agaaggtctt ggacgttcat taggcccctg cttaagacgt gttaccgcgg atgagcgact      3060
gggacgttcc cgacccgtag tcgaccgacc ccgacgcgag tgactccctt gacccgtcac      3120
ctgaccggga gtaggtggta ttgtgggtgg agacgaagca cgtgtgccac gggaccctgg      3180
tcgagaaagc cttgggcgtg gttcgagacg aggtgtgacg gttggccggt ctcctgctca      3240
cacacccgct cccggaccgg acggtggtcg acacgcgggc tcccgtgacg accccaggtc      3300
ccgggtgggt cacacagttg acgtcggtca aggaagcccc ggtcctcacg cacctcctta      3360
cggctcatga cgtccccgag gggtccctca tacacttacg gtccgtgaca acggcacgg       3420 tgggactcac agtcggggtc ttaccgagtc actggacaaa acctggcctc cgactggtca      3480
cacaccggac acgggtgata ttcctgggag ggaagacgca ccgggcgacg gggtcgccac      3540
actttggact ggagaggatg tacgggtaga ccttcaaagg tctactcctc ccgcgtacgg      3600
tcggaacggg gtagttgacg tgggtgagga cacacctgga cctactgttc ccgacggggc      3660
ggctcgtctc tcggtcggga gactgcaggt agcagagacc ccaccaaccg taagacgacc      3720
agcaccagaa cccccaccag aaaccctagg agtagttcgc tgccgtcgtc ttctaggcct      3780
tcatgtgcta cgcctctgac gacgtccttt gcctcgacca cctcggcgac tgtggatcgc      3840
ctcgctacgg gttggtccgc gtctacgcct aggactttct ctgcctcgac tccttccact      3900
tccacgaacc tagaccgcga aaaccgtgtc agatgttccc gtagacctag ggactacccc      3960
tcttacactt ttaaggtcac cggtagtttc acaactccct tttgtgtagg gggtttcggt      4020
tgtttcttta gaatctgctt cgtatgcact accgaccaca cccgaggggt atacagaggg      4080
cggaagaccc gtagacggac tgtaggtgcc acgtcgacca ctgtgtcgaa tacgggatac      4140
cgacggagaa tctggtacag gccctttggg cgcctgcgga cccagggtc ctggacgact        4200 tgaccacata cgtctaacgg ttcccctact cgatggacct cctacacgcc gagcatgtgt      4260
ccctgaaccg gcgagccttg cacgaccagt tctcagggtt ggtacagttt taatgtctga      4320
agcccgaccg agccgacgac ctgtaactgc tctgtctcat ggtacgtcta ccccgttcc       4380 acgggtagtt cacctaccgc gacctcaggt aagaggcggc cgccaagtgg gtggtctcac      4440
tacacacctc ataccacac tgacacaccc tcgactactg aaaaccccgg tttggaatgc        4500
taccctaggg tcgggccctc tagggactgg acgaccttt ccccctcgcc gacgggtcg         4560 gggggtagac gtggtaacta cagatgtact agtaccagtt tacaacctac taactgagac      4620
ttacagccgg ttctaaggcc ctcaaccaca gacttaagag ggcgtaccgg tccctgggg        4680 tcgcgaaaca ccagtaggtc ttactcctga acccgggtcg gtcagggaac ctgtcgtgga      4740
agatggcgag tgacgacctc ctgctactgt acccctgga ccacctacga ctcctcatag       4800
accatggggt cgtcccgaag aagacaggtc tgggacgggg cccgcgaccc ccgtaccagg      4860
tggtgtccgt ggcgtcgagt agatggtcct caccgccacc cctggactgt gatcccgacc      4920
tcgggagact tctcctccgg gggtccagag gtgaccgtgg gaggcttccc cgaccgaggc      4980
tacataaact accactggac ccttaccccc gtcggttccc cgacgtttcg gagggtgtg       5040 tactgggtc gggagatgtc gccatgtcac tcctggggtg tcatggggac gggagactct        5100
gactaccgat gcaacggggg gactggacgt cggggtcgg acttatacac ttggtcggtc       5160
tacaagccgg ggtcggggga agcggggctc tcccgggaga cggacgacgg gctgacgac       5220 cacggtgaga ccttccccgg ttctgagaga gggtcccctt cttaccccag cagtttctgc      5280
```

-continued

| | | | | | |
|---|---|---|---|---|---|
| aaaaacggaa | accccacgg | cacctcttgg | ggctcatgaa | ctgtggggtc | cctcctcgac | 5340 |
| ggggagtcgg | ggtgggagga | ggacggaagt | cgggtcggaa | gctgttggag | ataatgaccc | 5400 |
| tggtcctggg | tggtctcgcc | ccccgaggtg | ggtcgtggaa | gtttccctgt | ggatgccgtc | 5460 |
| tcttgggtct | catggaccca | gacctgcacg | gtcacacttg | gtcttccggt | tcaggcgtct | 5520 |
| tcgggactac | acaggagtcc | ctcgtcccct | ccgccgagag | ctcgataagg | tcttcatcac | 5580 |
| tcctccgaaa | aaacctccgg | atccgaaaac | gtttttcgaa | tagctatggc | agctgagctc | 5640 |
| tcatgaagat | ctcgccggcg | cccgggtagc | ggagactgtc | gttgcagata | ctggaggatt | 5700 |
| tcctggatct | ccttccgtag | gtttgcgact | acccctccga | ccttctaccg | tcggggggcct | 5760 |
| gacccgtcta | gaagttcgtc | tggatgtcgt | tcaagctgtg | tttgagtgtg | ttgctactgc | 5820 |
| gtgatgagtt | cttgatgccc | gacgagatga | cgaagtcctt | cctgtacctg | ttccagctct | 5880 |
| gtaaggacgc | gtagcacgtc | acggcgagac | acctcccgtc | gacaccgaag | atcgacgggc | 5940 |
| ccaccgtagg | gacactgggg | aggggtcacg | gagaggaccg | ggaccttcaa | cggtgaggtc | 6000 |
| acgggtggtc | ggaacaggat | tattttaatt | caacgtagta | aaacagactg | atccacagga | 6060 |
| agatattata | atacccacc | tccccccacc | atacctcgtt | ccccgggttc | aacccttctg | 6120 |
| ttggacatcc | cggacgcccc | agataagccc | ttggttcgac | ctcacgtcac | cgtgttagaa | 6180 |
| ccgagtgacg | ttagaggcgg | aggacccaag | ttcgctaaga | ggacggagtc | ggagggctca | 6240 |
| acaaccctaa | ggtccgtacg | tactggtccg | agtcgattaa | aaacaaaaaa | accatctctg | 6300 |
| ccccaaagtg | gtataaccgg | tccgaccaga | ggttgaggat | tagagtccac | tagatgggtg | 6360 |
| gaaccggagg | gtttaacgac | cctaatgtcc | gcacttggtg | acgagggaag | ggacaggaag | 6420 |
| actaaaattt | tattgatatg | gtcgtcctcc | tgcaggtctg | tgtcgtatcc | gatggacggt | 6480 |
| accgggttgg | ccaccctgta | aactcaacga | acgaaccgtg | acaggagagt | acgcaaccca | 6540 |
| ggtgagtcat | ctacgacaa | cttaatgcta | gccacgtgta | attaagtact | ttaagcatta | 6600 |
| gtaccagtat | cgacaaagga | cacactttaa | caataggcga | gtgttaaggt | gtgttgtatg | 6660 |
| ctcggccttc | gtatttcaca | tttcggaccc | cacggattac | tcactccatt | gagtgtaatt | 6720 |
| aacgcaacgc | gagtgacggg | cgaaaggtca | gcccttggga | cagcacggtc | gacctaatta | 6780 |
| cttagccggt | tgcgcgcccc | tctccgccaa | acgcataacc | cgcgagaagg | cgaaggagcg | 6840 |
| agtgactgag | cgacgcgagc | cagcaagccg | acgccgctcg | ccatagtcga | gtgagtttcc | 6900 |
| gccattatgc | caataggtgt | cttagtcccc | tattgcgtcc | tttcttgtac | actcgttttc | 6960 |
| cggtcgtttt | ccggtccttg | gcattttttcc | ggcgcaacga | ccgcaaaaag | gtatccgagg | 7020 |
| cgggggggact | gctcgtagtg | tttttagctg | cgagttcagt | ctccaccgct | ttgggctgtc | 7080 |
| ctgatatttc | tatggtccgc | aaaggggggac | cttcgaggga | gcacgcgaga | ggacaaggct | 7140 |
| gggacggcga | atggcctatg | gacaggcgga | agaggggaag | cccttcgcac | cgcgaaagag | 7200 |
| ttacgagtgc | gacatccata | gagtcaagcc | acatccagca | agcgaggttc | gacccgacac | 7260 |
| acgtgcttgg | ggggcaagtc | gggctggcga | cgcggaatag | gccattgata | gcagaactca | 7320 |
| ggttgggcca | ttctgtgctg | aatagcggtg | accgtcgtcg | gtgaccattg | tcctaatcgt | 7380 |
| ctcgctccat | acatccgcca | cgatgtctca | agaacttcac | caccggattg | atgccgatgt | 7440 |
| gatcttcctg | tcataaacca | tagacgcgag | acgacttcgg | tcaatggaag | cctttttctc | 7500 |
| aaccatcgag | aactaggccg | tttgtttggt | ggcgaccatc | gccaccaaaa | aaacaaacgt | 7560 |
| tcgtcgtcta | atgcgcgtct | ttttttccta | gagttcttct | aggaaactag | aaaagatgcc | 7620 |
| ccagactgcg | agtcaccttg | cttttgagtg | caattcccta | aaaccagtac | tctaatagtt | 7680 |

```
tttcctagaa gtggatctag gaaaatttaa tttttacttc aaaatttagt tagatttcat      7740
atatactcat ttgaaccaga ctgtcaatgg ttacgaatta gtcactccgt ggatagagtc      7800
gctagacaga taaagcaagt aggtatcaac ggactgaggg gcagcacatc tattgatgct      7860
atgccctccc gaatggtaga ccggggtcac gacgttacta tggcgctctg ggtgcgagtg      7920
gccgaggtct aaatagtcgt tatttggtcg gtcggccttc ccggctcgcg tcttcaccag      7980
gacgttgaaa taggcggagg taggtcagat aattaacaac ggcccttcga tctcattcat      8040
caagcggtca attatcaaac gcgttgcaac aacggtaacg acgaccgtag caccacagtg      8100
cgagcagcaa accataccga agtaagtcga ggccaagggt tgctagttcc gctcaatgta      8160 ctaggggta caacacgttt tttcgccaat cgaggaagcc aggaggctag caacagtctt       8220
cattcaaccg gcgtcacaat agtgagtacc aataccgtcg tgacgtatta agagaatgac      8280
agtacggtag gcattctacg aaaagacact gaccactcat gagttggttc agtaagactc      8340
ttatcacata cgccgctggc tcaacgagaa cgggccgcag tagtgcccta ttatggcgcg      8400
gtgtatcgtc ttgaaatttt cacgagtagt aacctttgc aagaagcccc gcttttgaga       8460
gttcctagaa tggcgacaac tctaggtcaa gctacattgg gtgagcacgt gggttgacta      8520
gaagtcgtag aaaatgaaag tggtcgcaaa gacccactcg tttttgtcct tccgttttac      8580
ggcgtttttt cccttattcc cgctgtgcct ttacaactta tgagtatgag aaggaaaaag      8640
ttataataac ttcgtaaata gtcccaataa cagagtactc gcctatgtat aaacttacat      8700 aaatctttt atttgtttat ccccaaggcg cgtgtaaagg ggcttttcac ggtggactgc       8760
agattctttg gtaataatag tactgtaatt ggatatttt atccgcatag tgctccggga       8820
aagcagaagt tcttatgacg gagcgcgcaa agccactact gccacttttg gagactgtgt      8880
acgtcgaggg cctctgccag tgtcgaacag acattcgcct acggccctcg tctgttcggg      8940
cagtcccgcg cagtcgccca caaccgccca cagccccgcg tcggtactgg gtcagtgcat      9000
cgctatcgcc tcaaccgaat tgatacgccg tagtctcgtc taacatgact ctcacgtggt      9060
atacgccaca ctttatggcg tgtctacgca ttcctctttt atggcgtagt ccgcggtaag      9120
cggtaagtcc gatgcgttga caaccccttcc cgctagccac gcccggagaa gcgataatgc    9180
ggtcgaccgc ttccccccta cacgacgttc cgctaattca acccattgcg gtcccaaaag     9240
ggtcagtgct gcaacatttt gctgccggtc acgg                                 9274
```